United States Patent
Clement et al.

(10) Patent No.: US 11,746,354 B2
(45) Date of Patent: Sep. 5, 2023

(54) HOMOLOGY DEPENDENT REPAIR GENOME EDITING

(71) Applicant: Inari Agriculture Technology, Inc., Cambridge, MA (US)

(72) Inventors: Erik William Clement, Somerville, MA (US); Yajie Niu, Lexington, MA (US); Hannah Pham, Somerville, MA (US)

(73) Assignee: INARI AGRICULTURE TECHNOLOGY, INC., Cambridge, MA (US)

( * ) Notice: Subject to any disclaimer, the term of this patent is extended or adjusted under 35 U.S.C. 154(b) by 0 days.

(21) Appl. No.: 17/597,680

(22) PCT Filed: Jul. 16, 2020

(86) PCT No.: PCT/US2020/042358
§ 371 (c)(1),
(2) Date: Jan. 18, 2022

(87) PCT Pub. No.: WO2021/016043
PCT Pub. Date: Jan. 28, 2021

(65) Prior Publication Data
US 2022/0170034 A1 Jun. 2, 2022

Related U.S. Application Data

(60) Provisional application No. 62/876,519, filed on Jul. 19, 2019.

(51) Int. Cl.
*C12N 15/82* (2006.01)
*C12N 9/22* (2006.01)
*C12N 15/10* (2006.01)
*C12N 15/90* (2006.01)

(52) U.S. Cl.
CPC ............ *C12N 15/8213* (2013.01); *C12N 9/22* (2013.01); *C12N 15/102* (2013.01); *C12N 15/902* (2013.01); *C12N 2310/20* (2017.05)

(58) Field of Classification Search
None
See application file for complete search history.

(56) References Cited

U.S. PATENT DOCUMENTS

| | | |
|---|---|---|
| 5,169,776 A | 12/1992 | Weaver |
| 8,106,258 B2 | 1/2012 | Duncan |
| 11,168,319 B1 | 11/2021 | Clement et al. |
| 2004/0006783 A1 | 1/2004 | Yang et al. |
| 2015/0059010 A1 | 2/2015 | Cigan et al. |
| 2015/0082478 A1 | 3/2015 | Cigan et al. |
| 2015/0267189 A1 | 9/2015 | Angel et al. |
| 2016/0355838 A1 | 12/2016 | Septiningsih et al. |
| 2018/0223295 A1 | 8/2018 | Marling et al. |
| 2018/0326079 A1 | 11/2018 | Barnes et al. |
| 2019/0211344 A1 | 7/2019 | Krieger et al. |
| 2020/0080110 A1 | 3/2020 | Bundock |
| 2021/0363536 A1 | 11/2021 | Clement et al. |

FOREIGN PATENT DOCUMENTS

| | | |
|---|---|---|
| WO | 2016054326 A1 | 4/2016 |
| WO | 2017142923 A1 | 8/2017 |
| WO | 2018085693 A1 | 5/2018 |
| WO | 2019144124 A1 | 7/2019 |

OTHER PUBLICATIONS

Aksoy, Yagiz A., et al. "Chemical reprogramming enhances homology-directed genome editing in zebrafish embryos." Communications biology 2.1 (2019): 1-9. (Year: 2019).*
Chen, Jilin, et al. "An update on precision genome editing by homology-directed repair in plants." Plant Physiology 188.4 (2022): 1780-1794. (Year: 2022).*
Finney, Micaela, Joseph Romanowski, and Zach N. Adelman. "Strategies to improve homology-based repair outcomes following CRISPR-based gene editing in mosquitoes: lessons in how to keep any repair disruptions local." Virology Journal 19.1 (2022): 1-11. (Year: 2022).*
Arnoult et al., "Regulation of DNA repair pathway choice in S and G2 phases by the NHEJ inhibitor CYREN", Nature, vol. 549, pp. 1-22, 2017.
European Patent Office, "Extended European Search Report", issued in connection to Application No. 19741141.6, 7 pages, dated Nov. 23, 2021.
Yongwei et al., "Precise Genome Modification via Sequence-Specific Nucleases-Mediated Gene Targeting for Crop Improvement", Frontiers in Plant Science, vol. 7, Article 1928, pp. 1-14, Dec. 2016.
Aravind et al., "Conserved Domains in DNA Repair Proteins and Evolution of Repair Systems", Nucleic Acids Research, vol. 27, No. 5, pp. 1223-1242, 1999.
Arguello-Astorga et al., "A Novel Motif in Geminivirus Replication Proteins Interacts with the Plant Retinoblastoma-Related Protein", Journal of Virology, vol. 78, No. 9, pp. 4817-4826, May 2004.
Baltes et al., "DNA Replicons for Plant Genome Engineering", The Plant Cell, vol. 26, pp. 151-163, Jan. 2014.
Baxter-Burrell et al., "RopGAP4-dependent Rop GTPase Rheostat Control of *Arabidopsis* Oxygen Deprivation Tolerance", Science, vol. 296, No. 5575, pp. 2026-2028, Jun. 14, 2002.
Branco-Price et al., "Genome-Wide Analysis of Transcript Abundance and Translation in *Arabidopsis* Seedlings Subjected to Oxygen Deprivation", Annals of Botany, vol. 96, No. 4, pp. 647-666, Aug. 2005.

(Continued)

*Primary Examiner* — Weihua Fan
*Assistant Examiner* — Brian James Sullivan
(74) *Attorney, Agent, or Firm* — McKee, Voorhees & Sease, PLC

(57) ABSTRACT

Compounds and related reagents, systems, methods, and compositions for increasing the frequency of homology directed repair (HDR) of target genomic sites with genome editing molecules are provided.

20 Claims, No Drawings
Specification includes a Sequence Listing.

(56) References Cited

OTHER PUBLICATIONS

Cruz-Ramirez et al., "A Bistable Circuit Involving SCARECROW-RETINOBLASTOMA Integrates Cues to Inform Asymmetric Stem Cell Division", Cell, vol. 150, No. 5, pp. 1002-1015, Aug. 2012.
Grundy et al., "The Ku-binding Motif is a Conserved Module for Recruitment and Stimulation of Non-Homologous End-Joining Proteins", Nature Communications, pp. 1-11, 2016.
Gupta et al., "Activities of Human Recombination Protein Rad51", Proceedings of the National Academy of Sciences of the U.S.A., vol. 94, pp. 463-468, Jan. 1997.
Gurushidze et al., "Doubled Haploidy as a Tool for Chimaera Dissolutions of TALEN-Induced Mutations in Barley", Biotechnologies for Plant Mutation Breeding, pp. 129-141, Dec. 2016.
Gurushidze et al., "True-Breeding Targeted Gene Knock-Out in Bariey Using Designer TALE-Nuclease in Haploid Dells", PLOS One, vol. 9, Issue 3, pp. 1-9, Mar. 2014.
Hameed, "Hypoxia up-regulates mitochondrial genome-encoded transcripts in *Arabidopsis* roots", Genes Genet Syst, vol. 90, No. 6, pp. 325-334, Mar. 2016.
International Search Report and Written Opinion for PCT/US2019/014559 dated Apr. 15, 2019.
Kerpen et al., "Hypoxic Conditions in Crown Galls Induce Plant Anaerobic Responses That Support Tumor Proliferation", Frontiers in Plant Science, vol. 10, Issue 56, pp. 1-10, Feb. 2016.
Kono et al., "A Distinct Type of Cyclin D, CYCD4;2, Involved in the Activation of Cell Division in *Arabidopsis*", Plant Cell Reproduction, vol. 25, pp. 540-545, 2006.
Kushwaha et al., "The replication initiator protein of a geminivirus interacts with host monoubiquitination machinery and stimulates transcription of the viral genome", PloS Pathog, vol. 13, No. 8, pp. 1-41, Aug. 2017.
Li et al., "TALEN-Mediated Homologous Recombination Produces Site-Directed DNA Base Change and Herbicide-Resistant Rice", Journal of Genetics and Genomics, vol. 43, pp. 297-305, Mar. 2016.
Lim et al., "Molecular Analysis of the SCARECROW Gene in Maize Reveals a Common Basis for Radial Patterning in Diverse Meristems", The Plant Cell, vol. 12, pp. 1307-1318, Aug. 2000.
Lin et al., "Application of Protoplast Technology to CRISPR/Cas9 Mutagenesis: From Single-Cell Mutation Detection to Mutant Plant Regneration", Plant Biotechnology, vol. 16, pp. 1295-1310, 2018.
Liu et al., "Bean Yellow Dwarf Virus RepA, but Not Rep, Binds to Maize Retinoblastoma Protein, and the Virus Tolerates Mutations in the Consensus Binding Motif", Virology, vol. 256, pp. 270-279, 1999.
Papadakis et al., "Reduced Activity of Antioxidant Machinery Is Correlated with Suppression of Totipotency in Plant Protoplasts", Plant Physiology, vol. 126, pp. 434-444, May 2001.
Prentiss et al., "Structure/Function Relationships in RecA Protein-Mediated Homology Recognition and Strand Exchange", Critical Reviews in Biochemistry and Molecular Biology, vol. 50, No. 6, pp. 453-476, 2015.
Riesenberg et al., "Simultaneous Precise Editing of Multiple Genes in Human Cells", Nucleic Acids Research, pp. 1-10, 2019.
Seybold et al., "CDPK Activation in PRR Signaling", Methods in Molecular Biology, vol. 1578, pp. 173-183, 2017.
White et al., "AAA + ATPases: Achieving Diversity of Function with Conserved Machinery", Traffic, vol. 8, pp. 1657-1667, 2007.
Xie et al., "RNA-Guided Genome Editing in Plants Using a CRISPR-Cas System", Molecular Plant, vol. 6, pp. 1975-1983, 2013.
Yamauchi et al., "Metallothionein genes encoding ROS scavenging enzymes are down-regulated in the root cortex during inducible aerenchyma formation in rice", Plant Dignal Behav., vol. 12, No. 11, pp. 1-4, Oct. 2017.
Ishii, "Factors Influencing Protoplast Viability of Suspension-Cultured Rice Cells during Isolation Process", Plant Physiol., vol. 88, pp. 26-29, 1988.
Karuppanapandian et al., "Reactive Oxygen Species in Plants: Their Generation, Signal Transduction, and Scavenging Mechanisms", Austrialian Journal of Crop Science, vol. 5, Issue 6, pp. 709-725, 2011.
Knight, "Calcium Signaling During Abiotic Stress in Plants", International Review of Cytology, vol. 195, pp. 269-324, 2000.
Liu et al., "Genome-Wide Identification, Phylogeny and Expression Analyses of SCARECROW-LIKE(SCL) Genes in Millet (*Setaria italica*)", Physiology and Molecular Biology of Plants, vol. 23, No. 3, pp. 629-640, 2017.
Pivato et al., "Low-Molecular-Weight Thiols in Plants: Functional and Analytical Implications", Archives of Biochemistry and Biophysics, vol. 560, pp. 83-99, 2014.
Roest et al., "Plant Regeneration from Protoplasts: A Literature Review", Acta. Bot. Neerl., vol. 38, Issue 1, pp. 1-23, Mar. 1989.
Sassa et al., "The Molecular Characterization and in Situ Expression Pattern of Pea SCARECROW Gene", Plant Dell Physiology, vol. 42, No. 4, pp. 385-394, 2001.
White et al., "Calcium in Plants", Annals of Botany, vol. 92, Issue 4, pp. 487-511, Aug. 2003.
Yoo et al., "*Arabidopsis* Mesophyll Protoplasts: A Versatile Cell System for Transient Gene Expression Analysis", Nature Protocol, vol. 2, Issue 7, pp. 1565-1572, Feb. 2007.
International Bureau in connection with PCT/US2019/014559 filed Jan. 22, 2019, "International Preliminary Report on Patentability", 11 pages, dated Aug. 6, 2020.
Lacroix et al., "The roles of bacterial and host plant factors in Agrobacterium-mediated genetic transformation", Int. J. Dev. Biol., vol. 57, pp. 467-481, published 2013.
Bortesi et al., "The CRISPR/Cas9 system for plant genome editing and beyond", Biotechnology Advances, vol. 33, pp. 41-52, Dec. 16, 2014.
Dan, Yinghui, "Biological functions of antioxidants in plant transformation", In Vitro Cell Dev. Biol. Plant, vol. 44, pp. 149-161, 2008.
United States Patent and Trademark Office in connection with U.S. Appl. No. 16/963,372, filed Jul. 20, 2020, "Restriction Requirement", 8 pages, dated Feb. 4, 2022.
United States Patent and Trademark Office in connection with U.S. Appl. No. 15/908,191, filed Feb. 28, 2018, "Final Office Action", 33 pages, dated Feb. 4, 2020.
United States Patent and Trademark Office in connection with U.S. Appl. No. 15/908,191, filed Feb. 28, "Final Office Action", 22 pages, dated Apr. 14, 2021.
United States Patent and Trademark Office in connection with U.S. Appl. No. 15/908,191, filed Feb. 28, 2018, "Non-Final Office Action", 96 pages, dated Mar. 1, 2019.
United States Patent and Trademark Office in connection with U.S. Appl. No. 15/908,191, filed Feb. 28, 2018, "Non-Final Office Action", 19 pages, dated Sep. 28, 2020.

* cited by examiner

_US 11,746,354 B2_

SEQUENCE LISTING

```
<160> NUMBER OF SEQ ID NOS: 6

<210> SEQ ID NO 1
<211> LENGTH: 1307
<212> TYPE: PRT
<213> ORGANISM: Unknown
<220> FEATURE:
<223> OTHER INFORMATION: A bacterium in the genus Acidaminococcus

<400> SEQUENCE: 1

Met Thr Gln Phe Glu Gly Phe Thr Asn Leu Tyr Gln Val Ser Lys Thr
1               5                   10                  15

Leu Arg Phe Glu Leu Ile Pro Gln Gly Lys Thr Leu Lys His Ile Gln
            20                  25                  30

Glu Gln Gly Phe Ile Glu Glu Asp Lys Ala Arg Asn Asp His Tyr Lys
        35                  40                  45

Glu Leu Lys Pro Ile Ile Asp Arg Ile Tyr Lys Thr Tyr Ala Asp Gln
    50                  55                  60

Cys Leu Gln Leu Val Gln Leu Asp Trp Glu Asn Leu Ser Ala Ala Ile
65                  70                  75                  80

Asp Ser Tyr Arg Lys Glu Lys Thr Glu Glu Thr Arg Asn Ala Leu Ile
                85                  90                  95

Glu Glu Gln Ala Thr Tyr Arg Asn Ala Ile His Asp Tyr Phe Ile Gly
            100                 105                 110

Arg Thr Asp Asn Leu Thr Asp Ala Ile Asn Lys Arg His Ala Glu Ile
```

```
                  115                 120                 125
Tyr Lys Gly Leu Phe Lys Ala Glu Leu Phe Asn Gly Lys Val Leu Lys
    130                 135                 140

Gln Leu Gly Thr Val Thr Thr Thr Glu His Glu Asn Ala Leu Leu Arg
145                 150                 155                 160

Ser Phe Asp Lys Phe Thr Thr Tyr Phe Ser Gly Phe Tyr Glu Asn Arg
                165                 170                 175

Lys Asn Val Phe Ser Ala Glu Asp Ile Ser Thr Ala Ile Pro His Arg
            180                 185                 190

Ile Val Gln Asp Asn Phe Pro Lys Phe Lys Glu Asn Cys His Ile Phe
        195                 200                 205

Thr Arg Leu Ile Thr Ala Val Pro Ser Leu Arg Glu His Phe Glu Asn
    210                 215                 220

Val Lys Lys Ala Ile Gly Ile Phe Val Ser Thr Ser Ile Glu Glu Val
225                 230                 235                 240

Phe Ser Phe Pro Phe Tyr Asn Gln Leu Leu Thr Gln Thr Gln Ile Asp
                245                 250                 255

Leu Tyr Asn Gln Leu Leu Gly Gly Ile Ser Arg Glu Ala Gly Thr Glu
            260                 265                 270

Lys Ile Lys Gly Leu Asn Glu Val Leu Asn Leu Ala Ile Gln Lys Asn
        275                 280                 285

Asp Glu Thr Ala His Ile Ile Ala Ser Leu Pro His Arg Phe Ile Pro
    290                 295                 300

Leu Phe Lys Gln Ile Leu Ser Asp Arg Asn Thr Leu Ser Phe Ile Leu
305                 310                 315                 320

Glu Glu Phe Lys Ser Asp Glu Val Ile Gln Ser Phe Cys Lys Tyr
                325                 330                 335

Lys Thr Leu Leu Arg Asn Glu Asn Val Leu Glu Thr Ala Glu Ala Leu
            340                 345                 350

Phe Asn Glu Leu Asn Ser Ile Asp Leu Thr His Ile Phe Ile Ser His
        355                 360                 365

Lys Lys Leu Glu Thr Ile Ser Ser Ala Leu Cys Asp His Trp Asp Thr
    370                 375                 380

Leu Arg Asn Ala Leu Tyr Glu Arg Arg Ile Ser Glu Leu Thr Gly Lys
385                 390                 395                 400

Ile Thr Lys Ser Ala Lys Glu Lys Val Gln Arg Ser Leu Lys His Glu
                405                 410                 415

Asp Ile Asn Leu Gln Glu Ile Ser Ala Ala Gly Lys Glu Leu Ser
            420                 425                 430

Glu Ala Phe Lys Gln Lys Thr Ser Glu Ile Leu Ser His Ala His Ala
        435                 440                 445

Ala Leu Asp Gln Pro Leu Pro Thr Thr Leu Lys Lys Gln Glu Glu Lys
    450                 455                 460

Glu Ile Leu Lys Ser Gln Leu Asp Ser Leu Leu Gly Leu Tyr His Leu
465                 470                 475                 480

Leu Asp Trp Phe Ala Val Asp Glu Ser Asn Glu Val Asp Pro Glu Phe
                485                 490                 495

Ser Ala Arg Leu Thr Gly Ile Lys Leu Glu Met Glu Pro Ser Leu Ser
            500                 505                 510

Phe Tyr Asn Lys Ala Arg Asn Tyr Ala Thr Lys Lys Pro Tyr Ser Val
        515                 520                 525

Glu Lys Phe Lys Leu Asn Phe Gln Met Pro Thr Leu Ala Ser Gly Trp
    530                 535                 540
```

```
Asp Val Asn Lys Glu Lys Asn Gly Ala Ile Leu Phe Val Lys Asn
545                 550                 555                 560

Gly Leu Tyr Tyr Leu Gly Ile Met Pro Lys Gln Lys Gly Arg Tyr Lys
                565                 570                 575

Ala Leu Ser Phe Glu Pro Thr Glu Lys Thr Ser Glu Gly Phe Asp Lys
            580                 585                 590

Met Tyr Tyr Asp Tyr Phe Pro Asp Ala Ala Lys Met Ile Pro Lys Cys
        595                 600                 605

Ser Thr Gln Leu Lys Ala Val Thr Ala His Phe Gln Thr His Thr Thr
    610                 615                 620

Pro Ile Leu Leu Ser Asn Asn Phe Ile Glu Pro Leu Glu Ile Thr Lys
625                 630                 635                 640

Glu Ile Tyr Asp Leu Asn Asn Pro Glu Lys Glu Pro Lys Lys Phe Gln
                645                 650                 655

Thr Ala Tyr Ala Lys Lys Thr Gly Asp Gln Lys Gly Tyr Arg Glu Ala
            660                 665                 670

Leu Cys Lys Trp Ile Asp Phe Thr Arg Asp Phe Leu Ser Lys Tyr Thr
        675                 680                 685

Lys Thr Thr Ser Ile Asp Leu Ser Ser Leu Arg Pro Ser Ser Gln Tyr
    690                 695                 700

Lys Asp Leu Gly Glu Tyr Tyr Ala Glu Leu Asn Pro Leu Leu Tyr His
705                 710                 715                 720

Ile Ser Phe Gln Arg Ile Ala Glu Lys Glu Ile Met Asp Ala Val Glu
                725                 730                 735

Thr Gly Lys Leu Tyr Leu Phe Gln Ile Tyr Asn Lys Asp Phe Ala Lys
            740                 745                 750

Gly His His Gly Lys Pro Asn Leu His Thr Leu Tyr Trp Thr Gly Leu
        755                 760                 765

Phe Ser Pro Glu Asn Leu Ala Lys Thr Ser Ile Lys Leu Asn Gly Gln
    770                 775                 780

Ala Glu Leu Phe Tyr Arg Pro Lys Ser Arg Met Lys Arg Met Ala His
785                 790                 795                 800

Arg Leu Gly Glu Lys Met Leu Asn Lys Lys Leu Lys Asp Gln Lys Thr
                805                 810                 815

Pro Ile Pro Asp Thr Leu Tyr Gln Glu Leu Tyr Asp Tyr Val Asn His
            820                 825                 830

Arg Leu Ser His Asp Leu Ser Asp Glu Ala Arg Ala Leu Leu Pro Asn
        835                 840                 845

Val Ile Thr Lys Glu Val Ser His Glu Ile Ile Lys Asp Arg Arg Phe
    850                 855                 860

Thr Ser Asp Lys Phe Phe Phe His Val Pro Ile Thr Leu Asn Tyr Gln
865                 870                 875                 880

Ala Ala Asn Ser Pro Ser Lys Phe Asn Gln Arg Val Asn Ala Tyr Leu
                885                 890                 895

Lys Glu His Pro Glu Thr Pro Ile Ile Gly Ile Asp Arg Gly Glu Arg
            900                 905                 910

Asn Leu Ile Tyr Ile Thr Val Ile Asp Ser Thr Gly Lys Ile Leu Glu
        915                 920                 925

Gln Arg Ser Leu Asn Thr Ile Gln Gln Phe Asp Tyr Gln Lys Lys Leu
    930                 935                 940

Asp Asn Arg Glu Lys Glu Arg Val Ala Ala Arg Gln Ala Trp Ser Val
945                 950                 955                 960
```

Val Gly Thr Ile Lys Asp Leu Lys Gln Gly Tyr Leu Ser Gln Val Ile
            965                 970                 975

His Glu Ile Val Asp Leu Met Ile His Tyr Gln Ala Val Val Leu
        980                 985                 990

Glu Asn Leu Asn Phe Gly Phe Lys Ser Lys Arg Thr Gly Ile Ala Glu
        995                1000                1005

Lys Ala Val Tyr Gln Gln Phe Glu Lys Met Leu Ile Asp Lys Leu
    1010                1015                1020

Asn Cys Leu Val Leu Lys Asp Tyr Pro Ala Glu Lys Val Gly Gly
    1025                1030                1035

Val Leu Asn Pro Tyr Gln Leu Thr Asp Gln Phe Thr Ser Phe Ala
    1040                1045                1050

Lys Met Gly Thr Gln Ser Gly Phe Leu Phe Tyr Val Pro Ala Pro
    1055                1060                1065

Tyr Thr Ser Lys Ile Asp Pro Leu Thr Gly Phe Val Asp Pro Phe
    1070                1075                1080

Val Trp Lys Thr Ile Lys Asn His Glu Ser Arg Lys His Phe Leu
    1085                1090                1095

Glu Gly Phe Asp Phe Leu His Tyr Asp Val Lys Thr Gly Asp Phe
    1100                1105                1110

Ile Leu His Phe Lys Met Asn Arg Asn Leu Ser Phe Gln Arg Gly
    1115                1120                1125

Leu Pro Gly Phe Met Pro Ala Trp Asp Ile Val Phe Glu Lys Asn
    1130                1135                1140

Glu Thr Gln Phe Asp Ala Lys Gly Thr Pro Phe Ile Ala Gly Lys
    1145                1150                1155

Arg Ile Val Pro Val Ile Glu Asn His Arg Phe Thr Gly Arg Tyr
    1160                1165                1170

Arg Asp Leu Tyr Pro Ala Asn Glu Leu Ile Ala Leu Leu Glu Glu
    1175                1180                1185

Lys Gly Ile Val Phe Arg Asp Gly Ser Asn Ile Leu Pro Lys Leu
    1190                1195                1200

Leu Glu Asn Asp Asp Ser His Ala Ile Asp Thr Met Val Ala Leu
    1205                1210                1215

Ile Arg Ser Val Leu Gln Met Arg Asn Ser Asn Ala Ala Thr Gly
    1220                1225                1230

Glu Asp Tyr Ile Asn Ser Pro Val Arg Asp Leu Asn Gly Val Cys
    1235                1240                1245

Phe Asp Ser Arg Phe Gln Asn Pro Glu Trp Pro Met Asp Ala Asp
    1250                1255                1260

Ala Asn Gly Ala Tyr His Ile Ala Leu Lys Gly Gln Leu Leu Leu
    1265                1270                1275

Asn His Leu Lys Glu Ser Lys Asp Leu Lys Leu Gln Asn Gly Ile
    1280                1285                1290

Ser Asn Gln Asp Trp Leu Ala Tyr Ile Gln Glu Leu Arg Asn
    1295                1300                1305

<210> SEQ ID NO 2
<211> LENGTH: 1228
<212> TYPE: PRT
<213> ORGANISM: Unknown
<220> FEATURE:
<223> OTHER INFORMATION: A bacterium in the genus Lachnospiraceae

<400> SEQUENCE: 2

```
Met Ser Lys Leu Glu Lys Phe Thr Asn Cys Tyr Ser Leu Ser Lys Thr
1               5                   10                  15
Leu Arg Phe Lys Ala Ile Pro Val Gly Lys Thr Gln Glu Asn Ile Asp
            20                  25                  30
Asn Lys Arg Leu Leu Val Glu Asp Glu Lys Arg Ala Glu Asp Tyr Lys
        35                  40                  45
Gly Val Lys Lys Leu Leu Asp Arg Tyr Tyr Leu Ser Phe Ile Asn Asp
    50                  55                  60
Val Leu His Ser Ile Lys Leu Lys Asn Leu Asn Asn Tyr Ile Ser Leu
65                  70                  75                  80
Phe Arg Lys Lys Thr Arg Thr Glu Lys Glu Asn Lys Glu Leu Glu Asn
                85                  90                  95
Leu Glu Ile Asn Leu Arg Lys Glu Ile Ala Lys Ala Phe Lys Gly Asn
            100                 105                 110
Glu Gly Tyr Lys Ser Leu Phe Lys Lys Asp Ile Ile Glu Thr Ile Leu
        115                 120                 125
Pro Glu Phe Leu Asp Asp Lys Asp Glu Ile Ala Leu Val Asn Ser Phe
    130                 135                 140
Asn Gly Phe Thr Thr Ala Phe Thr Gly Phe Phe Asp Asn Arg Glu Asn
145                 150                 155                 160
Met Phe Ser Glu Glu Ala Lys Ser Thr Ser Ile Ala Phe Arg Cys Ile
                165                 170                 175
Asn Glu Asn Leu Thr Arg Tyr Ile Ser Asn Met Asp Ile Phe Glu Lys
            180                 185                 190
Val Asp Ala Ile Phe Asp Lys His Glu Val Gln Glu Ile Lys Glu Lys
        195                 200                 205
Ile Leu Asn Ser Asp Tyr Asp Val Glu Asp Phe Phe Glu Gly Glu Phe
    210                 215                 220
Phe Asn Phe Val Leu Thr Gln Glu Gly Ile Asp Val Tyr Asn Ala Ile
225                 230                 235                 240
Ile Gly Gly Phe Val Thr Glu Ser Gly Glu Lys Ile Lys Gly Leu Asn
                245                 250                 255
Glu Tyr Ile Asn Leu Tyr Asn Gln Lys Thr Lys Gln Lys Leu Pro Lys
            260                 265                 270
Phe Lys Pro Leu Tyr Lys Gln Val Leu Ser Asp Arg Glu Ser Leu Ser
        275                 280                 285
Phe Tyr Gly Glu Gly Tyr Thr Ser Asp Glu Glu Val Leu Glu Val Phe
    290                 295                 300
Arg Asn Thr Leu Asn Lys Asn Ser Glu Ile Phe Ser Ser Ile Lys Lys
305                 310                 315                 320
Leu Glu Lys Leu Phe Lys Asn Phe Asp Glu Tyr Ser Ser Ala Gly Ile
                325                 330                 335
Phe Val Lys Asn Gly Pro Ala Ile Ser Thr Ile Ser Lys Asp Ile Phe
            340                 345                 350
Gly Glu Trp Asn Val Ile Arg Asp Lys Trp Asn Ala Glu Tyr Asp Asp
        355                 360                 365
Ile His Leu Lys Lys Lys Ala Val Val Thr Glu Lys Tyr Glu Asp Asp
    370                 375                 380
Arg Arg Lys Ser Phe Lys Lys Ile Gly Ser Phe Ser Leu Glu Gln Leu
385                 390                 395                 400
Gln Glu Tyr Ala Asp Ala Asp Leu Ser Val Val Glu Lys Leu Lys Glu
                405                 410                 415
Ile Ile Ile Gln Lys Val Asp Glu Ile Tyr Lys Val Tyr Gly Ser Ser
```

```
                420              425              430
Glu Lys Leu Phe Asp Ala Asp Phe Val Leu Glu Lys Ser Leu Lys Lys
            435              440              445

Asn Asp Ala Val Val Ala Ile Met Lys Asp Leu Leu Asp Ser Val Lys
450              455              460

Ser Phe Glu Asn Tyr Ile Lys Ala Phe Phe Gly Glu Gly Lys Glu Thr
465              470              475              480

Asn Arg Asp Glu Ser Phe Tyr Gly Asp Phe Val Leu Ala Tyr Asp Ile
            485              490              495

Leu Leu Lys Val Asp His Ile Tyr Asp Ala Ile Arg Asn Tyr Val Thr
            500              505              510

Gln Lys Pro Tyr Ser Lys Asp Lys Phe Lys Leu Tyr Phe Gln Asn Pro
        515              520              525

Gln Phe Met Gly Gly Trp Asp Lys Asp Lys Glu Thr Asp Tyr Arg Ala
        530              535              540

Thr Ile Leu Arg Tyr Gly Ser Lys Tyr Leu Ala Ile Met Asp Lys Lys
545              550              555              560

Lys Tyr Ala Lys Cys Leu Gln Lys Ile Asp Lys Asp Val Asn Gly
            565              570              575

Asn Tyr Glu Lys Ile Asn Tyr Lys Leu Leu Pro Gly Pro Asn Lys Met
            580              585              590

Leu Pro Lys Val Phe Phe Ser Lys Lys Trp Met Ala Tyr Tyr Asn Pro
        595              600              605

Ser Glu Asp Ile Gln Lys Ile Tyr Lys Asn Gly Thr Phe Lys Lys Gly
        610              615              620

Asp Met Phe Asn Leu Asn Asp Cys His Lys Leu Ile Asp Phe Phe Lys
625              630              635              640

Asp Ser Ile Ser Arg Tyr Pro Lys Trp Ser Asn Ala Tyr Asp Phe Asn
            645              650              655

Phe Ser Glu Thr Glu Lys Tyr Lys Asp Ile Ala Gly Phe Tyr Arg Glu
            660              665              670

Val Glu Glu Gln Gly Tyr Lys Val Ser Phe Glu Ser Ala Ser Lys Lys
        675              680              685

Glu Val Asp Lys Leu Val Glu Glu Gly Lys Leu Tyr Met Phe Gln Ile
        690              695              700

Tyr Asn Lys Asp Phe Ser Asp Lys Ser His Gly Thr Pro Asn Leu His
705              710              715              720

Thr Met Tyr Phe Lys Leu Leu Phe Asp Glu Asn Asn His Gly Gln Ile
            725              730              735

Arg Leu Ser Gly Gly Ala Glu Leu Phe Met Arg Arg Ala Ser Leu Lys
            740              745              750

Lys Glu Glu Leu Val Val His Pro Ala Asn Ser Pro Ile Ala Asn Lys
        755              760              765

Asn Pro Asp Asn Pro Lys Lys Thr Thr Thr Leu Ser Tyr Asp Val Tyr
        770              775              780

Lys Asp Lys Arg Phe Ser Glu Asp Gln Tyr Glu Leu His Ile Pro Ile
785              790              795              800

Ala Ile Asn Lys Cys Pro Lys Asn Ile Phe Lys Ile Asn Thr Glu Val
            805              810              815

Arg Val Leu Leu Lys His Asp Asp Asn Pro Tyr Val Ile Gly Ile Asp
            820              825              830

Arg Gly Glu Arg Asn Leu Leu Tyr Ile Val Val Val Asp Gly Lys Gly
        835              840              845
```

```
Asn Ile Val Glu Gln Tyr Ser Leu Asn Glu Ile Ile Asn Asn Phe Asn
850                 855                 860

Gly Ile Arg Ile Lys Thr Asp Tyr His Ser Leu Leu Asp Lys Lys Glu
865                 870                 875                 880

Lys Glu Arg Phe Glu Ala Arg Gln Asn Trp Thr Ser Ile Glu Asn Ile
            885                 890                 895

Lys Glu Leu Lys Ala Gly Tyr Ile Ser Gln Val Val His Lys Ile Cys
            900                 905                 910

Glu Leu Val Glu Lys Tyr Asp Ala Val Ile Ala Leu Glu Asp Leu Asn
        915                 920                 925

Ser Gly Phe Lys Asn Ser Arg Val Lys Val Lys Gln Val Tyr Gln
    930                 935                 940

Lys Phe Glu Lys Met Leu Ile Asp Lys Leu Asn Tyr Met Val Asp Lys
945                 950                 955                 960

Lys Ser Asn Pro Cys Ala Thr Gly Gly Ala Leu Lys Gly Tyr Gln Ile
            965                 970                 975

Thr Asn Lys Phe Glu Ser Phe Lys Ser Met Ser Thr Gln Asn Gly Phe
            980                 985                 990

Ile Phe Tyr Ile Pro Ala Trp Leu Thr Ser Lys Ile Asp Pro Ser Thr
        995                 1000                1005

Gly Phe Val Asn Leu Leu Lys Thr Lys Tyr Thr Ser Ile Ala Asp
    1010                1015                1020

Ser Lys Lys Phe Ile Ser Ser Phe Asp Arg Ile Met Tyr Val Pro
    1025                1030                1035

Glu Glu Asp Leu Phe Glu Phe Ala Leu Asp Tyr Lys Asn Phe Ser
    1040                1045                1050

Arg Thr Asp Ala Asp Tyr Ile Lys Lys Trp Lys Leu Tyr Ser Tyr
    1055                1060                1065

Gly Asn Arg Ile Arg Ile Phe Arg Asn Pro Lys Lys Asn Asn Val
    1070                1075                1080

Phe Asp Trp Glu Glu Val Cys Leu Thr Ser Ala Tyr Lys Glu Leu
    1085                1090                1095

Phe Asn Lys Tyr Gly Ile Asn Tyr Gln Gln Gly Asp Ile Arg Ala
    1100                1105                1110

Leu Leu Cys Glu Gln Ser Asp Lys Ala Phe Tyr Ser Ser Phe Met
    1115                1120                1125

Ala Leu Met Ser Leu Met Leu Gln Met Arg Asn Ser Ile Thr Gly
    1130                1135                1140

Arg Thr Asp Val Asp Phe Leu Ile Ser Pro Val Lys Asn Ser Asp
    1145                1150                1155

Gly Ile Phe Tyr Asp Ser Arg Asn Tyr Glu Ala Gln Glu Asn Ala
    1160                1165                1170

Ile Leu Pro Lys Asn Ala Asp Ala Asn Gly Ala Tyr Asn Ile Ala
    1175                1180                1185

Arg Lys Val Leu Trp Ala Ile Gly Gln Phe Lys Lys Ala Glu Asp
    1190                1195                1200

Glu Lys Leu Asp Lys Val Lys Ile Ala Ile Ser Asn Lys Glu Trp
    1205                1210                1215

Leu Glu Tyr Ala Gln Thr Ser Val Lys His
    1220                1225

<210> SEQ ID NO 3
<211> LENGTH: 1300
```

<212> TYPE: PRT
<213> ORGANISM: Francisella novicida

<400> SEQUENCE: 3

```
Met Ser Ile Tyr Gln Glu Phe Val Asn Lys Tyr Ser Leu Ser Lys Thr
1               5                   10                  15

Leu Arg Phe Glu Leu Ile Pro Gln Gly Lys Thr Leu Glu Asn Ile Lys
            20                  25                  30

Ala Arg Gly Leu Ile Leu Asp Asp Glu Lys Arg Ala Lys Asp Tyr Lys
        35                  40                  45

Lys Ala Lys Gln Ile Ile Asp Lys Tyr His Gln Phe Phe Ile Glu Glu
    50                  55                  60

Ile Leu Ser Ser Val Cys Ile Ser Glu Asp Leu Leu Gln Asn Tyr Ser
65                  70                  75                  80

Asp Val Tyr Phe Lys Leu Lys Lys Ser Asp Asp Asn Leu Gln Lys
                85                  90                  95

Asp Phe Lys Ser Ala Lys Asp Thr Ile Lys Lys Gln Ile Ser Glu Tyr
            100                 105                 110

Ile Lys Asp Ser Glu Lys Phe Lys Asn Leu Phe Asn Gln Asn Leu Ile
        115                 120                 125

Asp Ala Lys Lys Gly Gln Glu Ser Asp Leu Ile Leu Trp Leu Lys Gln
    130                 135                 140

Ser Lys Asp Asn Gly Ile Glu Leu Phe Lys Ala Asn Ser Asp Ile Thr
145                 150                 155                 160

Asp Ile Asp Glu Ala Leu Glu Ile Ile Lys Ser Phe Lys Gly Trp Thr
                165                 170                 175

Thr Tyr Phe Lys Gly Phe His Glu Asn Arg Lys Asn Val Tyr Ser Ser
            180                 185                 190

Asn Asp Ile Pro Thr Ser Ile Ile Tyr Arg Ile Val Asp Asp Asn Leu
        195                 200                 205

Pro Lys Phe Leu Glu Asn Lys Ala Lys Tyr Glu Ser Leu Lys Asp Lys
    210                 215                 220

Ala Pro Glu Ala Ile Asn Tyr Glu Gln Ile Lys Lys Asp Leu Ala Glu
225                 230                 235                 240

Glu Leu Thr Phe Asp Ile Asp Tyr Lys Thr Ser Glu Val Asn Gln Arg
                245                 250                 255

Val Phe Ser Leu Asp Glu Val Phe Glu Ile Ala Asn Phe Asn Asn Tyr
            260                 265                 270

Leu Asn Gln Ser Gly Ile Thr Lys Phe Asn Thr Ile Ile Gly Gly Lys
        275                 280                 285

Phe Val Asn Gly Glu Asn Thr Lys Arg Lys Gly Ile Asn Glu Tyr Ile
    290                 295                 300

Asn Leu Tyr Ser Gln Gln Ile Asn Asp Lys Thr Leu Lys Lys Tyr Lys
305                 310                 315                 320

Met Ser Val Leu Phe Lys Gln Ile Leu Ser Asp Thr Glu Ser Lys Ser
                325                 330                 335

Phe Val Ile Asp Lys Leu Glu Asp Asp Ser Asp Val Val Thr Thr Met
            340                 345                 350

Gln Ser Phe Tyr Glu Gln Ile Ala Ala Phe Lys Thr Val Glu Glu Lys
        355                 360                 365

Ser Ile Lys Glu Thr Leu Ser Leu Leu Phe Asp Asp Leu Lys Ala Gln
    370                 375                 380

Lys Leu Asp Leu Ser Lys Ile Tyr Phe Lys Asn Asp Lys Ser Leu Thr
385                 390                 395                 400
```

```
Asp Leu Ser Gln Gln Val Phe Asp Asp Tyr Ser Val Ile Gly Thr Ala
                405                 410                 415

Val Leu Glu Tyr Ile Thr Gln Gln Ile Ala Pro Lys Asn Leu Asp Asn
            420                 425                 430

Pro Ser Lys Lys Glu Gln Glu Leu Ile Ala Lys Lys Thr Glu Lys Ala
        435                 440                 445

Lys Tyr Leu Ser Leu Glu Thr Ile Lys Leu Ala Leu Glu Glu Phe Asn
    450                 455                 460

Lys His Arg Asp Ile Asp Lys Gln Cys Arg Phe Glu Glu Ile Leu Ala
465                 470                 475                 480

Asn Phe Ala Ala Ile Pro Met Ile Phe Asp Glu Ile Ala Gln Asn Lys
                485                 490                 495

Asp Asn Leu Ala Gln Ile Ser Ile Lys Tyr Gln Asn Gln Gly Lys Lys
            500                 505                 510

Asp Leu Leu Gln Ala Ser Ala Glu Asp Val Lys Ala Ile Lys Asp
        515                 520                 525

Leu Leu Asp Gln Thr Asn Asn Leu Leu His Lys Leu Lys Ile Phe His
    530                 535                 540

Ile Ser Gln Ser Glu Asp Lys Ala Asn Ile Leu Asp Lys Asp Glu His
545                 550                 555                 560

Phe Tyr Leu Val Phe Glu Glu Cys Tyr Phe Glu Leu Ala Asn Ile Val
                565                 570                 575

Pro Leu Tyr Asn Lys Ile Arg Asn Tyr Ile Thr Gln Lys Pro Tyr Ser
            580                 585                 590

Asp Glu Lys Phe Lys Leu Asn Phe Glu Asn Ser Thr Leu Ala Asn Gly
        595                 600                 605

Trp Asp Lys Asn Lys Glu Pro Asp Asn Thr Ala Ile Leu Phe Ile Lys
    610                 615                 620

Asp Asp Lys Tyr Tyr Leu Gly Val Met Asn Lys Lys Asn Asn Lys Ile
625                 630                 635                 640

Phe Asp Asp Lys Ala Ile Lys Glu Asn Lys Gly Glu Gly Tyr Lys Lys
                645                 650                 655

Ile Val Tyr Lys Leu Leu Pro Gly Ala Asn Lys Met Leu Pro Lys Val
            660                 665                 670

Phe Phe Ser Ala Lys Ser Ile Lys Phe Tyr Asn Pro Ser Glu Asp Ile
        675                 680                 685

Leu Arg Ile Arg Asn His Ser Thr His Thr Lys Asn Gly Ser Pro Gln
    690                 695                 700

Lys Gly Tyr Glu Lys Phe Glu Phe Asn Ile Glu Asp Cys Arg Lys Phe
705                 710                 715                 720

Ile Asp Phe Tyr Lys Gln Ser Ile Ser Lys His Pro Glu Trp Lys Asp
                725                 730                 735

Phe Gly Phe Arg Phe Ser Asp Thr Gln Arg Tyr Asn Ser Ile Asp Glu
            740                 745                 750

Phe Tyr Arg Glu Val Glu Asn Gln Gly Tyr Lys Leu Thr Phe Glu Asn
        755                 760                 765

Ile Ser Glu Ser Tyr Ile Asp Ser Val Val Asn Gln Gly Lys Leu Tyr
    770                 775                 780

Leu Phe Gln Ile Tyr Asn Lys Asp Phe Ser Ala Tyr Ser Lys Gly Arg
785                 790                 795                 800

Pro Asn Leu His Thr Leu Tyr Trp Lys Ala Leu Phe Asp Glu Arg Asn
                805                 810                 815
```

Leu Gln Asp Val Val Tyr Lys Leu Asn Gly Glu Ala Glu Leu Phe Tyr
        820                 825                 830

Arg Lys Gln Ser Ile Pro Lys Lys Ile Thr His Pro Ala Lys Glu Ala
        835                 840                 845

Ile Ala Asn Lys Asn Lys Asp Asn Pro Lys Lys Glu Ser Val Phe Glu
        850                 855                 860

Tyr Asp Leu Ile Lys Asp Lys Arg Phe Thr Glu Asp Lys Phe Phe Phe
865                 870                 875                 880

His Cys Pro Ile Thr Ile Asn Phe Lys Ser Ser Gly Ala Asn Lys Phe
                885                 890                 895

Asn Asp Glu Ile Asn Leu Leu Leu Lys Glu Lys Ala Asn Asp Val His
        900                 905                 910

Ile Leu Ser Ile Asp Arg Gly Glu Arg His Leu Ala Tyr Tyr Thr Leu
        915                 920                 925

Val Asp Gly Lys Gly Asn Ile Ile Lys Gln Asp Thr Phe Asn Ile Ile
        930                 935                 940

Gly Asn Asp Arg Met Lys Thr Asn Tyr His Asp Lys Leu Ala Ala Ile
945                 950                 955                 960

Glu Lys Asp Arg Asp Ser Ala Arg Lys Asp Trp Lys Lys Ile Asn Asn
                965                 970                 975

Ile Lys Glu Met Lys Glu Gly Tyr Leu Ser Gln Val Val His Glu Ile
        980                 985                 990

Ala Lys Leu Val Ile Glu Tyr Asn Ala Ile Val Val Phe Glu Asp Leu
        995                 1000                1005

Asn Phe Gly Phe Lys Arg Gly Arg Phe Lys Val Glu Lys Gln Val
        1010                1015                1020

Tyr Gln Lys Leu Glu Lys Met Leu Ile Glu Lys Leu Asn Tyr Leu
        1025                1030                1035

Val Phe Lys Asp Asn Glu Phe Asp Lys Thr Gly Gly Val Leu Arg
        1040                1045                1050

Ala Tyr Gln Leu Thr Ala Pro Phe Glu Thr Phe Lys Lys Met Gly
        1055                1060                1065

Lys Gln Thr Gly Ile Ile Tyr Tyr Val Pro Ala Gly Phe Thr Ser
        1070                1075                1080

Lys Ile Cys Pro Val Thr Gly Phe Val Asn Gln Leu Tyr Pro Lys
        1085                1090                1095

Tyr Glu Ser Val Ser Lys Ser Gln Glu Phe Phe Ser Lys Phe Asp
        1100                1105                1110

Lys Ile Cys Tyr Asn Leu Asp Lys Gly Tyr Phe Glu Phe Ser Phe
        1115                1120                1125

Asp Tyr Lys Asn Phe Gly Asp Lys Ala Ala Lys Gly Lys Trp Thr
        1130                1135                1140

Ile Ala Ser Phe Gly Ser Arg Leu Ile Asn Phe Arg Asn Ser Asp
        1145                1150                1155

Lys Asn His Asn Trp Asp Thr Arg Glu Val Tyr Pro Thr Lys Glu
        1160                1165                1170

Leu Glu Lys Leu Leu Lys Asp Tyr Ser Ile Glu Tyr Gly His Gly
        1175                1180                1185

Glu Cys Ile Lys Ala Ala Ile Cys Gly Glu Ser Asp Lys Lys Phe
        1190                1195                1200

Phe Ala Lys Leu Thr Ser Val Leu Asn Thr Ile Leu Gln Met Arg
        1205                1210                1215

Asn Ser Lys Thr Gly Thr Glu Leu Asp Tyr Leu Ile Ser Pro Val

```
                1220                1225                1230
Ala Asp Val Asn Gly Asn Phe Phe Asp Ser Arg Gln Ala Pro Lys
    1235                1240                1245

Asn Met Pro Gln Asp Ala Asp Ala Asn Gly Ala Tyr His Ile Gly
    1250                1255                1260

Leu Lys Gly Leu Met Leu Leu Gly Arg Ile Lys Asn Asn Gln Glu
    1265                1270                1275

Gly Lys Lys Leu Asn Leu Val Ile Lys Asn Glu Glu Tyr Phe Glu
    1280                1285                1290

Phe Val Gln Asn Arg Asn Asn
    1295                1300

<210> SEQ ID NO 4
<211> LENGTH: 1320
<212> TYPE: PRT
<213> ORGANISM: Unknown
<220> FEATURE:
<223> OTHER INFORMATION: bacterial

<400> SEQUENCE: 4

Met Gln Gln Tyr Gln Val Ser Lys Thr Val Arg Phe Gly Leu Thr Leu
1               5                   10                  15

Lys Asn Ser Glu Lys Lys His Ala Thr His Leu Leu Leu Lys Asp Leu
            20                  25                  30

Val Asn Val Ser Glu Glu Arg Ile Lys Asn Glu Ile Thr Lys Asp Asp
        35                  40                  45

Lys Asn Gln Ser Glu Leu Ser Phe Phe Asn Glu Val Ile Glu Thr Leu
    50                  55                  60

Asp Leu Met Asp Lys Tyr Ile Lys Asp Trp Glu Asn Cys Phe Tyr Arg
65                  70                  75                  80

Thr Asp Gln Ile Gln Leu Thr Lys Glu Tyr Tyr Lys Val Ile Ala Lys
                85                  90                  95

Lys Ala Cys Phe Asp Trp Phe Trp Thr Asn Asp Arg Gly Met Lys Phe
            100                 105                 110

Pro Thr Ser Ser Ile Ile Ser Phe Asn Ser Leu Lys Ser Ser Asp Lys
        115                 120                 125

Ser Lys Thr Ser Asp Asn Leu Asp Arg Lys Lys Ile Leu Asp Tyr
    130                 135                 140

Trp Lys Gly Asn Ile Phe Lys Thr Gln Lys Ala Ile Lys Asp Val Leu
145                 150                 155                 160

Asp Ile Thr Glu Asp Ile Gln Lys Ala Ile Glu Glu Lys Lys Ser His
                165                 170                 175

Arg Glu Ile Asn Arg Val Asn His Arg Lys Met Gly Ile His Leu Ile
            180                 185                 190

His Leu Ile Asn Asp Thr Leu Val Pro Leu Cys Asn Gly Ser Ile Phe
        195                 200                 205

Phe Gly Asn Ile Ser Lys Leu Asp Phe Cys Ser Glu Asn Glu Lys
    210                 215                 220

Leu Ile Asp Phe Ala Ser Thr Glu Lys Gln Asp Glu Arg Lys Phe Leu
225                 230                 235                 240

Leu Ser Lys Ile Asn Glu Ile Lys Gln Tyr Phe Glu Asp Asn Gly Gly
                245                 250                 255

Asn Val Pro Phe Ala Arg Ala Thr Leu Asn Arg His Thr Ala Asn Gln
            260                 265                 270

Lys Pro Asp Arg Tyr Asn Glu Glu Ile Lys Lys Leu Val Asn Glu Leu
```

-continued

```
            275                 280                 285
Gly Val Asn Ser Leu Val Arg Ser Leu Lys Ser Lys Thr Ile Glu Glu
290                 295                 300

Ile Lys Thr His Phe Glu Phe Glu Asn Lys Asn Lys Ile Asn Glu Leu
305                 310                 315                 320

Lys Asn Ser Phe Val Leu Ser Ile Val Glu Lys Ile Gln Leu Phe Lys
                    325                 330                 335

Tyr Lys Thr Ile Pro Ala Ser Val Arg Phe Leu Leu Ala Asp Tyr Phe
                340                 345                 350

Glu Glu Gln Lys Leu Ser Thr Lys Glu Glu Ala Leu Thr Ile Phe Glu
            355                 360                 365

Glu Ile Gly Lys Pro Gln Asn Ile Gly Phe Asp Tyr Ile Gln Leu Lys
        370                 375                 380

Glu Lys Asp Asn Phe Thr Leu Lys Lys Tyr Pro Leu Lys Gln Ala Phe
385                 390                 395                 400

Asp Tyr Ala Trp Glu Asn Leu Ala Arg Leu Asp Gln Asn Pro Lys Ala
                    405                 410                 415

Asn Gln Phe Ser Val Asp Glu Cys Lys Arg Phe Phe Lys Glu Val Phe
                420                 425                 430

Ser Met Glu Met Asp Asn Ile Asn Phe Lys Thr Tyr Ala Leu Leu Leu
            435                 440                 445

Ala Leu Lys Glu Lys Thr Thr Ala Phe Asp Lys Lys Gly Glu Gly Ala
        450                 455                 460

Ala Lys Asn Lys Ser Glu Ile Ile Glu Gln Ile Lys Gly Val Phe Glu
465                 470                 475                 480

Glu Leu Asp Gln Pro Phe Lys Ile Ile Ala Asn Thr Leu Arg Glu Glu
                    485                 490                 495

Val Ile Lys Lys Glu Asp Glu Leu Asn Val Leu Lys Arg Gln Tyr Arg
                500                 505                 510

Glu Thr Asp Arg Lys Ile Lys Thr Leu Gln Asn Glu Ile Lys Lys Ile
            515                 520                 525

Lys Asn Gln Ile Lys Asn Leu Glu Asn Ser Lys Lys Tyr Ser Phe Pro
        530                 535                 540

Glu Ile Ile Lys Trp Ile Asp Leu Thr Glu Gln Gln Leu Leu Asp
545                 550                 555                 560

Lys Asn Lys Gln Ala Lys Ser Asn Tyr Gln Lys Ala Lys Gly Asp Leu
                    565                 570                 575

Gly Leu Ile Arg Gly Ser Gln Lys Thr Ser Ile Asn Asp Tyr Phe Tyr
                580                 585                 590

Leu Thr Asp Lys Val Tyr Arg Lys Leu Ala Gln Asp Phe Gly Lys Lys
            595                 600                 605

Met Ala Asp Leu Arg Glu Lys Leu Leu Asp Lys Asn Asp Val Asn Lys
        610                 615                 620

Ile Lys Tyr Leu Ser Tyr Ile Val Lys Asp Asn Gln Gly Tyr Gln Tyr
625                 630                 635                 640

Thr Leu Leu Lys Pro Leu Glu Asp Lys Asn Ala Glu Ile Ile Glu Leu
                    645                 650                 655

Lys Ser Glu Pro Asn Gly Asp Leu Lys Leu Phe Glu Ile Lys Ser Leu
                660                 665                 670

Thr Ser Lys Thr Leu Asn Lys Phe Ile Lys Asn Lys Gly Ala Tyr Lys
            675                 680                 685

Glu Phe His Ser Ala Glu Phe Glu His Lys Lys Ile Lys Glu Asp Trp
        690                 695                 700
```

-continued

Lys Asn Tyr Lys Tyr Asn Ser Asp Phe Ile Val Lys Leu Lys Lys Cys
705                 710                 715                 720

Leu Ser His Ser Asp Met Ala Asn Thr Gln Asn Trp Lys Ala Phe Gly
            725                 730                 735

Trp Asp Leu Asp Lys Cys Lys Ser Tyr Glu Thr Ile Glu Lys Glu Ile
            740                 745                 750

Asp Gln Lys Ser Tyr Gln Leu Val Glu Ile Lys Leu Ser Lys Thr Thr
            755                 760                 765

Ile Glu Lys Trp Val Lys Glu Asn Asn Tyr Leu Leu Leu Pro Ile Val
770                 775                 780

Asn Gln Asp Ile Thr Ala Glu Lys Leu Lys Val Asn Thr Asn Gln Phe
785                 790                 795                 800

Thr Lys Asp Trp Gln His Ile Phe Glu Lys Asn Pro Asn His Arg Leu
            805                 810                 815

His Pro Glu Phe Asn Ile Ala Tyr Arg Gln Pro Thr Lys Asp Tyr Ala
            820                 825                 830

Lys Glu Gly Glu Lys Arg Tyr Ser Arg Phe Gln Leu Thr Gly Gln Phe
            835                 840                 845

Met Tyr Glu Tyr Ile Pro Gln Asp Ala Asn Tyr Ile Ser Arg Lys Glu
            850                 855                 860

Gln Ile Thr Leu Phe Asn Asp Lys Glu Gln Lys Ile Gln Val Glu
865                 870                 875                 880

Thr Phe Asn Asn Gln Ile Ala Lys Ile Leu Asn Ala Glu Asp Phe Tyr
            885                 890                 895

Val Ile Gly Ile Asp Arg Gly Ile Thr Gln Leu Ala Thr Leu Cys Val
            900                 905                 910

Leu Asn Lys Asn Gly Val Ile Gln Gly Gly Phe Glu Ile Phe Thr Arg
            915                 920                 925

Glu Phe Asp Tyr Thr Asn Lys Gln Trp Lys His Thr Lys Leu Lys Glu
930                 935                 940

Asn Arg Asn Ile Leu Asp Ile Ser Asn Leu Lys Val Glu Thr Thr Val
945                 950                 955                 960

Asn Gly Glu Lys Val Leu Val Asp Leu Ser Val Lys Thr Tyr Leu
            965                 970                 975

Arg Asp Glu Asn Gly Glu Pro Met Lys Asn Glu Lys Gly Val Ile Leu
            980                 985                 990

Thr Lys Asp Asn Leu Gln Lys Ile Lys Leu Lys Gln Leu Ala Tyr Asp
            995                 1000                1005

Arg Lys Leu Gln Tyr Lys Met Gln His Glu Pro Glu Leu Val Leu
            1010                1015                1020

Ser Phe Leu Asp Arg Leu Glu Asn Lys Glu Gln Ile Pro Asn Leu
            1025                1030                1035

Leu Ala Ser Thr Lys Leu Ile Ser Ala Tyr Lys Glu Gly Thr Ala
            1040                1045                1050

Tyr Ala Asp Ile Asp Ile Glu Gln Phe Trp Asn Ile Leu Gln Thr
            1055                1060                1065

Phe Gln Thr Ile Val Asp Lys Phe Gly Gly Ile Glu Asn Ala Lys
            1070                1075                1080

Lys Thr Met Glu Phe Arg Gln Tyr Thr Glu Leu Asp Ala Ser Phe
            1085                1090                1095

Asp Leu Lys Asn Gly Val Val Ala Asn Met Val Gly Val Val Lys
            1100                1105                1110

```
Phe Ile Met Glu Lys Tyr Asn Tyr Lys Thr Phe Ile Ala Leu Glu
    1115                1120                1125

Asp Leu Thr Phe Ala Phe Gly Gln Ser Ile Asp Gly Ile Asn Gly
    1130                1135                1140

Glu Arg Leu Arg Ser Thr Lys Glu Asp Lys Val Asp Phe Lys
    1145                1150                1155

Glu Gln Glu Asn Ser Thr Leu Ala Gly Leu Gly Thr Tyr His Phe
    1160                1165                1170

Phe Glu Met Gln Leu Leu Lys Lys Leu Ser Lys Thr Gln Ile Gly
    1175                1180                1185

Asn Glu Ile Lys His Phe Val Pro Ala Phe Arg Ser Thr Glu Asn
    1190                1195                1200

Tyr Glu Lys Ile Val Arg Lys Asp Lys Asn Val Lys Ala Lys Ile
    1205                1210                1215

Val Ser Tyr Pro Phe Gly Ile Val Ser Phe Val Asn Pro Arg Asn
    1220                1225                1230

Thr Ser Ile Ser Cys Pro Asn Cys Lys Asn Ala Asn Lys Ser Asn
    1235                1240                1245

Arg Ile Lys Lys Glu Asn Asp Arg Ile Leu Cys Lys His Asn Ile
    1250                1255                1260

Glu Lys Thr Lys Gly Asn Cys Gly Phe Asp Thr Ala Asn Phe Asp
    1265                1270                1275

Glu Asn Lys Leu Arg Ala Glu Asn Lys Gly Lys Asn Phe Lys Tyr
    1280                1285                1290

Ile Ser Ser Gly Asp Ala Asn Ala Ala Tyr Asn Ile Ala Val Lys
    1295                1300                1305

Leu Leu Glu Asp Lys Ile Phe Glu Ile Asn Lys Lys
    1310                1315                1320

<210> SEQ ID NO 5
<211> LENGTH: 477
<212> TYPE: DNA
<213> ORGANISM: Zea mays

<400> SEQUENCE: 5
gggttgttgt gggttgaacc cgtcccaacc atcatcaact cgctagccaa acacacgctt      60
aggggccaaa gcagtgctat aatatgagtg gtggcgctat tatatatagc gtcagagaac     120
ttagatctga tattctgatg aagaaaaaat gactactgac tacgaaagaa gaagaaagga     180
gctatagaga gagaagaggg gtcgtgtagt agtgcttaaa ctgtacatga acagcagtag     240
tgttacagaa gctaaactca accagagctc caccaaagac aaagagggtc tacttccatc     300
accgtcttgc tcggtcactt ggagctctgt ccataaatta aacccatcgt ggcatatctg     360
taggcatcta ccccgtcttc gtcgtccgtt cctcactagc taccaagagg tcgccattat     420
tgccaacata gagtgtacgt ggatgtctat atatatgcct acttgcaccc atatggc       477

<210> SEQ ID NO 6
<211> LENGTH: 1054
<212> TYPE: PRT
<213> ORGANISM: Actinobacillus suis

<400> SEQUENCE: 6

Met Lys Leu Thr Pro Leu Asn Tyr Ile Leu Gly Leu Asp Leu Gly Ile
1               5                   10                  15

Ala Ser Val Gly Trp Ala Val Val Glu Ile Asp Glu Gln Glu Asn Pro
            20                  25                  30
```

```
Leu Gly Leu Ile Asp Val Gly Val Arg Thr Phe Asp Arg Ala Glu Val
            35                  40                  45

Pro Lys Thr Gly Glu Ser Leu Ala Leu Ala Arg Arg Leu Ala Arg Ser
 50                  55                  60

Ala Arg Arg Leu Val Lys Arg Ala Asp Arg Ile Lys Lys Ala Lys
 65                  70                  75                  80

Arg Leu Leu Lys Ala Glu Asn Ile Leu Ser Ala Asp Glu His Leu
                 85                  90                  95

Pro Asn Asp Val Trp Gln Leu Arg Val Lys Gly Leu Asp Gln Lys Leu
                100                 105                 110

Glu Arg Gln Glu Trp Ala Ala Val Leu Leu His Leu Lys His Arg
                115                 120                 125

Gly Tyr Leu Ser Gln Arg Lys Asn Glu Ser Lys Ser Glu Asn Lys Glu
            130                 135                 140

Leu Gly Ala Leu Leu Ser Gly Val Glu Thr Asn His Gln Ile Leu Gln
145                 150                 155                 160

Ser Ala Glu Tyr Arg Thr Pro Ala Glu Ile Ala Val Lys Lys Phe His
                165                 170                 175

Val Glu Asp Gly His Ile Arg Asn Gln Arg Gly Ala Tyr Thr His Thr
                180                 185                 190

Phe Ser Arg Leu Asp Leu Leu Ala Glu Met Glu Leu Leu Phe Gln Arg
            195                 200                 205

Gln Thr Asp Leu Gly Asn Pro His Thr Ser Ala Lys Leu Leu Glu Asn
            210                 215                 220

Leu Thr Ala Leu Leu Met Trp Gln Lys Pro Ala Leu Ala Gly Glu Ala
225                 230                 235                 240

Ile Leu Lys Met Leu Gly Lys Cys Thr Phe Glu Pro Thr Glu Tyr Lys
                245                 250                 255

Ala Ala Lys Asn Ser Tyr Ser Ala Glu Arg Phe Val Trp Leu Thr Lys
                260                 265                 270

Leu Asn Asn Leu Arg Ile Leu Glu Gln Gly Ala Glu Arg Ala Leu Thr
            275                 280                 285

Asp Asn Glu Arg Phe Ala Leu Leu Asp Gln Pro Tyr Glu Lys Ala Lys
            290                 295                 300

Phe Thr Tyr Ala Gln Ala Arg Thr Met Leu Ala Leu Pro Asp Glu Ala
305                 310                 315                 320

Ile Phe Lys Gly Val Arg Tyr Gln Gly Glu Asp Lys Lys Ala Val Glu
                325                 330                 335

Thr Lys Thr Ile Leu Met Glu Met Lys Ala Tyr His Gln Ile Arg Lys
            340                 345                 350

Ala Leu Glu Asn Ala Asp Leu Lys Ala Glu Trp Asn Glu Leu Lys Asn
            355                 360                 365

Asn Ser Glu Leu Leu Asp Asp Ile Gly Thr Ala Phe Ser Leu His Lys
            370                 375                 380

Thr Asp Glu Asp Ile Cys Arg Tyr Leu Asp Gly Lys Leu Ser Glu Ser
385                 390                 395                 400

Ile Leu Asn Ala Leu Leu Glu Asn Leu Asn Phe Asp Lys Phe Ile Gln
                405                 410                 415

Leu Ser Leu Lys Ala Leu Gln Gln Ile Leu Pro Leu Met Leu Gln Gly
            420                 425                 430

Gln Arg Tyr Asp Glu Ala Val Ser Ala Ile Tyr Gly Asp His Tyr Gly
            435                 440                 445
```

```
Lys Lys Ser Ala Glu Ile Asn Arg Leu Leu Pro Thr Ile Pro Ala Asp
    450                 455                 460

Glu Ile Arg Asn Pro Val Val Leu Arg Thr Leu Thr Gln Ala Arg Lys
465                 470                 475                 480

Val Ile Asn Ala Val Val Arg Leu Tyr Gly Ser Pro Ala Arg Ile His
                485                 490                 495

Ile Glu Thr Gly Arg Glu Val Gly Lys Ser Tyr Gln Asp Arg Lys Lys
                500                 505                 510

Leu Glu Lys Gln Gln Glu Asp Asn Arg Lys Gln Arg Glu Ser Ala Val
            515                 520                 525

Lys Lys Phe Lys Glu Tyr Phe Pro Asn Phe Val Gly Glu Pro Lys Gly
530                 535                 540

Lys Asp Ile Leu Lys Met Arg Leu Tyr Glu Leu Gln Gln Ala Lys Cys
545                 550                 555                 560

Leu Tyr Ser Gly Lys Ser Leu Glu Leu His Arg Leu Leu Glu Lys Gly
                565                 570                 575

Tyr Val Glu Val Asp His Ala Leu Pro Phe Ser Arg Thr Trp Asp Asp
                580                 585                 590

Ser Phe Asn Asn Lys Val Leu Val Leu Ala Asn Glu Asn Gln Asn Lys
            595                 600                 605

Gly Asn Leu Thr Pro Tyr Glu Trp Leu Asp Gly Lys Asn Asn Ser Glu
610                 615                 620

His Trp Gln Asn Phe Val Ala Arg Val Gln Thr Ser Gly Phe Ser His
625                 630                 635                 640

Thr Lys Lys Gln Arg Ile Leu Ser His Lys Leu Asp Glu Lys Gly Phe
                645                 650                 655

Ile Glu Arg Asn Leu Asn Asp Thr Arg Tyr Val Ala Arg Phe Leu Cys
                660                 665                 670

Asn Phe Ile Ala Asp Asn Met Leu Leu Thr Gly Lys Gly Lys Arg Lys
            675                 680                 685

Val Phe Ala Ser Asn Gly Gln Ile Thr Ala Leu Leu Arg Gly Arg Trp
690                 695                 700

Gly Leu Gln Lys Val Arg Asp Asp Asn Asp Arg His His Ala Leu Asp
705                 710                 715                 720

Ala Val Val Val Ala Cys Ser Thr Val Met Gln Gln Lys Ile Thr
                725                 730                 735

Arg Phe Val Arg Tyr Glu Glu Gly Asn Val Phe Ser Gly Glu Arg Ile
                740                 745                 750

Asp Arg Glu Thr Gly Glu Ile Ile Pro Leu His Phe Pro Ser Pro Trp
            755                 760                 765

Ala Phe Phe Arg Glu Asn Val Glu Ile Arg Ile Phe Ser Glu Asn Pro
770                 775                 780

Lys Leu Glu Leu Glu Asn Arg Leu Pro Asp Tyr Pro Gln Tyr Asn His
785                 790                 795                 800

Glu Phe Val Gln Pro Leu Phe Val Ser Arg Met Pro Thr Arg Lys Met
                805                 810                 815

Thr Gly Gln Gly His Met Glu Thr Val Lys Ser Ala Lys Arg Leu Asp
                820                 825                 830

Glu Gly Leu Ser Val Leu Lys Val Pro Leu Thr Gln Leu Lys Leu Ser
            835                 840                 845

Asp Leu Glu Arg Met Val Asn Arg Glu Arg Glu Val Thr Leu Tyr Glu
850                 855                 860

Ser Leu Lys Ala Arg Leu Glu Gln Phe Gly Asn Asp Pro Ala Lys Ala
```

-continued

```
            865                 870                 875                 880
Phe Ala Glu Pro Phe His Lys Lys Gly Gly Ala Val Val Lys Ala Val
                    885                 890                 895

Arg Val Glu Gln Thr Gln Lys Ser Gly Val Leu Val Arg Asp Gly Asn
                900                 905                 910

Gly Val Ala Asp Asn Ala Ser Met Val Arg Val Asp Val Phe Thr Lys
            915                 920                 925

Gly Gly Lys Tyr Phe Leu Val Pro Ile Tyr Thr Trp Gln Val Ala Lys
        930                 935                 940

Gly Ile Leu Pro Asn Lys Ala Val Thr Ala Asn Val Asp Glu Ile Asp
945                 950                 955                 960

Trp Leu Glu Met Asp Glu Ser Tyr Gln Phe Ile Phe Thr Met Tyr Pro
                965                 970                 975

Asn Asp Leu Val Lys Val Lys Leu Lys Lys Glu Glu Phe Phe Gly Tyr
            980                 985                 990

Tyr Gly Gly Leu Asp Arg Ala Thr Gly Ala Ile Val Ile Lys Glu His
        995                 1000                1005

Asp Leu Glu Lys Ser Lys Gly Lys Gln Gly Ile Tyr Arg Ile Gly
    1010                1015                1020

Val Lys Leu Ala Leu Ser Phe Glu Lys Tyr Gln Val Asp Glu Leu
    1025                1030                1035

Gly Lys Asn Ile Arg Pro Cys Arg Pro Thr Lys Arg Gln His Val
    1040                1045                1050

Arg
```

HOMOLOGY DEPENDENT REPAIR GENOME EDITING

CROSS-REFERENCE TO RELATED APPLICATION

This application claims the benefit of U.S. Provisional Patent Application No. 62/876,519, filed Jul. 19, 2019, which is incorporated herein by reference in its entirety.

BACKGROUND

Homology-Directed Repair (HDR) is a genome editing method that can be used for precise replacement of a target genomic DNA site with the sequence from a provided DNA template containing the desired replacement sequence. While the results of HDR are quite desirable, it does not work well for a number of reasons. One of the biggest problems is its low overall occurrence frequency, especially when compared to the alternative non-homologous end joining (NHEJ) repair mechanism often triggered by the genome editing molecules that cleave targeted editing sites in the genome. While most cells may have several pathways that could mediate HDR, some of them are most active during the cell cycle, diminishing the success rate of HDR in typical cell culture conditions.

SUMMARY

Disclosed herein are methods, systems, eukaryotic cells (e.g., plant cells), and compositions (e.g., cell culture compositions) that can provide for increased frequencies of modification of a target editing site of the eukaryotic cell genome with a donor template polynucleotide by Homology-Directed Repair (HDR) in comparison to a control. Features of such methods, systems, eukaryotic cells (e.g., plant cells), and compositions (e.g., cell culture compositions) that can provide for such increased frequencies of HDR include provision of a composition comprising at least one HDR promoting agent selected from the group consisting of a compound of Table 1, a compound of Table 2, any bioactive analog thereof, a plant cell-compatible salt thereof, an ester thereof, and any combination thereof in combination with genome editing molecules comprising a sequence-specific endonuclease which cleaves a target editing site in a eukaryotic cell genome and a donor template DNA molecule having homology to the target editing site.

Methods provided herein include methods for increasing Homology Directed Repair (HDR)-mediated genome modification of a plant cell genome, comprising: providing genome editing molecules to a plant cell, wherein the plant cell is exposed to an effective concentration of a composition comprising at least one HDR promoting agent selected from the group consisting of a 5-substituted 2,4-oxazolidinedione, a 5-substituted 2, 4-thiazolidinedione, CAS No. 102649-78-5, CAS No. 128-20-1, CAS No. 549505-65-9, CAS No. 1596-84-5, CAS No. 940929-33-9, CAS No. 336113-53-2, CAS No. 146-77-0, CAS No. 28822-58-4, CAS No. 477845-12-8, CAS No. 872573-93-8, CAS No. 724741-75-7, CAS No. 1357171-62-0, CAS No. 715934-43-2, any bioactive analog thereof, a plant cell-compatible salt thereof, an ester thereof, and any combination thereof; wherein the genome editing molecules comprise an RNA-guided nuclease or a polynucleotide encoding an RNA-guided nuclease, a guide RNA or a polynucleotide encoding a guide RNA, and a donor template DNA molecule; whereby the genome editing molecules modify the plant cell genome by HDR at a frequency that is increased in comparison to a control method wherein a control plant cell is provided with the genome editing molecules but is not exposed to at least one of said HDR promoting agents or any combination thereof.

Systems provided herein include system for modification of a plant gene, comprising: a plant cell; at least one HDR promoting agent selected from the group consisting of a 5-substituted 2,4-oxazolidinedione, 5-substituted 2, 4-thiazolidinedione, CAS No. 102649-78-5, CAS No. 128-20-1, CAS No. 549505-65-9, CAS No. 1596-84-5, CAS No. 940929-33-9, CAS No. 336113-53-2, CAS No. 146-77-0, CAS No. 28822-58-4, CAS No. 477845-12-8, CAS No. 872573-93-8, CAS No. 724741-75-7, CAS No. 1357171-62-0, CAS No. 715934-43-2, any bioactive analog thereof, a plant cell-compatible salt thereof, an ester thereof, and any combination thereof; and genome editing molecule(s) comprising: an RNA-guided nuclease or a polynucleotide encoding an RNA-guided nuclease, a guide RNA or a polynucleotide encoding a guide RNA, and a donor template DNA molecule; wherein the plant cell is associated with, contacts, and/or contains and effective amount of the HDR promoting agent and the genome editing molecule(s).

Methods provided herein include methods for making a plant cell having a genomic modification, comprising: providing genome editing molecules to a plant cell, wherein the plant cell is exposed to an effective amount of at least one HDR promoting agent selected from the group consisting of a 5-substituted 2,4-oxazolidinedione, 5-substituted 2, 4-thiazolidinedione, CAS No. 102649-78-5, CAS No. 128-20-1, CAS No. 549505-65-9, CAS No. 1596-84-5, CAS No. 940929-33-9, CAS No. 336113-53-2, CAS No. 146-77-0, CAS No. 28822-58-4, CAS No. 477845-12-8, CAS No. 872573-93-8, CAS No. 724741-75-7, CAS No. 1357171-62-0, CAS No. 715934-43-2, any bioactive analog thereof, a plant cell-compatible salt thereof, an ester thereof, and any combination thereof; wherein the genome editing molecules comprise an RNA-guided nuclease or a polynucleotide encoding an RNA-guided nuclease, a guide RNA or a polynucleotide encoding a guide RNA, and a donor template DNA molecule; whereby the genome editing molecules modify the plant cell genome by homology directed repair (HDR) at a frequency that is increased in comparison to a control; and isolating or propagating a plant cell comprising the genome modification, thereby making the plant cell having a genomic modification.

DETAILED DESCRIPTION

Unless otherwise stated, nucleic acid sequences in the text of this specification are given, when read from left to right, in the 5' to 3' direction. Nucleic acid sequences may be provided as DNA or as RNA, as specified; disclosure of one necessarily defines the other, as well as necessarily defines the exact complements, as is known to one of ordinary skill in the art. Where a term is provided in the singular, the inventors also contemplate embodiments described by the plural of that term.

The phrase "allelic variant" as used herein refers to a polynucleotide or polypeptide sequence variant that occurs in a different strain, variety, or isolate of a given organism.

The term "and/or" where used herein is to be taken as specific disclosure of each of the two specified features or components with or without the other. Thus, the term "and/or" as used in a phrase such as "A and/or B" herein is intended to include "A and B," "A or B," "A" (alone), and "B" (alone). Likewise, the term "and/or" as used in a phrase such as "A, B, and/or C" is intended to encompass each of the following embodiments: A, B, and C; A, B, or C; A or C; A or B; B or C; A and C; A and B; B and C; A (alone); B (alone); and C (alone).

As used herein, the terms "Cpf1" and "Cas12a" are used interchangeably herein to refer to the same RNA-directed nuclease.

As used herein, the phrase "effective concentration," when used to describe a concentration of an HDR promoting agent or composition comprising the HDR promoting agent, is a concentration sufficient to exert a desired outcome (e.g., increased HDR). In certain embodiments, an effective concentration is a concentration of the agent or composition which is sufficient to provide at least a 1.5-fold increase in the frequency of HDR-mediated gene editing events in comparison to a control wherein the agent or composition is absent.

As used herein, the phrase "gene-editing" includes genome modification by homology-directed repair (HDR), base editing, and non-homologous end joining (NHEJ) mechanisms. Such gene-editing includes embodiments where a sequence-specific endonuclease and a donor template DNA are provided.

As used herein, an "exogenous" agent or molecule refers to any agent or molecule from an external source that is provided to or introduced into a system, composition, a eukaryotic or plant cell culture, reaction system, or a eukaryotic or plant cell. In certain embodiments, the exogenous agent (e.g., polynucleotide, protein, or compound) from the external source can be an agent that is also found in a eukaryotic or plant cell. In certain embodiments, the exogenous agent (e.g., polynucleotide, protein, or compound) from the external source can be an agent that is heterologous to the eukaryotic or plant cell.

As used herein, a "heterologous" agent or molecule refers: (i) to any agent or molecule that is not found in a wild-type, untreated, or naturally occurring composition, eukaryotic cell, or plant cell; and/or (ii) to a polynucleotide or peptide sequence located in, e.g., a genome or a vector, in a context other than that in which the sequence occurs in nature. For example, a promoter that is operably linked to a gene other than the gene that the promoter is operably linked to in nature is a heterologous promoter.

As used herein, the terms "comprise," "comprises," comprising," "include," "includes," and "including" can be interchanged and are to be construed as at least having the features to which they refer while not excluding any additional unspecified features.

As used herein, phrases such as "frequency of HDR," "HDR frequency," and the like refer to the number of HDR-mediated events at a target editing site in comparison to the total number of target editing sites analyzed. The total number of target editing sites is the sum of: (a) target editing sites having NHEJ-mediated events; (b) target editing sites having no changes; and (c) target editing sites having HDR-mediated events. HDR-mediated events include precise insertions of heterologous sequences into a target editing site that do not contain any unintended nucleotide insertions, deletions, or substitutions in either the inserted heterologous sequence, the homologous sequences that flank the heterologous insert, or in the sequences located at the junction of the heterologous sequence and the homologous sequences.

As used herein, the phrase "eukaryotic cell" refers to any cell containing a nucleus and thus includes mammalian (e.g., human, livestock, and companion animal cells), insect cells, reptile cells, plant cells (e.g., monocot and dicot plant cells), yeast cells, and fungal cells (e.g., filamentous and non-filamentous fungi).

As used herein, the phrase "plant cell" can refer either a plant cell having a plant cell wall or to a plant cell protoplast lacking a plant cell wall.

As used herein, the phrase "plant cell-compatible salt" refers to a salt of a compound that can provide for uptake of the compound by a plant cell.

The term "polynucleotide" as used herein is a nucleic acid molecule containing two (2) or more nucleotide residues. Polynucleotides are generally described as single- or double-stranded. Where a polynucleotide contains double-stranded regions formed by intra- or intermolecular hybridization, the length of each double-stranded region is conveniently described in terms of the number of base pairs. Embodiments of the systems, methods, and compositions provided herein can employ or include: (i) one or more polynucleotides of 2 to 25 residues in length, one or more polynucleotides of more than 26 residues in length, or a mixture of both. Polynucleotides can comprise single- or double-stranded RNA, single- or double-stranded DNA, double-stranded DNA/RNA hybrids, chemically modified analogues thereof, or a mixture thereof. In certain embodiments, a polynucleotide can include a combination of ribonucleotides and deoxyribonucleotides (e.g., synthetic polynucleotides consisting mainly of ribonucleotides but with one or more terminal deoxyribonucleotides or synthetic polynucleotides consisting mainly of deoxyribonucleotides but with one or more terminal dideoxyribonucleotides), or can include non-canonical nucleotides such as inosine, thiouridine, or pseudouridine. In certain embodiments, the polynucleotide includes chemically modified nucleotides (see, e.g., Verma and Eckstein (1998) *Annu. Rev. Biochem.*, 67:99-134). Chemically modified nucleotides that can be used in the polynucleotides provided herein include: (i) phosphorothioate, phosphorodithioate, or methylphosphonate internucleotide linkage modifications of the phosphodiester backbone; (ii) nucleosides comprising modified bases and/or modified sugars; and/or (iii) detectable labels including a fluorescent moiety (e.g., fluorescein or rhodamine or a fluorescence resonance energy transfer or FRET pair of chromophore labels) or other label (e.g., biotin or an isotope). Polynucleotides provided or used herein also include modified nucleic acids, particularly modified RNAs, which are disclosed in U.S. Pat. No. 9,464,124, which is incorporated herein by reference in its entirety.

As used herein, the phrase "Reactive Oxygen Species" (ROS) refers to radical and non-radical oxygen species formed by the partial reduction of oxygen. Examples of ROS include hydrogen peroxide, a superoxide radical, a peroxide ion, a hydroperoxyl radical, and/or a hydroxyl radical.

As used herein, the phrase "target editing site" refers to a DNA sequence that contains all sequences required for recognition by a sequence-specific endonuclease. For an RNA guided sequence-specific endonuclease, the target editing site thus includes the PAM site and the adjacent sequence that is complementary to the crRNA-portion of the guide RNA.

As used herein, the phrase "target gene" can refer to either a gene located in the genome that is to be modified by gene editing molecules provided in a system, method, composition and/or eukaryotic cell provided herein. Embodiments of target genes include (protein-)coding sequence, non-coding sequence, and combinations of coding and non-coding sequences. Modifications of a target gene include nucleotide substitutions, insertions, and/or deletions in one or more elements of a gene that include a transcriptional enhancer or promoter, a 5' or 3' untranslated region, a mature or precursor RNA coding sequence, an intron, a splice donor and/or acceptor, a protein coding sequence, a polyadenylation site, and/or a transcriptional terminator. In certain embodiments, all copies or all alleles of a given target gene in a diploid or polyploid plant cell are modified to provide homozygosity of the modified target gene in the plant cell. In embodiments, where a desired trait is conferred by a loss-of-function mutation that is introduced into the target gene by gene editing, a plant cell, population of plant cells, plant, or seed is homozygous for a modified target gene with the loss-of-function mutation. In other embodiments, only a subset of the copies or alleles of a given target gene are modified to provide heterozygosity of the modified target gene in the plant cell. In certain embodiments where a desired trait is conferred by a dominant mutation that is introduced into the target gene by gene editing, a plant cell, population of plant cells, plant, or seed is heterozygous for a modified target gene with the dominant mutation. Traits imparted by such modifications to certain plant target genes include improved yield, resistance to insects, fungi, bacterial pathogens, and/or nematodes, herbicide tolerance, abiotic stress tolerance (e.g., drought, cold, salt, and/or heat tolerance), protein quantity and/or quality, starch quantity and/or quality, lipid quantity and/or quality, secondary metabolite quantity and/or quality, and the like, all in comparison to a control plant that lacks the modification. The plant having a genome modified by gene editing molecules provided in a system, method, composition and/or plant cell provided herein differs from a plant having a genome modified by traditional breeding (i.e., crossing of a male parent plant and a female parent plant), where unwanted and random exchange of genomic regions as well as random mitotically or meiotically generated genetic and epigenetic changes in the genome typically occurs during the cross and are then found in the progeny plants. Thus, in embodiments of the plant (or plant cell) with a modified genome, the modified genome is more than 99.9% identical to the original (unmodified) genome. In embodiments, the modified genome is devoid of random mitotically or meiotically generated genetic or epigenetic changes relative to the original (unmodified) genome. In embodiments, the modified genome includes a difference of epigenetic changes in less than 0.01% of the genome relative to the original (unmodified) genome. In embodiments, the modified genome includes: (a) a difference of DNA methylation in less than 0.01% of the genome, relative to the original (unmodified) genome; or (b) a difference of DNA methylation in less than 0.005% of the genome, relative to the original (unmodified) genome; or (c) a difference of DNA methylation in less than 0.001% of the genome, relative to the original (unmodified) genome. In embodiments, the gene of interest is located on a chromosome in the plant cell, and the modified genome includes: (a) a difference of DNA methylation in less than 0.01% of the portion of the genome that is contained within the chromosome containing the gene of interest, relative to the original (unmodified) genome; or (b) a difference of DNA methylation in less than 0.005% of the portion of the genome that is contained within the chromosome containing the gene of interest, relative to the original (unmodified) genome; or (c) a difference of DNA methylation in less than 0.001% of the portion of the genome that is contained within the chromosome containing the gene of interest, relative to the original (unmodified) genome. In embodiments, the modified genome has not more unintended changes in comparison to the original (unmodified) genome than $1 \times 10^{-8}$ mutations per base pair per replication. In certain embodiments, the modified genome has not more unintended changes than would occur at the natural mutation rate. Natural mutation rates can be determined empirically or are as described in the literature (Lynch, M., 2010; Clark et al., 2005).

To the extent to which any of the preceding definitions is inconsistent with definitions provided in any patent or non-patent reference incorporated herein by reference, any patent or non-patent reference cited herein, or in any patent or non-patent reference found elsewhere, it is understood that the preceding definition will be used herein.

HDR promoting agents that include a compound of Table 1, a compound of Table 2, any bioactive analog thereof, a plant cell-compatible salt thereof, an ester thereof, and any combination thereof are provided herein for use in systems, methods, and compositions that provide for improved homology dependent repair (HDR) in eukaryotic cell gene editing experiments in comparison to control experiments.

TABLE 1

| HDR Promoting agents | | | |
|---|---|---|---|
| Compound | CAS No. | Structure | Description[1] |
| SC-9 | 102649-78-5 | 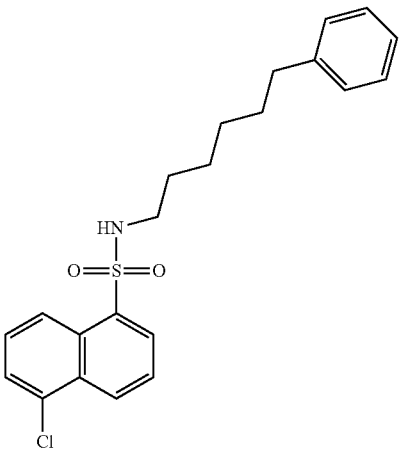 [SMILES: O=S(=O)(NCCCCCCc1ccccc1)c1cccc2c(Cl)cccc12] | Protein kinase C activator |

TABLE 1-continued

HDR Promoting agents

| Compound | CAS No. | Structure | Description[1] |
|---|---|---|---|
| Pregnanolone | 128-20-1 | 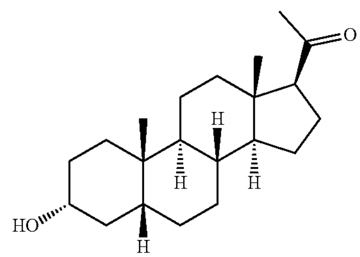 | GABAA receptor positive allosteric modulator |
| ML 3403 | 549505-65-9 | 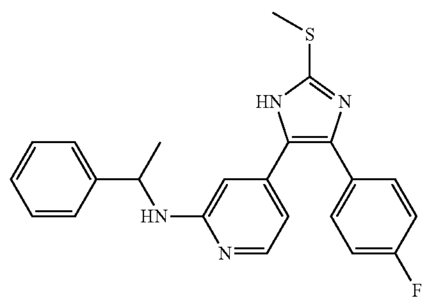 [SMILES: CSc1nc(-c2ccc(F)cc2)c(-c2ccnc(NC(C)c3ccccc3)c2)[nH]1] | p38 MAPK inhibitor |
| Daminozide | 1596-84-5 | 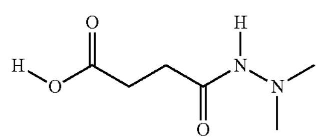 | Selective KDM2/7 inhibitor |
| Rosiglitazone | 122320-73-4 | 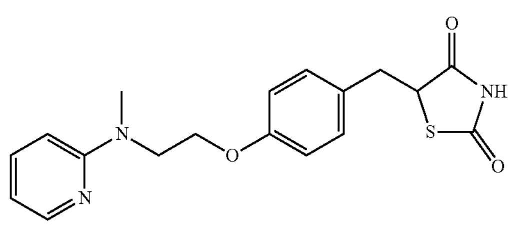 [SMILES: CN(CCOc1ccc(CC2SC(=O)NC2=O)cc1)c1ccccn1] | Potent and selective PPAR-gamma agonist; antidiabetic agent. |
| SB 743921 Hydrochloride | 940929-33-9 | 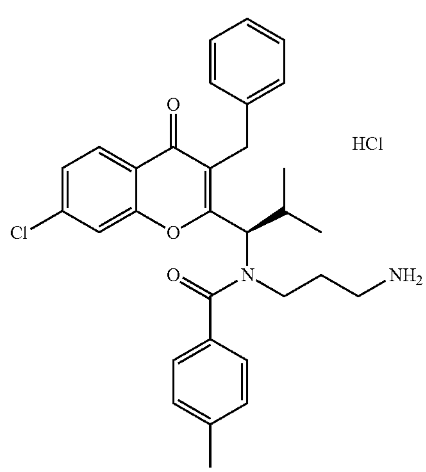 [SMILES: Cc1ccc(C(=O)N(CCCN)[C@@H](c2oc3cc(Cl)ccc3c(=O)c2Cc2ccccc2)C(C)C)cc1 ; Cl] | Kinesin spindle protein (KSP) inhibitor |

TABLE 1-continued

| HDR Promoting agents | | | |
|---|---|---|---|
| Compound | CAS No. | Structure | Description[1] |
| Ispinesib | 336113-53-2 | | High affinity and selective allosteric KSP inhibitor |
| 2-Chloroadenosine | 146-77-0 | | Adenosine receptor agonist |
| Edaglitazone | 213411-83-7 | | Potent and selective PPAR gamma agonist; antidiabetic |
| IBMX | 28822-58-4 | | PDE inhibitor (non-selective) |
| PIM-1 Inhibitor 2 | 477845-12-8 | | Pim-1 kinase inhibitor |

TABLE 1-continued

HDR Promoting agents

| Compound | CAS No. | Structure | Description[1] |
|---|---|---|---|
| Ro 3306 | 872573-93-8 | 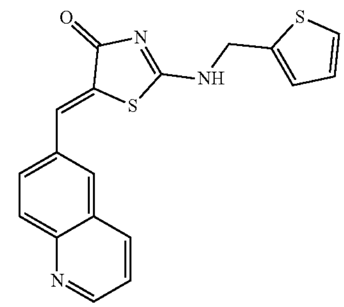 [SMILES: O=C1N=C(NCc2cccs2)S/C1=C\c1ccc2ncccc2c1] | Cyclin-dependent kinase (cdk) 1 inhibitor |
| STF 31 | 724741-75-7 | 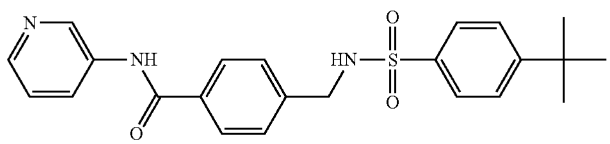 [SMILES: CC(C)(C)c1ccc(S(=O)(=O)NCc2ccc(C(=O)Nc3cccnc3)cc2)cc1] | NAMPT inhibitor; also GLUT1 inhibitor |
| ML 228 | 135171-62-0 | 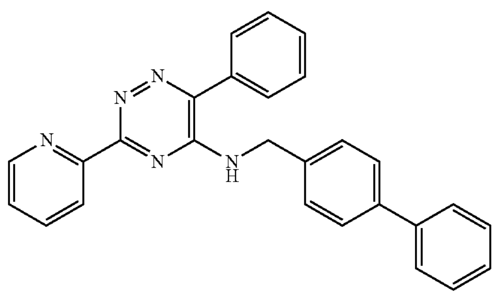 [SMILES: c1ccc(-c2ccc(CNc3nc(-c4ccccn4)nnc3-c3ccccc3)cc2)cc1] | Hypoxia Inducible Factor pathway activator |
| MI 14 | 715934-43-2 | 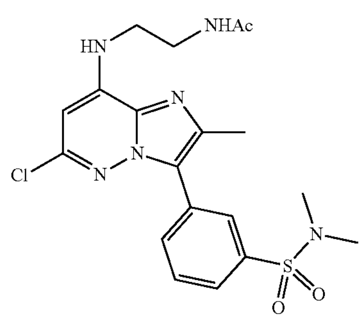 [SMILES: CC(=O)NCCNc1cc(Cl)nn2c(-c3cccc(S(=O)(=O)N(C)C)c3)c(C)nc12] | Potent and selective PI 4-kinase IIIbeta inhibitor |

[1]Activities observed in at least certain mammalian cells.

TABLE 2

5-substituted 2,4-Thiazolidinedione and 5-substituted 2,4-oxazolidinedione HDR Promoting Agents 5-substituted 2,4-thiazolidinedione

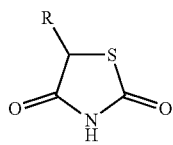

TABLE 2-continued
5-substituted 2,4-Thiazolidinedione and 5-substituted 2,4-oxazolidinedione HDR Promoting Agents
| Rosiglitazone | 122320-73-4 | 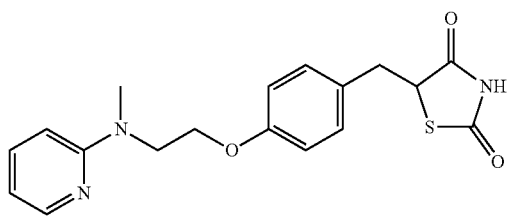 [SMILES: CN(CCOc1ccc(CC2SC(=O)NC2=O)cc1)c1ccccn1] |
| Edaglitazone | 213411-83-7 | 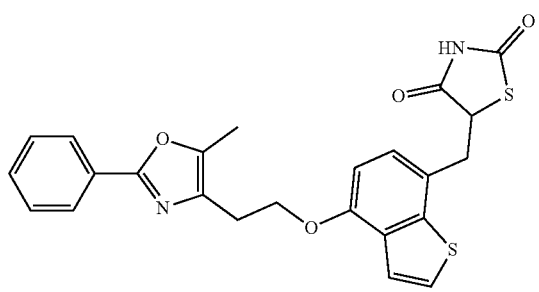 [SMILES: Cc1oc(-c2ccccc2)nc1CCOc1ccc(CC2SC(=O)NC2=O)c2sccc12] |
| Ciglitazone | 74772-77-3 | 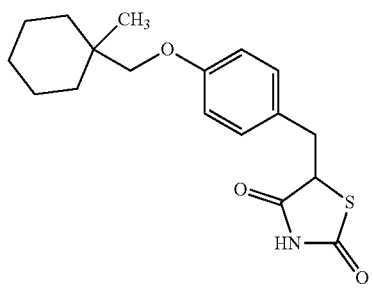 [SMILES: CC1(COc2ccc(CC3SC(=O)NC3=O)cc2)CCCCC1] |
| Lobeglitazone | 607723-33-1 | 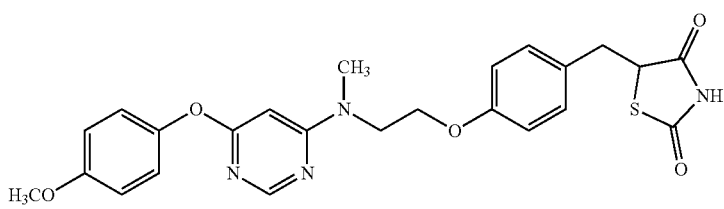 [SMILES: COc1ccc(Oc2cc(N(C)CCOc3ccc(CC4SC(=O)NC4=O)cc3)ncn2)cc1] |
| Pioglitazone | 112529-15-4 | 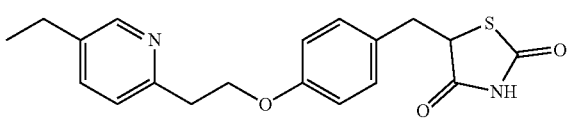 [SMILES: CCc1ccc(CCOc2ccc(CC3SC(=O)NC3=O)cc2)nc1] |
| Troglitazone | 97322-87-7 | 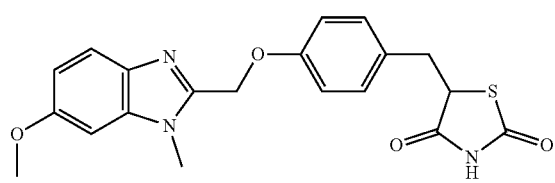 [SMILES: COc1ccc2nc(COc3ccc(CC4SC(=O)NC4=O)cc3)n(C)c2c1] |
| Mitoglitazone | 146062-49-9 | 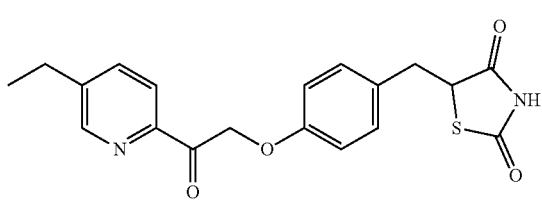 [SMILES: CCc1ccc(C(=O)COc2ccc(CC3SC(=O)NC3=O)cc2)nc1] |

TABLE 2-continued
5-substituted 2,4-Thiazolidinedione and 5-substituted 2,4-oxazolidinedione HDR Promoting Agents
| Darglitazone | 141200-24-0 | 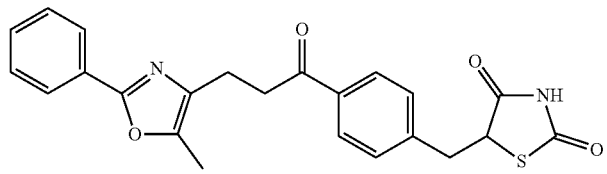 [SMILES: Cc1oc(-c2ccccc2)nc1CCC(=O)c1ccc(CC2SC(=O)NC2=O)cc1] |
| Englitazone | 109229-58-5 | 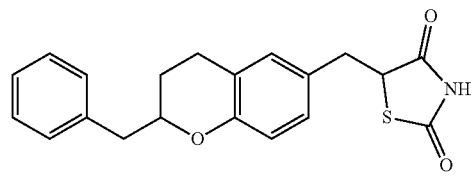 [SMILES: O=C1NC(=O)C(Cc2ccc3c(c2)CCC(Cc2ccccc2)O3)S1] |
| Netoglitazone | 161600-01-7 | 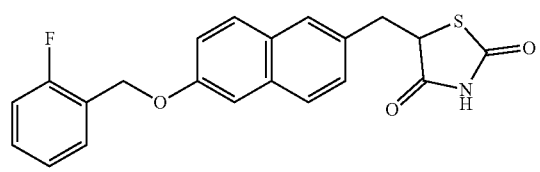 [SMILES: O=C1NC(=O)C(Cc2ccc3cc(OCc4ccccc4F)ccc3c2)S1] |
| Rivoglitazone | 185428-18-6 | 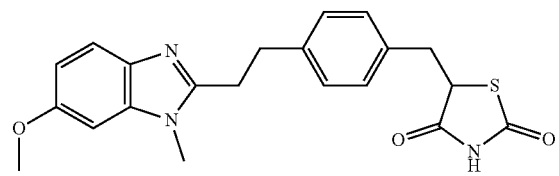 |
| Balaglitazone | 199113-98-9 | 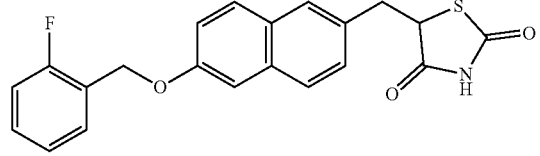 [SMILES: O=C1NC(=O)C(Cc2ccc3cc(OCc4ccccc4F)ccc3c2)S1] |
| 5-substituted 2,4-oxazolidinedione | | 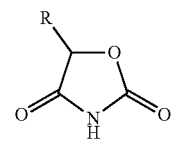 |
| 5-[[4-[2-[methyl(pyridin-2-yl)amino]ethoxy]pheny]methyl]-1,3-oxazolidine-2,4-dione | | 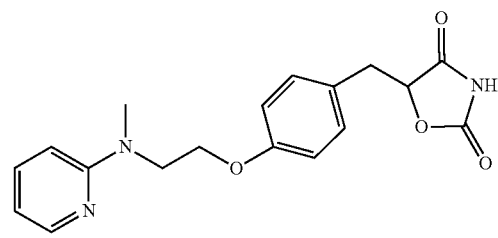 [SMILES: CN(CCOc1ccc(CC2OC(=O)NC2=O)cc1)c1ccccn1] |
| 5-[[4-[2-(5-methyl-2-phenyl-1,3-oxazol-4-yl)ethoxy]-1-benzothiophen-7-yl]methyl]-1,3-oxazolidine-2,4-dione | | 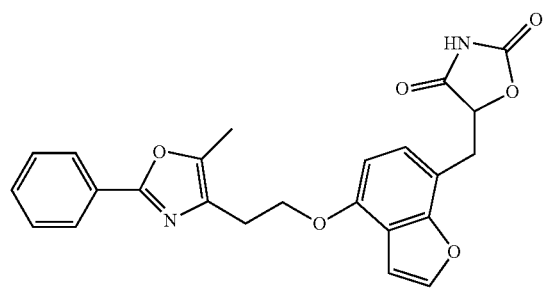 [SMILES: Cc1oc(-c2ccccc2)nc1CCOc1ccc(CC2OC(=O)NC2=O)c2occc12] |

The generic 5-substituted 2, 4-thiazolidinediones and 5-substituted 2,4-oxazolidinediones set forth in Table 2 also encompass the 5-substituted 2, 4-thiazolidinediones and 5-substituted 2,4-oxazolidinediones, and methods of synthesis described in the U.S. Pat. Nos. 6,380,191, 6,313,113, 6,172,089, 5,665,748, 5,441,971, 5,075,300, 4,997,948, 4,918,091, 4,725,610, and 4,582,839, which are each incorporated herein by reference in their entireties. The generic 5-substituted 2, 4-thiazolidinediones and 5-substituted 2,4-oxazolidinediones set forth in Table 2 also encompass 5-substituted 2, 4-thiazolidinediones and 5-substituted 2,4-oxazolidinediones described in Momose et al., 2002. The generic 5-substituted 2,4-oxazolidinediones set forth in Table 2 also encompass 5-substituted 2,4-oxazolidinediones comprising the R groups of the 5-substituted 2, 4-thiazolidinediones Rosiglitazone (CAS No. 122320-73-4), Edaglitazone (CAS No. 213411-83-7), Ciglitazone (CAS No. 74772-77-3), Lobeglitazone (CAS No. 607723-33-1), Pioglitazone hydrochloride (CAS No. 112529-15-4), Troglitazone (CAS No. 97322-87-7), Mitoglitazone (CAS No. 146062-49-9), Darglitazone (CAS No. 141200-24-0), Englitazone (CAS No. 109229-58-5), Netoglitazone (CAS No. 161600-01-7), Rivoglitazone (CAS No. 185428-18-6), and Balaglitazone (CAS No. 199113-98-9). Two examples of 5-substituted 2,4-oxazolidinediones comprising the R groups of the 5-substituted 2, 4-thiazolidinediones Rosiglitazone (CAS No. 122320-73-4) and Edaglitazone (CAS No. 213411-83-7) are set forth in Table 2 as 5-[[4-[2-[methyl(pyridin-2-yl)amino] ethoxy]phenyl]methyl]-1,3-oxazolidine-2,4-dione and 5-[[4-[2-(5-methyl-2-phenyl-1,3-oxazol-4-yl)ethoxy]-1-benzothiophen-7-yl]methyl]-1,3-oxazolidine-2,4-dione, respectively.

Bioactive analogs of the compounds of Table 1 or Table 2 include compounds wherein at least one group and/or atom in the compound of Table 1 or Table 2 is substituted with a distinct group and/or atom to provide a distinct compound with HDR promoting activity. In certain embodiments, the group and/or atom is substituted with a group and/or atom with similar polarity, valency, and/or steno characteristics. Examples of substitutions of groups in a compound of Table 1 or Table 2 which can provide for a bioactive analog include: (i) substitution of a halogen (e.g.; Fluorine (F), Chlorine (Cl), Bromine (Br), Iodine (I)) for another halogen; (ii) a substitution of a C1 to C6 alkyl or C1 to C6 alkoxy group with a different C1 to C6 alkyl or C1 to C6 alkoxy group, respectively (e.g., C2 alkyl for a C3, C4, C5, or C6 alkyl; or a branched alkyl or alkoxy for an unbranched (straight-chain) alkyl or alkoxyl; or C1 alkoxy for a C2, C3, C4, C5, or C6 alkoxy); (iii) a substitution of an unsubstituted phenyl group with a substituted phenyl group, wherein optionally the substitutions in the phenyl group are selected from a methyl, an alkoxy, aminoalkyl, or halogen; and/or, a substitution of a substituted phenyl group with a different substituted phenyl group wherein optionally the substitutions in the phenyl group are selected from a methyl, an alkoxy, aminoalkyl, or halogen. In certain embodiments, such bioactive analogs of the compounds of Table 1 or Table 2 can be identified by assaying the analogs either alone or in parallel with a compound of Table 1 or Table 2 for the ability to modify the plant cell genome by HDR at a frequency that is increased in comparison to a control. Such controls include mock treatments of plant cells or plants with a solvent (e.g., DMSO) and genome editing molecules or with genome editing molecules alone.

In certain embodiments, the compounds of Table 1 or Table 2 are provided to plant cells as plant cell compatible salts. Plant cell compatible salts of a compound of Table 1 or Table 2 can include sodium, potassium, ammonium, hydrochloric acid (HCl), acetate, amine (e.g., monomethylamine, ethanolamine, diglycolamine, dimethyl amine, isopropylamine), or trimesium salts. In certain embodiments, salts of the aforementioned compounds can be provided to plant cells in a composition that further comprises one or more adjuvants such as a surfactant.

In certain embodiments, the compounds of Table 1 or Table 2 are provided to plant cells as esters (i.e., in an esterified form). Such esters include esters formed by esterification of a carboxylic acid group which is present in the compound set forth in Table 1 (e.g., CAS No. 1596-84-5; CAS No. 715934-43-2). Such esters include esters formed by esterification of a carboxylic acid group which has been added to a compound set forth in Table 1 or 2. Examples of suitable esters include methyl, ethyl, propyl, butyl, hexyl, heptyl, and octyl esters.

In certain embodiments, HDR is increased in isolated plant cells or plant protoplasts (i.e., are not located in undissociated or intact plant tissues, plant parts, or whole plants). In certain embodiments, the plant cells are obtained from any plant part or tissue or callus. In certain embodiments, the culture includes plant cells obtained from a plant tissue, a cultured plant tissue explant, whole plant, intact nodal bud, shoot apex or shoot apical meristem, root apex or root apical meristem, lateral meristem, intercalary meristem, seedling, whole seed, halved seed or other seed fragment, zygotic embryo, somatic embryo, immature embryo, ovule, pollen, microspore, anther, hypocotyl, cotyledon, leaf, petiole, stem, tuber, root, callus, or plant cell suspension. In certain embodiments, the plant cell is derived from the L1 or L2 layer of an immature or mature embryo of a monocot plant (e.g., maize, wheat, sorghum, or rice).

In certain embodiments of the methods, systems, and compositions provided herein, HDR promoting agent (e.g., HDR promoting agents that include a compound of Table 1, a compound of Table 2, any bioactive analog thereof, a plant cell-compatible salt thereof, an ester thereof, and any combination thereof) or composition comprising the HDR promoting agent are provided to a plant, plant part, plant tissue, or plant cell at an effective concentration that provides for increased HDR frequencies in comparison to a control plant, plant part, plant tissue, or plant cell which has not been exposed to the HDR promoting agent or composition. In certain embodiments, an effective concentration of the HDR promoting agent or composition comprising the HDR promoting agent is a concentration that provides for exposure of a plant, plant part, plant tissue or plant cell to the HDR promoting agent at a concentration of least about 0.1 µM, 0.25 µM, 0.5 µM, or 1 µM to about 10 µM, 25 µM, 50 µM, 100 µM, or 500 µM. In certain embodiments, an effective concentration of the HDR promoting agent or composition comprising the HDR promoting agent is a concentration that provides for exposure of a plant, plant part, plant tissue or plant cell to the HDR promoting agent at a concentration of least about 0.1 µM to about 10 µM, about 0.1 µM to about 25 µM, about 0.1 µM to about 50 µM, about 0.1 µM to about 100 µM, or about 0.1 µM to about 500 µM. In certain embodiments, an effective concentration of the HDR promoting agent or composition comprising the HDR promoting agent is a concentration that provides for exposure of a plant, plant part, plant tissue or plant cell to the HDR promoting agent at a concentration of least about 0.25 µM to about 10 µM, about 0.25 µM to about 25 µM, about 0.25 µM to about 50 µM, about 0.25 µM to about 100 µM, or about 0.25 µM to about 500 µM. In certain embodiments, an effective concentration of the HDR promoting agent or composition comprising the HDR promoting agent is a concentration that provides for exposure of a plant, plant part, plant tissue or plant cell to the HDR promoting agent at a concentration of least about 0.5 μM to about 10 μM, about 0.5 μM to about 25 μM, about 0.5 μM to about 50 μM, about 0.5 μM to about 100 μM, or about 0.5 μM to about 500 μM. In certain embodiments, an effective concentration of the HDR promoting agent or composition comprising the HDR promoting agent is a concentration that provides for exposure of a plant, plant part, plant tissue or plant cell to the HDR promoting agent at a concentration of least about 1 μM to about 10 μM, about 1 μM to about 25 μM, about 1 μM to about 50 μM, about 1 μM to about 100 μM, or about 1 μM to about 500 μM. In certain embodiments, an effective concentration of the HDR promoting agent or composition comprising the HDR promoting agent is a concentration that provides for exposure of a plant cell to the HDR promoting agent at a concentration of least about 0.5 μM, 1 μM, 2 μM, or 4 μM to about 6 μM, 10 μM, 25 μM, or 50 μM.

In certain embodiments of the methods, systems, and compositions provided herein, HDR promoting agent (e.g., HDR promoting agents that include a compound of Table 1, a compound of Table 2, any bioactive analog thereof, a plant cell-compatible salt thereof, an ester thereof, and any combination thereof) or composition comprising the HDR promoting agent are provided can increase the frequency of HDR in comparison to a control plant cell which has not been exposed to the HDR promoting agent or composition by a factor of at least 1.5-fold, 2-fold, 3-fold, 4-fold, 5-fold, 6-fold, or 7-fold. In certain embodiments, the HDR promoting agent or composition comprising the same can increase the frequency of HDR by a factor of about 1.5-fold, 2-fold or 3-fold to about 6-fold, 8-fold, or 10-fold.

In certain embodiments, HDR is increased in plant cells that are located in undissociated or intact plant tissues, plant parts, plant explants, or whole plants. In certain embodiments, the plant cell can be located in an intact nodal bud, a cultured plant tissue explant, shoot apex or shoot apical meristem, root apex or root apical meristem, lateral meristem, intercalary meristem, seedling, whole seed, halved seed or other seed fragment, zygotic embryo, somatic embryo, immature embryo, ovule, pollen, microspore, anther, hypocotyl, cotyledon, leaf, petiole, stem, tuber, root, or callus. In certain embodiments, the explants used include immature embryos. Immature embryos (e.g., immature maize embryos) include 1.8-2.2 mm embryos, 1-7 mm embryos, and 3-7 mm embryos. In certain embodiments, the aforementioned embryos are obtained from mature ear-derived seed, leaf bases, leaves from mature plants, leaf tips, immature inflorescences, tassels, immature ears, and silks. In various aspects, the plant-derived explant used for transformation includes immature embryos, 1.8-2.2 mm embryos, 1-7 mm embryos, and 3.5-7 mm embryos. In an aspect, the explants used in the disclosed methods can be derived from mature ear-derived seed, leaf bases, leaves from mature plants, leaf tips, immature inflorescences, tassel, immature ear, or silks. In certain embodiments, the plant cell is a pluripotent plant cell (e.g., a stem cell or meristem cell). In certain embodiments, the plant cell is located within the L1 or L2 layer of an immature or mature embryo of a monocot plant (e.g., maize, wheat, sorghum, or rice). In certain embodiments, methods of editing genomes of whole plants, seeds, embryos, explants, or meristematic tissue published in WO2018085693, which is incorporated herein by reference in its entirety, can be adapted for use in the plant cells and related systems, methods, compositions, or cultures provided herein.

In certain embodiments, the plant cells can comprise haploid, diploid, or polyploid plant cells or plant protoplasts, for example, those obtained from a haploid, diploid, or polyploid plant, plant part or tissue, or callus. In certain embodiments, plant cells in culture (or the regenerated plant, progeny seed, and progeny plant) are haploid or can be induced to become haploid; techniques for making and using haploid plants and plant cells are known in the art, see, e.g., methods for generating haploids in *Arabidopsis thaliana* by crossing of a wild-type strain to a haploid-inducing strain that expresses altered forms of the centromere-specific histone CENH3, as described by Maruthachalam and Chan in "How to make haploid *Arabidopsis thaliana*", protocol available at www[dot]openwetware[dot]org/images/d/d3/Haploid_Arabidopsis_protocol[dot]pdf; (Ravi et al. (2014) *Nature Communications*, 5:5334, doi: 10.1038/ncomms6334). Haploids can also be obtained in a wide variety of monocot plants (e.g., maize, wheat, rice, sorghum, barley) or dicot plants (e.g., soybean, *Brassica* sp. including canola, cotton, tomato) by crossing a plant comprising a mutated CENH3 gene with a wildtype diploid plant to generate haploid progeny as disclosed in U.S. Pat. No. 9,215,849, which is incorporated herein by reference in its entirety. Haploid-inducing maize lines that can be used to obtain haploid maize plants and/or cells include Stock 6, MHI (Moldovian Haploid Inducer), indeterminate gametophyte (ig) mutation, KEMS, RWK, ZEM, ZMS, KMS, and well as transgenic haploid inducer lines disclosed in U.S. Pat. No. 9,677,082, which is incorporated herein by reference in its entirety. Examples of haploid cells include but are not limited to plant cells obtained from haploid plants and plant cells obtained from reproductive tissues, e.g., from flowers, developing flowers or flower buds, ovaries, ovules, megaspores, anthers, pollen, megagametophyte, and microspores. In certain embodiments where the plant cell or plant protoplast is haploid, the genetic complement can be doubled by chromosome doubling (e.g., by spontaneous chromosomal doubling by meiotic non-reduction, or by using a chromosome doubling agent such as colchicine, oryzalin, trifluralin, pronamide, nitrous oxide gas, anti-microtubule herbicides, anti-microtubule agents, and mitotic inhibitors) in the plant cell or plant protoplast to produce a doubled haploid plant cell or plant protoplast wherein the complement of genes or alleles is homozygous; yet other embodiments include regeneration of a doubled haploid plant from the doubled haploid plant cell or plant protoplast. Another embodiment is related to a hybrid plant having at least one parent plant that is a doubled haploid plant provided by this approach. Production of doubled haploid plants provides homozygosity in one generation, instead of requiring several generations of self-crossing to obtain homozygous plants. The use of doubled haploids is advantageous in any situation where there is a desire to establish genetic purity (i.e. homozygosity) in the least possible time. Doubled haploid production can be particularly advantageous in slow-growing plants, such as fruit and other trees, or for producing hybrid plants that are offspring of at least one doubled-haploid plant.

In certain embodiments where the HDR promoting agents are used to increase HDR in plant cells, as well as the related methods, systems, compositions, or reaction mixtures provided herein can include plant cells obtained from or located in any monocot or dicot plant species of interest, for example, row crop plants, fruit-producing plants and trees, vegetables, trees, and ornamental plants including ornamental flowers, shrubs, trees, groundcovers, and turf grasses. In certain non-limiting embodiments, the plant cells are obtained from or located in alfalfa (*Medicago sativa*), almonds (*Prunus dulcis*), apples (*Malus* x *domesfica*), apricots (*Prunus armeniaca, P. brigantine, P. mandshurica, P. mume, P. sibirica*), asparagus (*Asparagus officinalis*), bananas (*Musa* spp.), barley (*Hordeum vulgare*), beans (*Phaseolus* spp.), blueberries and cranberries (*Vaccinum* spp.), cacao (*Theobroma cacao*), canola and rapeseed or oilseed rape, (*Brassica napus*), carnation (*Dianthus caryophyllus*), carrots (*Daucus carota sativus*), cassava (*Manihot esculentum*), cherry (*Prunus avium*), chickpea (*Cider arietinum*), chicory (*Cichorium intybus*), chili peppers and other *capsicum* peppers (*Capsicum annuum, C. frutescens, C. chinense, C. pubescens, C. baccatum*), chrysanthemums (*Chrysanthemum* spp.), coconut (*Cocos nucifera*), coffee (*Coffea* spp. including *Coffea arabica* and *Coffea canephora*), cotton (*Gossypium hirsutum* L.), cowpea (*Vigna unguiculata*), cucumber (*Cucumis sativus*), currants and gooseberries (*Ribes* spp.), eggplant or aubergine (*Solanum melongena*), eucalyptus (*Eucalyptus* spp.), flax (*Linum usitatissumum* L.), geraniums (*Pelargonium* spp.), grapefruit (*Citrus xparadisi*), grapes (*Vitus* spp.) including wine grapes (*Vitus vinifera*), guava (*Psidium guajava*), hemp and cannabis (e.g., *Cannabis sativa* and *Cannabis* spp.), hops (*Humulus lupulus*), irises (*Iris* spp.), lemon (*Citrus limon*), lettuce (*Lactuca sativa*), limes (*Citrus* spp.), maize (*Zea mays* L.), mango (*Mangifera indica*), mangosteen (*Garcinia mangostana*), melon (*Cucumis melo*), millets (*Setaria* spp, *Echinochloa* spp, *Eleusine* spp, *Panicum* spp., *Pennisetum* spp.), oats (*Avena sativa*), oil palm (*Ellis quineensis*), olive (*Olea europaea*), onion (*Allium cepa*), orange (*Citrus sinensis*), papaya (*Carica papaya*), peaches and nectarines (*Prunus persica*), pear (*Pyrus* spp.), pea (*Pisa sativum*), peanut (*Arachis hypogaea*), peonies (*Paeonia* spp.), petunias (*Petunia* spp.), pineapple (*Ananas comosus*), plantains (*Musa* spp.), plum (*Prunus domesfica*), poinsettia (*Euphorbia pulcherrima*), Polish canola (*Brassica rapa*), poplar (*Populus* spp.), potato (*Solanum tuberosum*), pumpkin (*Cucurbita pepo*), rice (*Oryza sativa* L.), roses (*Rosa* spp.), rubber (*Hevea brasiliensis*), rye (*Secale cereale*), safflower (*Carthamus tinctorius* L), sesame seed (*Sesame indium*), sorghum (*Sorghum bicolor*), soybean (*Glycine max* L.), squash (*Cucurbita pepo*), strawberries (*Fragaria* spp., *Fragaria* x *ananassa*), sugar beet (*Beta vulgaris*), sugarcanes (*Saccharum* spp.), sunflower (*Helianthus annus*), sweet potato (*Ipomoea batatas*), tangerine (*Citrus tangerina*), tea (*Camellia sinensis*), tobacco (*Nicotiana tabacum* L.), tomato (*Lycopersicon esculentum*), tulips (*Tuhpa* spp.), turnip (*Brassica rapa rapa*), walnuts (*Juglans* spp. L.), watermelon (*Citrulus lanatus*), wheat (*Tritium aestivum*), or yams (*Discorea* spp.).

In certain embodiments, the eukaryotic cells (e.g., plant cells) where the HDR promoting agents are used to increase HDR can be cells that are (a) encapsulated or enclosed in or attached to a polymer (e.g., pectin, agarose, or other polysaccharide) or other support (solid or semi-solid surfaces or matrices, or particles or nanoparticles); (b) encapsulated or enclosed in or attached to a vesicle or liposome or other fluid compartment; or (c) not encapsulated or enclosed or attached. In certain embodiments, the cells can be in liquid or suspension culture, or cultured in or on semi-solid or solid media, or in a combination of liquid and solid or semi-solid media (e.g., plant cells or protoplasts cultured on solid medium with a liquid medium overlay, or plant cells or protoplasts attached to solid beads or a matrix and grown with a liquid medium). In certain embodiments, the cells encapsulated in a polymer (e.g., pectin, agarose, or other polysaccharide) or other encapsulating material, enclosed in a vesicle or liposome, suspended in a mixed-phase medium (such as an emulsion or reverse emulsion), or embedded in or attached to a matrix or other solid support (e.g., beads or microbeads, membranes, or solid surfaces).

In a related aspect, the disclosure provides arrangements of eukaryotic cells (e.g., plant cells) where the HDR promoting agents are used to improve HDR frequencies in the systems, methods, and compositions described herein, such as arrangements of cells convenient for screening purposes or for high-throughput and/or multiplex transformation or gene editing experiments. In an embodiment, the disclosure provides an arrangement of multiple cells comprising: (a) the HDR promoting agents; and optionally (b) genome editing molecules. In certain embodiments, the arrangements of cells can further comprise at least one chemical, enzymatic, or physical delivery agent. In another embodiment, the disclosure provides an array including a plurality of containers, each including at least one cell having increased HDR-mediated genome modification frequencies. In an embodiment, the disclosure provides arrangements of cells provided with the HDR promoting agents and optionally the genome editing molecules, wherein the cells are in an arrayed format, for example, in multi-well plates, encapsulated or enclosed in vesicles, liposomes, or droplets (useful, (e.g., in a microfluidics device), or attached discretely to a matrix or to discrete particles or beads; a specific embodiment is such an arrangement of multiple cells having increased HDR-mediated genome modification frequencies provided in an arrayed format, further including at least one genome editing molecules (e.g., an RNA-guided DNA nuclease, at least one guide RNA, or a ribonucleoprotein including both an RNA-guided DNA nuclease and at least one guide RNA), which may be different for at least some locations on the array or even for each location on the array, and optionally at least one chemical, enzymatic, or physical delivery agent.

In the systems and methods provided herein, eukaryotic cells (e.g., plant cells) can be exposed to one or more HDR promoting agents and/or one or more gene editing molecules in any temporal order. In certain embodiments, the HDR promoting agents and gene editing molecules are provided simultaneously. In other embodiments, the genome editing molecules are provided after the HDR promoting agents are provided. In other embodiments, the gene editing molecules are provided before the HDR promoting agents are provided. In summary, the HDR promoting agents can be provided to a eukaryotic cell (e.g., a plant cell) either previous to, concurrently with, or subsequent to exposing the cell to the gene editing molecules.

In certain embodiments of the systems, methods, and compositions provided herein, the plant cell exposed to one or more HDR promoting agents set forth in Table 1, Table 2, any bioactive analog thereof, a plant cell-compatible salt thereof, or an ester thereof, is also exposed to and/or maintained under hypoxic conditions. Normal (i.e., "normoxic") oxygen conditions comprise about 20% oxygen by volume. Hypoxic conditions used in the systems, methods, and compositions provided herein can in certain embodiments comprise about 14%, 13%, 12%, 11%, or 10% to about 8%, 7%, 6%, or 5% oxygen by volume. In certain embodiments, hypoxic conditions can comprise treating the plant cells with a hypoxia mimetic (e.g., desferrioxamine or cobalt chloride). In certain embodiments, a hypoxic condition can comprises maintaining the cell in a liquid culture media having a dissolved oxygen concentration that is lower than the dissolved oxygen concentration obtained when the liquid culture media is under normoxic conditions. Such exposure of the plant cell to the hypoxic condition can in certain embodiments be limited to a period of time necessary to realize improvements in gene editing frequencies (e.g., prior to and/or during association, contact, and/or containment to/of an HDR promoting agent and/or gene editing molecule; prior to and/or during exposure and/or after to an HDR promoting agent and/or gene editing molecule). Such exposure and or maintenance of a plant cell under hypoxic conditions can be achieved in the context of a plant cell in isolated form (e.g., as a protoplast), a plant cell in a plant embryo, plant callus, especially embryogenic callus, in an isolated plant tissue or part (e.g., an ovule, anther, leaf, meristematic tissue, and the like), or in a whole plant. In certain embodiments, the plant cell in any of the aforementioned contexts can be in a liquid or solid culture medium that includes about 20, about 40, or about 60 to about 80, about 100, about 120, or about 150 millimolar $Ca^{2+}$ and/or $Mg^{2+}$, and is exposed to and/or maintained under hypoxic conditions. In certain embodiments, the plant cells (e.g., plant protoplasts) are exposed to the hypoxic conditions about 5, 10, 15, 30, or 45 minutes to about 60, 75, 90, or 120 minutes after exposure to the gene-editing molecules and/or HDR promoting agent. In certain embodiments, the combination of the aforementioned hypoxic conditions with an HDR promoting agent provides a synergistic increase in frequencies of gene editing through homology directed repair (HDR) pathways that exceeds the sum of the increases in HDR provided by the hypoxic conditions and HDR promoting agents alone. In certain embodiments, the combination of the aforementioned hypoxic conditions with an HDR promoting agent and any of the aforementioned divalent cations provides a synergistic increase in frequencies of gene editing through homology directed repair (HDR) pathways that exceeds the sum of the increases in HDR provided each of the hypoxic conditions, HDR promoting agents, and divalent cations alone. In certain embodiments of any of the aforementioned systems, methods, and compositions, the HDR promoting agent is selected from the group consisting of a 5-substituted 2,4-oxazolidinedione, a 5-substituted 2, 4-thiazolidinedione, CAS No. 102649-78-5, CAS No. 549505-65-9, CAS No. 336113-53-2, CAS No. 146-77-0, CAS No. 28822-58-4, CAS No. 477845-12-8, CAS No. 872573-93-8, CAS No. 724741-75-7, CAS No. 1357171-62-0, CAS No. 715934-43-2, any bioactive analog thereof, a plant cell-compatible salt thereof, an ester thereof, and any combination thereof. In certain embodiments of any of the aforementioned systems, methods, and compositions, the 5-substituted 2, 4-thiazolidinedione is selected from the group consisting of Rosiglitazone (CAS No. 122320-73-4), Edaglitazone (CAS No. 213411-83-7); Ciglitazone (CAS No. 74772-77-3), Lobeglitazone (CAS No. 607723-33-1), Pioglitazone hydrochloride (CAS No. 112529-15-4), Troglitazone (CAS No. 97322-87-7), Mitoglitazone (CAS No. 146062-49-9), Darglitazone (CAS No. 141200-24-0), Englitazone (CAS No. 109229-58-5), Netoglitazone (CAS No. 161600-01-7), Rivoglitazone (CAS No. 185428-18-6), Balaglitazone (CAS No. 199113-98-9), and a plant cell-compatible salt thereof.

Embodiments of the systems, methods, or compositions provided herein include cultures wherein the plant cell exposed to one or more HDR promoting agents set forth in Table 1, Table 2, any bioactive analog thereof, a plant cell-compatible salt thereof, or an ester thereof, is also exposed to or treated with an enzymatic and/or a non-enzymatic ROS scavenging agent. In certain embodiments, such exposure or treatment with the enzymatic and/or a non-enzymatic ROS scavenging agent results in lowered concentrations of ROS (e.g., hydrogen peroxide, a superoxide radical, a peroxide ion, a hydroperoxyl radical, and/or a hydroxyl radical) in the exposed or treated plant cell in comparison to an unexposed or untreated plant cell. In certain embodiments, the non-enzymatic ROS scavenging agents include low-molecular-weight antioxidants, including lipid-soluble antioxidants and water-soluble antioxidants (e.g., low-molecular-weight thiol antioxidants, pro-thiols, ascorbic acid, tocopherols, carotenoids, flavonoids, butylated hydroxytoluene, and butylated hydroxyanisole). Suitable low molecular weight thiol compounds include compounds having a molecular weight of 1,000 daltons (Da) or less. In certain embodiments, the non-enzymatic ROS scavenging agents are provided at a concentration of about 0.1 to about 10 millimolar, or about 1, 2, or 4 to about 8 or 10 millimolar. Specific embodiments include cultures wherein the culture medium includes about 0.1 to about 10 millimolar or about 1, 2, or 4 to about 8 or 10 millimolar low-molecular-weight thiol antioxidants; see, e.g., Pivato et al. (2014) Archives Biochem. Biophys., 560:83-99. Low-molecular-weight thiol antioxidants useful in the systems, methods, and compositions include glutathione (gamma-glutamylcysteinyl glycine), cysteine, cysteinyl glycine, gamma-glutamyl cysteine, N-acetylcysteine, cysteine, thiocysteine, homocysteine, lipoic acid, and/or dithiothreitol (any of which can also be used in combination with each other at a similar final thiol concentration). ROS scavenging agents useful in the systems, methods, and compositions also include pro-thiols (e.g., L-2-oxothiazolidine-4-carboxylate (OTC)) which are converted to thiols in the cell. In certain embodiments, the plant cell is exposed or treated with enzymatic ROS scavenging agents. Enzymatic ROS scavenging agents include any catalase, ascorbate peroxidase, a dehydroascorbate reductase, guaiacol peroxidase, monodehydroascorbate reductase, a peroxidase, and/or superoxide dismutase. In certain embodiments, an enzymatic ROS scavenging agents is provided in the culture medium. In certain embodiments, an enzymatic ROS scavenging agent or polynucleotides encoding the same can be introduced into the plant cell (e.g., by transient or stable transformation, transfection, or with a delivery agent). A combination of at least one enzymatic and at least one non-enzymatic ROS scavenging agent can also be used. Specific embodiments also include plant cell or plant protoplast cultures wherein the culture medium includes about 20, about 40, or about 60 to about 80, about 100, about 120, or about 150 millimolar $Ca^{2+}$, and/or in which the culture medium includes about 0.1, about 0.25, about 0.5, about 0.75, about 1, or about 2 to about 4, about 6, about 8, or about 10 millimolar low-molecular-weight thiol antioxidant. Further embodiments encompassed are plant cell or plant protoplast cultures wherein the culture medium includes combinations of divalent cations and low-molecular-weight antioxidants, with the individual components present in the culture at concentrations similar to those listed above. In certain embodiments, the plant cells (e.g., plant protoplasts) are exposed to the ROS scavenging agents about 5, 10, 15, 30, or 45 minutes to about 60, 75, 90, or 120 minutes after exposure to the gene-editing molecules and/or HDR promoting agent. In certain embodiments, the plant cells (e.g., plant protoplasts) are exposed to the ROS scavenging agents prior to or at the same time that they are exposed to the gene-editing molecules and/or HDR promoting agent. In certain embodiments, the combination of the aforementioned ROS scavenging agents with an HDR promoting agent provides a synergistic increase in frequencies of gene editing through homology directed repair (HDR) pathways that exceeds the sum of the increases in HDR provided by the ROS scavenging agents and HDR promoting agents alone. In certain embodiments, the combination of the aforementioned ROS scavenging agents with an HDR promoting agent and any of the aforementioned divalent cations provides a synergistic increase in frequencies of gene editing through homology directed repair (HDR) pathways that exceeds the sum of the increases in HDR provided by the ROS scavenging agents, HDR promoting agents, and divalent cations. In certain embodiments of any of the aforementioned systems, methods, and compositions, the HDR promoting agent is selected from the group consisting of a 5-substituted 2,4-oxazolidinedione, a 5-substituted 2, 4-thiazolidinedione, CAS No. 102649-78-5, CAS No. 549505-65-9, CAS No. 336113-53-2, CAS No. 146-77-0, CAS No. 28822-58-4, CAS No. 477845-12-8, CAS No. 872573-93-8, CAS No. 724741-75-7, CAS No. 1357171-62-0, CAS No. 715934-43-2, any bioactive analog thereof, a plant cell-compatible salt thereof, an ester thereof, and any combination thereof. In certain embodiments of any of the aforementioned systems, methods, and compositions, the 5-substituted 2, 4-thiazolidinedione is selected from the group consisting of Rosiglitazone (CAS No. 122320-73-4), Edaglitazone (CAS No. 213411-83-7), Ciglitazone (CAS No. 74772-77-3), Lobeglitazone (CAS No. 607723-33-1), Pioglitazone hydrochloride (CAS No. 112529-15-4), Troglitazone (CAS No. 97322-87-7), Mitoglitazone (CAS No. 146062-49-9), Darglitazone (CAS No. 141200-24-0), Englitazone (CAS No. 109229-58-5), Netoglitazone (CAS No. 161600-01-7), Rivoglitazone (CAS No. 185428-18-6), Balaglitazone (CAS No. 199113-98-9), and a plant cell-compatible salt thereof.

In certain embodiments, the plant cell or plant protoplast cultures are exposed to the HDR promoting agents, a composition or culture media comprising the HDR promoting agents, or to the HDR promoting agents and aforementioned hypoxic conditions, ROS scavenging agents, and/or Ca 2+ concentrations immediately before or after introduction of a gene editing molecule, or during the time that they are treated with a gene editing molecule and immediately afterwards. In certain embodiments, the plant cell or plant protoplast cultures are exposed to HDR promoting agents, a composition or culture media comprising the HDR promoting agents, or to the HDR promoting agents and aforementioned hypoxic conditions, ROS scavenging agents, and/or Ca 2+ concentrations the before and/or during the time that they are treated with a gene editing molecule and/or immediately afterwards. Exposure of the plant cell or plant protoplast the HDR promoting agents, a composition or culture media comprising the HDR promoting agents, or to the HDR promoting agents and aforementioned hypoxic conditions, ROS scavenging agents, and/or Ca 2+ concentrations can be for about 1, 2, 4, 6, or 8 to about 12, 18, 24, 36, or 48 hours after introduction of a gene editing molecule. Gene editing molecules can be introduced by methods that include transfection, Agrobacterium-mediated transformation, Agro-infection, electroporation, and the like. In certain embodiments, the plant cell or plant protoplast is maintained at a temperature of about 30° C., 32° C., 34° C., or 36° C. to about 38° C., 40° C., or 42° C. for at least about 30, 40, 50, or 60 minutes, or for about 30, 40, 50, 60, to about 70, 80, 90, or 120 minutes, following introduction of the gene editing molecules Eukaryotic cells (e.g., plant cells) having increased Homology Directed Repair (HDR)-mediated genome modification frequencies conferred by exposure to HDR promoting agents (e.g., a compound of Table 1, a compound of Table 2, any bioactive analog thereof, a plant cell-compatible salt thereof, an ester thereof, and any combination thereof) and/or are provided herein. Also provided by the disclosure are compositions or compositions derived from or grown from the plant cell or plant protoplast having increased HDR-mediated genome modification frequencies provided by the systems and methods disclosed herein. In certain embodiments, such compositions include multiple protoplasts or cells, callus, a somatic embryo, a somatic meristem, embryogenic callus, or a regenerated plant grown from the plant cell or plant protoplast having increased HDR-mediated genome modification frequencies; wherein the HDR promoting agent (e.g., a compound of Table 1, a compound of Table 2, any bioactive analog thereof, a plant cell-compatible salt thereof, an ester thereof, and any combination thereof) is provided at an effective concentration. Increased HDR-mediated genome modification frequencies in cells that have been exposed to HDR promoting agents can be assessed by a variety of techniques. In certain embodiments, such techniques can compare the frequency of HDR observed in cells exposed to the HDR promoting agents versus the frequency of HDR in control cells that were not exposed to HDR promoting agent.

In certain embodiments, the eukaryotic cells (e.g., plant cells) used in the systems, methods, and compositions provided herein can include non-dividing cells. Such non-dividing cells can include plant cell protoplasts, eukaryotic cells subjected to one or more of a genetic and/or pharmaceutically-induced cell-cycle blockage, and the like. In certain embodiments, the non-dividing cells can be induced to divide (e.g., by reversing or removing a genetic or pharmaceutical cell-cycle blockages) following treatment with the HDR-promoting agents (e.g., a compound of Table 1, a compound of Table 2, any bioactive analog thereof, a plant cell-compatible salt thereof, an ester thereof, and any combination thereof).

In certain embodiments, the eukaryotic cells (e.g., plant cells) in used in the systems, methods, and compositions provided herein can include dividing cells. Dividing cells can include those cells found in various plant tissues including leaves, meristems, and embryos. These tissues include, but are not limited to dividing cells from young maize leaf, meristems and scutellar tissue from about 8 or 10 to about 12 or 14 days after pollination (DAP) embryos. The isolation of maize embryos has been described in several publications (Brettschneider, Becker, and Lörz 1997; Leduc et al. 1996; Frame et al. 2011; K. Wang and Frame 2009). In certain embodiments, basal leaf tissues (e.g., leaf tissues located about 0 to 3 cm from the ligule of a maize plant; Kirienko, Luo, and Sylvester 2012) are targeted for HDR-mediated gene editing. Methods for obtaining regenerable plant structures and regenerating plants from the HDR-mediated gene editing of plant cells provided herein can be adapted from methods disclosed in US Patent Application Publication No. 20170121722, which is incorporated herein by reference in its entirety and specifically with respect to such disclosure. In certain embodiments, single plant cells subjected to the HDR-mediated gene editing will give rise to single regenerable plant structures. In certain embodiments, the single regenerable plant cell structure can form from a single cell on, or within, an explant that has been subjected to the HDR-mediated gene editing.

In some embodiments, methods provided herein can include the additional step of growing or regenerating a plant from a plant cell that had been subjected to the improved HDR-mediated gene editing or from a regenerable plant structure obtained from that plant cell. In certain embodiments, the plant can further comprise an inserted transgene, a target gene edit, or genome edit as provided by the methods and compositions disclosed herein. In certain embodiments, callus is produced from the plant cell, and plantlets and plants produced from such callus. In other embodiments, whole seedlings or plants are grown directly from the plant cell without a callus stage. Thus, additional related aspects are directed to whole seedlings and plants grown or regenerated from the plant cell or plant protoplast having a target gene edit or genome edit, as well as the seeds of such plants. In certain embodiments wherein the plant cell or plant protoplast is subjected to genetic modification (for example, genome editing by means of, e.g., an RNA-guided DNA nuclease), the grown or regenerated plant exhibits a phenotype associated with the genetic modification. In certain embodiments, the grown or regenerated plant includes in its genome two or more genetic or epigenetic modifications that in combination provide at least one phenotype of interest. In certain embodiments, a heterogeneous population of plant cells having a target gene edit or genome edit, at least some of which include at least one genetic or epigenetic modification, is provided by the method; related aspects include a plant having a phenotype of interest associated with the genetic or epigenetic modification, provided by either regeneration of a plant having the phenotype of interest from a plant cell or plant protoplast selected from the heterogeneous population of plant cells having a target gene or genome edit, or by selection of a plant having the phenotype of interest from a heterogeneous population of plants grown or regenerated from the population of plant cells having a target gene edit or genome edit. Examples of phenotypes of interest include herbicide resistance, improved tolerance of abiotic stress (e.g., tolerance of temperature extremes, drought, or salt) or biotic stress (e.g., resistance to nematode, bacterial, or fungal pathogens), improved utilization of nutrients or water, modified lipid, carbohydrate, or protein composition, improved flavor or appearance, improved storage characteristics (e.g., resistance to bruising, browning, or softening), increased yield, altered morphology (e.g., floral architecture or color, plant height, branching, root structure). In an embodiment, a heterogeneous population of plant cells having a target gene edit or genome edit (or seedlings or plants grown or regenerated therefrom) is exposed to conditions permitting expression of the phenotype of interest; e.g., selection for herbicide resistance can include exposing the population of plant cells having a target gene edit or genome edit (or seedlings or plants grown or regenerated therefrom) to an amount of herbicide or other substance that inhibits growth or is toxic, allowing identification and selection of those resistant plant cells (or seedlings or plants) that survive treatment. Methods for obtaining regenerable plant structures and regenerating plants from plant cells or regenerable plant structures can be adapted from published procedures (Roest and Gilissen, Acta Bot. Neerl., 1989, 38(1), 1-23; Bhaskaran and Smith, Crop Sci. 30(6):1328-1337; Ikeuchi et al., Development, 2016, 143: 1442-1451). Methods for obtaining regenerable plant structures and regenerating plants from plant cells or regenerable plant structures can also be adapted from US Patent Application Publication No. 20170121722, which is incorporated herein by reference in its entirety and specifically with respect to such disclosure. Also provided are heterogeneous populations, arrays, or libraries of such plants, succeeding generations or seeds of such plants grown or regenerated from the plant cells or plant protoplasts, having a target gene edit or genome edit, parts of the plants (including plant parts used in grafting as scions or rootstocks), or products (e.g., fruits or other edible plant parts, cleaned grains or seeds, edible oils, flours or starches, proteins, and other processed products) made from the plants or their seeds. Embodiments include plants grown or regenerated from the plant cells having a target gene edit or genome edit, wherein the plants contain cells or tissues that do not have a genetic or epigenetic modification, e.g., grafted plants in which the scion or rootstock contains a genetic or epigenetic modification, or chimeric plants in which some but not all cells or tissues contain a genetic or epigenetic modification. Plants in which grafting is commonly useful include many fruit trees and plants such as many citrus trees, apples, stone fruit (e.g., peaches, apricots, cherries, and plums), avocados, tomatoes, eggplant, cucumber, melons, watermelons, and grapes as well as various ornamental plants such as roses. Grafted plants can be grafts between the same or different (generally related) species. Additional related aspects include a hybrid plant provided by crossing a first plant grown or regenerated from a plant cell or plant protoplast having a target gene edit or genome edit and having at least one genetic or epigenetic modification, with a second plant, wherein the hybrid plant contains the genetic or epigenetic modification; also contemplated is seed produced by the hybrid plant. Also envisioned as related aspects are progeny seed and progeny plants, including hybrid seed and hybrid plants, having the regenerated plant as a parent or ancestor. The plant cells and derivative plants and seeds disclosed herein can be used for various purposes useful to the consumer or grower. The intact plant itself may be desirable, e.g., plants grown as cover crops or as ornamentals. In other embodiments, processed products are made from the plant or its seeds, such as extracted proteins, oils, sugars, and starches, fermentation products, animal feed or human food, wood and wood products, pharmaceuticals, and various industrial products.

An HDR promoting agent can be provided to a eukaryotic cell (e.g., a plant cell or plant protoplast) in the methods, systems, and compositions provided herein by any suitable technique. In certain embodiments, the HDR promoting agent is provided by directly contacting a cell with the HDR promoting agent. In certain embodiments, the HDR promoting agent is provided by transporting the HDR promoting agent into a cell using a chemical, enzymatic, or physical agent.

In certain embodiments of the methods, systems, cells, and compositions provided herein, transient expression of the genome editing molecules is used. Transient expression of genome editing molecules can be achieved by a variety of techniques. In certain embodiments, the genome editing molecules are provided directly to the cells, systems, methods, and compositions as isolated molecules, as isolated or semi-purified products of a cell free synthetic process (e.g., in vitro translation), or as isolated or semi-purified products of in a cell-based synthetic process (e.g., such as in a bacterial or other cell lysate). In certain embodiments, genome editing molecules are targeted to the cell or cell nucleus in a manner that insures transient expression (e.g., by methods adapted from Gao et al. 2016; or Li et al. 2009). In certain embodiments, the genome editing molecules are delivered into the cell by delivery of the genome editing molecule in the absence of any polynucleotide that encodes the genome editing molecule. Examples of exogenous genome editing molecules that can be delivered in the absence of any encoding polynucleotides include sequence-specific endonucleases, and RNA guides. RNA-guided DNA binding polypeptide/RNA guides can be delivered separately and/or as RNP complexes. In certain embodiments, gene editing molecules can be produced in a heterologous system, purified and delivered to plant cells by particle bombardment (e.g., by methods adapted from Martin-Ortigosa and Wang 2014). In embodiments where the gene editing molecules are delivered in the absence of any encoding polynucleotides, the delivered agent is expected to degrade over time in the absence of ongoing expression from any introduced encoding polynucleotides to result in transient expression. In certain embodiments, the genome editing molecules can be delivered into the cell by delivery of a polynucleotide that encodes the genome editing molecules. In certain embodiments, genome editing molecules can be encoded on a bacterial plasmid and delivered to plant tissue by particle bombardment (e.g., by methods adapted from Hamada et al. 2018; or Kirienko, Luo, and Sylvester 2012). In certain embodiments, genome editing molecules can be encoded on a T-DNA and transiently transferred to plant cells using *Agrobacterium* (e.g., by methods adapted from Leonelli et al. 2016; or Wu et al. 2014). In certain embodiments, genome editing molecules can be encoded in a viral genome and delivered to plants (e.g., by methods adapted from Honig et al. 2015). In certain embodiments, genome editing molecules can be encoded in mRNA or an RNA comprising an internal ribosome entry site (IRES) and delivered to target cells. In certain embodiments where the genome editing molecules comprise an RNA-guided DNA binding polypeptide and an RNA guide, the polypeptide or guide can be delivered by a combination of: (i) an encoding polynucleotide for either polypeptide or the guide; and (ii) either the polypeptide or the guide itself in the absence of an encoding polynucleotide. In certain embodiments, the polynucleotide that encodes the genome editing molecules is not integrated into a plant cell genome (e.g., as a polynucleotide lacking sequences that provide for integration, by agroinfiltration on an integration deficient T-DNA vector or system, or in a viral vector), is not operably linked to polynucleotides which provide for autonomous replication, and/or only provided with factors (e.g., viral replication proteins) that provide for autonomous replication. Suitable techniques for transient expression including biolistic and other micro- or nanoparticulate-mediated delivery of polynucleotides, agroinfiltration, and use of viral vectors as disclosed by Canto, 2016 and others can be adapted for transient expression of the genome editing molecules provided herein. Transient expression of the genome editing molecules encoded by a non-integrated polynucleotide can be effectuated by excision of the polynucleotide and/or regulated expression of the genome editing molecules. In certain embodiments, the polynucleotide that encodes the gene editing molecules is integrated into a eukaryotic cell genome (e.g., a plant nuclear or plastid genome) and transient expression of the agent is effectuated by excision of the polynucleotide and/or regulated expression of the gene editing molecules. Excision of a polynucleotide encoding the gene editing molecules can be provided by use of site-specific recombination systems (e.g., Cre-Lox, FLP-FRT). Regulated expression of the gene editing molecules can be effectuated by methods including: (i) operable linkage of the polynucleotide encoding the gene editing molecules to a developmentally regulated, de-repressable, and/or inducible promoter; and/or (ii) introduction of a polynucleotide (e.g., dsRNA or a miRNA) that can induce siRNA-mediated inhibition of the genome editing molecules. Suitable site-specific recombination systems as well as developmentally regulated, de-repressable, and/or inducible promoters include those disclosed in US Patent Application Publication No. 20170121722, which is incorporated herein by reference in its entirety and specifically with respect to such disclosure.

Polynucleotides that can be used to effectuate transient expression of genome editing molecules (e.g., a polynucleotide encoding a sequence-specific endonuclease, RNA-guided endonuclease, and/or a guide RNA) include: (a) double-stranded RNA; (b) single-stranded RNA; (c) chemically modified RNA; (d) double-stranded DNA; (e) single-stranded DNA; (f) chemically modified DNA; or (g) a combination of any of (a)-(f). Certain embodiments of the polynucleotide further include additional nucleotide sequences that provide useful functionality; non-limiting examples of such additional nucleotide sequences include an aptamer or riboswitch sequence, nucleotide sequence that provides secondary structure such as stem-loops or that provides a sequence-specific site for an enzyme (e.g., a sequence-specific recombinase or endonuclease site), T-DNA (e.g., DNA sequence encoding a genome editing molecule is enclosed between left and right T-DNA borders from *Agrobacterium* spp. or from other bacteria that infect or induce tumors in plants), a DNA nuclear-targeting sequence, a regulatory sequence such as a promoter sequence, and a transcript-stabilizing or -destabilizing sequence. Certain embodiments of the polynucleotides comprising gene-editing molecules include those wherein the polynucleotide is complexed with, or covalently or non-covalently bound to, a non-nucleic acid element, e.g., a carrier molecule, an antibody, an antigen, a viral movement protein, a cell-penetrating or pore-forming peptide, a polymer, a detectable label, a quantum dot, or a particulate or nanoparticulate.

Various treatments are useful in delivery of gene editing molecules and/or an HDR-promoting agent (e.g., a compound of Table 1, a compound of Table 2, any bioactive analog thereof, a plant cell-compatible salt thereof, an ester thereof, and any combination thereof) to a eukaryotic cell (e.g., a plant cell). In certain embodiments, one or more treatments is employed to deliver the gene editing molecules and/or an HDR promoting agent (e.g., comprising a polynucleotide, polypeptide, compound, or combination thereof) into a eukaryotic or plant cell, e.g., through barriers such as a cell wall, a plasma membrane, a nuclear envelope, and/or other lipid bilayer. In certain embodiments, a composition comprising the HDR promoting agent(s) are delivered directly, for example by direct contact of the composition with a eukaryotic cell. Aforementioned compositions can be provided in the form of a liquid, a solution, a suspension, an emulsion, a reverse emulsion, a colloid, a dispersion, a gel, liposomes, micelles, an injectable material, an aerosol, a solid, a powder, a particulate, a nanoparticle, or a combination thereof can be applied directly to a eukaryotic cell, eukaryotic tissue, eukaryotic organ, eukaryotic organism, plant, plant part, plant cell, or plant explant (e.g., through abrasion or puncture or otherwise disruption of the cell wall or cell membrane, by spraying or dipping or soaking or otherwise directly contacting, by microinjection). For example, a plant cell or plant protoplast is soaked in a liquid composition comprising the HDR promoting agent, whereby the agent is delivered to the plant cell. In certain embodiments, the agent-containing composition is delivered using negative or positive pressure, for example, using vacuum infiltration or application of hydrodynamic or fluid pressure. In certain embodiments, the HDR promoting agent-containing composition is introduced into a plant cell or plant protoplast, e.g., by microinjection or by disruption or deformation of the cell wall or cell membrane, for example by physical treatments such as by application of negative or positive pressure, shear forces, or treatment with a chemical or physical delivery agent such as surfactants, liposomes, or nanoparticles; see, e.g., delivery of materials to cells employing microfluidic flow through a cell-deforming constriction as described in US Published Patent Application 2014/0287509, incorporated by reference in its entirety herein. Other techniques useful for delivering the agent-containing composition to a eukaryotic cell, plant cell or plant protoplast include: ultrasound or sonication; vibration, friction, shear stress, vortexing, cavitation; centrifugation or application of mechanical force; mechanical cell wall or cell membrane deformation or breakage; enzymatic cell wall or cell membrane breakage or permeabilization; abrasion or mechanical scarification (e.g., abrasion with carborundum or other particulate abrasive or scarification with a file or sandpaper) or chemical scarification (e.g., treatment with an acid or caustic agent); and electroporation. In certain embodiments, the agent-containing composition is provided by bacterially mediated (e.g., *Agrobacterium* sp., *Rhizobium* sp., *Sinorhizobium* sp., *Mesorhizobium* sp., *Bradyrhizobium* sp., *Azobacter* sp., *Phyllobacterium* sp.) transfection of the plant cell or plant protoplast with a polynucleotide encoding the agent (e.g., sequence-specific endonuclease, and/or guide RNA); see, e.g., Broothaerts et al. (2005) *Nature,* 433:629-633. Any of these techniques or a combination thereof are alternatively employed on the plant explant, plant part or tissue or intact plant (or seed) from which a plant cell is optionally subsequently obtained or isolated; in certain embodiments, the agent-containing composition is delivered in a separate step after the plant cell has been isolated. In certain embodiments, the aforementioned methods can also be used to introduce a genome editing molecule into the eukaryotic cell (e.g., plant cell).

In embodiments, a treatment employed in delivery of an HDR-promoting agent (e.g., a compound of Table 1, a compound of Table 2, any bioactive analog thereof, a plant cell-compatible salt thereof, an ester thereof, and any combination thereof) to a eukaryotic cell (e.g., plant cell) is carried out under a specific thermal regime, which can involve one or more appropriate temperatures, e.g., chilling or cold stress (exposure to temperatures below that at which normal plant growth occurs), or heating or heat stress (exposure to temperatures above that at which normal plant growth occurs), or treating at a combination of different temperatures. In certain embodiments, a specific thermal regime is carried out on the plant cell, or on a plant, plant explant, or plant part from which a plant cell or plant protoplast is subsequently obtained or isolated, in one or more steps separate from the HDR promoting agent delivery. In certain embodiments, the aforementioned methods can also be used to introduce a genome editing molecule into the eukaryotic cell.

In certain embodiments of the plant parts, systems, methods, and compositions provided herein, a whole plant or plant part or seed, or an isolated plant cell, a plant explant, or the plant or plant part from which a plant cell or plant protoplast is obtained or isolated, is treated with one or more delivery agents which can include at least one chemical, enzymatic, or physical agent, or a combination thereof. In certain embodiments, a composition comprising an HDR promoting agent further includes one or more than one chemical, enzymatic, or physical agents for delivery. Treatment with the chemical, enzymatic or physical agent can be carried out simultaneously with the agent delivery or in one or more separate steps that precede or follow the agent delivery. In certain embodiments, a chemical, enzymatic, or physical agent, or a combination of these, is associated or complexed with the HDR promoting agent; examples of such associations or complexes include those involving non-covalent interactions (e.g., ionic or electrostatic interactions, hydrophobic or hydrophilic interactions, formation of liposomes, micelles, or other heterogeneous composition) and covalent interactions (e.g., peptide bonds, bonds formed using cross-linking agents). In non-limiting examples, the HDR promoting agent is provided as a liposomal complex with a cationic lipid; and/or the HDR promoting agent is provided as a complex with a carbon nanotube. Examples of agents useful for delivering the HDR promoting agents include the various cationic liposomes and polymer nanoparticles reviewed by Zhang et al. (2007) *J. Controlled Release,* 123:1-10, and the cross-linked multilamellar liposomes described in US Patent Application Publication 2014/0356414 A1, incorporated by reference in its entirety herein. In any of the aforementioned embodiments, it is further contemplated that the aforementioned methods can also be used to introduce a genome editing molecule into the eukaryotic cell (e.g., plant cell).

In certain embodiments, the compositions used in the methods, systems, and compositions that comprise an HDR promoting agent (e.g., a compound of Table 1, a compound of Table 2, any bioactive analog thereof, a plant cell-compatible salt thereof, an ester thereof, and any combination thereof) or gene-editing molecules can further include one or more chemical agents such as:

(a) solvents (e.g., water, dimethylsulfoxide, dimethylformamide, acetonitrile, N-pyrrolidine, pyridine, hexamethylphosphoramide, alcohols, alkanes, alkenes, dioxanes, polyethylene glycol, and other solvents miscible or emulsifiable with water or that will dissolve the HDR promoting agent in non-aqueous systems);

(b) fluorocarbons (e.g., perfluorodecalin, perfluoromethyldecalin);

(c) glycols or polyols (e.g., propylene glycol, polyethylene glycol);

(d) surfactants, including cationic surfactants, anionic surfactants, non-ionic surfactants, and amphiphilic surfactants, e.g., alkyl or aryl sulfates, phosphates, sulfonates, or carboxylates; primary, secondary, or tertiary amines: quaternary ammonium salts; sultaines, betaines; cationic lipids; phospholipids; tallowamine; bile acids such as cholic acid; long chain alcohols; organosilicone surfactants including non-ionic organosilicone surfactants such as trisiloxane ethoxylate surfactants or a silicone polyether copolymer such as a copolymer of polyalkylene oxide modified heptamethyl trisiloxane and allyloxypolypropylene glycol methylether (commercially available as SILWET L-77™ brand surfactant having CAS Number 27306-78-1 and EPA Number CAL. REG. NO. 5905-50073-AA, Momentive Performance Materials, Inc., Albany, N.Y.); specific examples of useful surfactants include sodium lauryl sulfate, the Tween series of surfactants, Triton-X100, Triton-X114, CHAPS and CHAPSO, Tergitol-type NP-40, Nonidet P-40;

(e) lipids, lipoproteins, lipopolysaccharides;

(f) acids, bases, caustic agents;

(g) peptides, proteins, or enzymes (e.g., cellulase, pectolyase, maceroenzyme, pectinase), including cell-penetrating or pore-forming peptides (e.g., (BO100)2K8, Genscript; poly-lysine, poly-arginine, or poly-homoarginine peptides; gamma zein, see US Patent Application publication 2011/0247100, incorporated herein by reference in its entirety; transcription activator of human immunodeficiency virus type 1 ("HIV-1 Tat") and other Tat proteins, see, e.g., www[dot]lifetein[dot]com/Cell_Penetrating_Peptides[dot]

html and Järver (2012) *Mol. Therapy—Nucleic Acids,* 1:e27, 1-17); octa-arginine or nona-arginine; poly-homoarginine (see Unnamalai et al. (2004) *FEBS Letters,* 566:307-310); see also the database of cell-penetrating peptides CPPsite 2.0 publicly available at crdd[dot]osdd[dot]net/raghava/cpp-site/(h)

(h) RNase inhibitors;

(i) cationic branched or linear polymers such as chitosan, poly-lysine, DEAE-dextran, polyvinylpyrrolidone ("PVP"), or polyethylenimine ("PEI", e.g., PEI, branched, MW 25,000, CAS #9002-98-6; PEI, linear, MW 5000, CAS #9002-98-6; PEI linear, MW 2500, CAS #9002-98-6);

(j) dendrimers (see, e.g., US Patent Application Publication 2011/0093982, incorporated herein by reference in its entirety);

(k) counter-ions, amines or polyamines (e.g., spermine, spermidine, putrescine), osmolytes, buffers, and salts (e.g., calcium phosphate, ammonium phosphate);

(l) polynucleotides (e.g., non-specific double-stranded DNA, salmon sperm DNA);

(m) transfection agents (e.g., Lipofectin®, Lipofectamine®, and Oligofectamine®, and Invivofectamine® (all from Thermo Fisher Scientific, Waltham, Mass.), PepFect (see Ezzat et al. (2011) *Nucleic Acids Res.,* 39:5284-5298), Transit® transfection reagents (Mirus Bio, LLC, Madison, Wis.), and poly-lysine, poly-homoarginine, and poly-arginine molecules including octo-arginine and nono-arginine as described in Lu et al. (2010) *J. Agric. Food Chem.,* 58:2288-2294);

(n) antibiotics, including non-specific DNA double-strand-break-inducing agents (e.g., phleomycin, bleomycin, talisomycin); and/or (o) antioxidants (e.g., glutathione, dithiothreitol, ascorbate). In any of the aforementioned embodiments, it is further contemplated that the aforementioned chemical agents can also be used to introduce a genome editing molecule into the eukaryotic cell (e.g., plant cell).

In certain embodiments, the compositions used in the methods, systems, and compositions that comprise an HDR promoting agent (e.g., a compound of Table 1, a compound of Table 2, any bioactive analog thereof, a plant cell-compatible salt thereof, an ester thereof, and any combination thereof) are provided to a plant cell in a composition comprising an agriculturally acceptable adjuvant and/or an agriculturally acceptable excipient. Agriculturally acceptable adjuvants include agents that facilitate mixing, application, uptake and/or bioactivity (e.g., increased HDR frequencies) of compositions comprising an HDR promoting agent. Such adjuvants include pH buffering agents, antifoam agents, and drift control agents, surfactants, crop oil concentrates, nitrogen fertilizers (e.g., urea-ammonium nitrates, ammonium sulfates, ammonium nitrates and ammonium polyphosphates), spreader-stickers, wetting agents, humectants (e.g., glycerol, propylene glycol, diethylene glycol, polyethylene glycol), and penetrants. Useful surfactants that can be used include any of the aforementioned cationic surfactants, anionic surfactants, non-ionic surfactants, and amphiphilic surfactants. Useful crop oil concentrates include mixtures of a non-phytotoxic oil at about 80% to 90% by weight or volume and surfactant(s) at about 20% to 1% by weight or volume. Non-phytotoxic oils include petroleum oils, petroleum oil concentrates (e.g., paraffinic and napthalenic oils) and vegetable oils (e.g., triglycerides or methylated oils). Agriculturally acceptable excipients include agents that are essentially inert but function as bulking agents and/or carriers. Agricultural excipients suitable for solid compositions include natural clays, kaolin, pyrophyllite, bentonite, alumina, montmorillonite, kieselguhr, chalk, diatomaceous earths, calcium phosphates, pumice, attapulgite clays, fuller's earth, ground corn cobs, sands, silicates, sodium, calcium or magnesium carbonates, sodium bicarbonate, magnesium sulphate, lime, flours, talc, polysaccharides and other organic and inorganic solid carriers. Agricultural excipients suitable for liquid compositions include water, oil and water emulsions, organic solvents, and the like.

In certain embodiments, the chemical agent is provided simultaneously with the HDR promoting agent (e.g., as a composition comprising a compound of Table 1, a compound of Table 2, any bioactive analog thereof, a plant cell-compatible salt thereof, an ester thereof, and any combination thereof and any of the aforementioned chemical agents). In certain embodiments, HDR promoting agent is is non-covalently linked or complexed with one or more chemical agents; for example, an HDR promoting agent can be non-covalently complexed with cationic lipids, polycations (e.g., polyamines), or cationic polymers (e.g., PEI). In certain embodiments, the HDR promoting agent is complexed with one or more chemical agents to form, e.g., a solution, liposome, micelle, emulsion, reverse emulsion, suspension, colloid, or gel. In any of the aforementioned embodiments, it is further contemplated that genome editing molecules comprising polynucleotides and/or polypeptides can be also be delivered as described above.

In certain embodiments, the physical agent for delivery of gene editing molecules is at least one selected from the group consisting of particles or nanoparticles (e.g., particles or nanoparticles made of materials such as carbon, silicon, silicon carbide, gold, tungsten, polymers, or ceramics) in various size ranges and shapes, magnetic particles or nanoparticles (e.g., silenceMag Magnetotransfection™ agent, OZ Biosciences, San Diego, Calif.), abrasive or scarifying agents, needles or microneedles, matrices, and grids. In certain embodiments, particulates and nanoparticulates are useful in delivery of the gene editing molecules. Useful particulates and nanoparticles include those made of metals (e.g., gold, silver, tungsten, iron, cerium), ceramics (e.g., aluminum oxide, silicon carbide, silicon nitride, tungsten carbide), polymers (e.g., polystyrene, polydiacetylene, and poly(3,4-ethylenedioxythiophene) hydrate), semiconductors (e.g., quantum dots), silicon (e.g., silicon carbide), carbon (e.g., graphite, graphene, graphene oxide, or carbon nanosheets, nanocomplexes, or nanotubes), and composites (e.g., polyvinylcarbazoleigraphene, polystyrene/graphene, platinum/graphene, palladium/graphene nanocomposites). In certain embodiments, such particulates and nanoparticulates are further covalently or non-covalently functionalized, or further include modifiers or cross-linked materials such as polymers (e.g., linear or branched polyethylenimine, polylysine), polynucleotides (e.g., DNA or RNA), polysaccharides, lipids, polyglycols (e.g., polyethylene glycol, thiolated polyethylene glycol), polypeptides or proteins, and detectable labels (e.g., a fluorophore, an antigen, an antibody, or a quantum dot). In various embodiments, such particulates and nanoparticles are neutral, or carry a positive charge, or carry a negative charge. Embodiments of compositions including particulates include those formulated, e.g., as liquids, colloids, dispersions, suspensions, aerosols, gels, and solids. Embodiments include nanoparticles affixed to a surface or support, e.g., an array of carbon nanotubes vertically aligned on a silicon or copper wafer substrate. Embodiments include polynucleotide compositions including particulates (e.g., gold or tungsten or magnetic particles) delivered by a Biolistic-type technique or with magnetic force. The size of the particles used in Biolistics is generally in the "microparticle" range, for example, gold microcarriers in the 0.6, 1.0, and 1.6 micrometer size ranges (see, e.g., instruction manual for the Helios® Gene Gun System, Bio-Rad, Hercules, Calif.; Randolph-Anderson et al. (2015) "Sub-micron gold particles are superior to larger particles for efficient Biolistic® transformation of organelles and some cell types", Bio-Rad US/EG Bulletin 2015), but successful Biolistics delivery using larger (40 nanometer) nanoparticles has been reported in cultured animal cells; see O'Brian and Lummis (2011) *BMC Biotechnol.,* 11:66-71. Other embodiments of useful particulates are nanoparticles, which are generally in the nanometer (nm) size range or less than 1 micrometer, e.g., with a diameter of less than about 1 nm, less than about 3 nm, less than about 5 nm, less than about 10 nm, less than about 20 nm, less than about 40 nm, less than about 60 nm, less than about 80 nm, and less than about 100 nm. Specific, non-limiting embodiments of nanoparticles commercially available (all from Sigma-Aldrich Corp., St. Louis, Mo.) include gold nanoparticles with diameters of 5, 10, or 15 nm; silver nanoparticles with particle sizes of 10, 20, 40, 60, or 100 nm; palladium "nanopowder" of less than 25 nm particle size; single-, double-, and multi-walled carbon nanotubes, e.g., with diameters of 0.7-1.1, 1.3-2.3, 0.7-0.9, or 0.7-1.3 nm, or with nanotube bundle dimensions of 2-10 nm by 1-5 micrometers, 6-9 nm by 5 micrometers, 7-15 nm by 0.5-10 micrometers, 7-12 nm by 0.5-10 micrometers, 110-170 nm by 5-9 micrometers, 6-13 nm by 2.5-20 micrometers. In certain embodiments, physical agents for delivery of gene editing molecules can include materials such as gold, silicon, cerium, or carbon, e.g., gold or gold-coated nanoparticles, silicon carbide whiskers, carborundum, porous silica nanoparticles, gelatin/silica nanoparticles, nanoceria or cerium oxide nanoparticles (CNPs), carbon nanotubes (CNTs) such as single-, double-, or multi-walled carbon nanotubes and their chemically functionalized versions (e.g., carbon nanotubes functionalized with amide, amino, carboxylic acid, sulfonic acid, or polyethylene glycol moeities), and graphene or graphene oxide or graphene complexes. Such physical agents that can be adapted for delivery of gene editing molecules include those disclosed in Wong et al. (2016) *Nano Lett.,* 16:1161-1172; Giraldo et al. (2014) *Nature Materials,* 13:400-409; Shen et al. (2012) *Theranostics,* 2:283-294; Kim et al. (2011) *Bioconjugate Chem.,* 22:2558-2567; Wang et al. (2010) *J. Am. Chem. Soc. Comm.,* 132:9274-9276; Zhao et al. (2016) *Nanoscale Res. Lett.,* 11:195-203; and Choi et al. (2016) *J. Controlled Release,* 235:222-235. See also, for example, the various types of particles and nanoparticles, their preparation, and methods for their use, e.g., in delivering polynucleotides and polypeptides to cells, disclosed in US Patent Application Publications 2010/0311168, 2012/0023619, 2012/0244569, 2013/0145488, 2013/0185823, 2014/0096284, 2015/0040268, 2015/0047074, and 2015/0208663, all of which are incorporated herein by reference in their entirety.

In certain embodiments wherein the gene editing molecules comprise a gRNA (or polynucleotide encoding the gRNA) and/or a donor DNA template is provided in a composition that further includes an RNA-guided nuclease (or a polynucleotide that encodes the same), one or more one chemical, enzymatic, or physical agent can similarly be employed. In certain embodiments, the RNA guide and/or a donor DNA template and RNA-guided nuclease or polynucleotide encoding the same) are provided separately, e.g., in a separate composition. Such compositions can include other chemical or physical agents (e.g., solvents, surfactants, proteins or enzymes, transfection agents, particulates or nanoparticulates), such as those described above as useful in the polynucleotide compositions. For example, porous silica nanoparticles are useful for delivering a DNA recombinase into maize cells; see, e.g., Martin-Ortigosa et al. (2015) *Plant Physiol.,* 164:537-547, and can be adapted to providing a RNA-guided nuclease or polynucleotide encoding the same into a maize or other plant cell. In one embodiment, the polynucleotide composition includes a gRNA and the RNA-guided nuclease, and further includes a surfactant and a cell-penetrating peptide (CPP) which can be operably linked to the. In an embodiment, the polynucleotide composition includes a plasmid or viral vector that encodes both the gRNA and the RNA-guided nuclease, and further includes a surfactant and carbon nanotubes. In an embodiment, the polynucleotide composition includes multiple gRNAs and an mRNA encoding the RNA-guided nuclease, and further includes particles (e.g., gold or tungsten particles), and the polynucleotide composition is delivered to a plant cell or plant protoplast by Biolistics. In any of the aforementioned embodiments, it is further contemplated that other polynucleotides of interest including genome editing molecules can also be delivered before, during, or after delivery of the gRNA and the RNA-guided nuclease.

In certain embodiments, the plant, plant explant, or plant part from which a plant cell is obtained or isolated is treated with one or more chemical, enzymatic, or physical agent(s) in the process of obtaining, isolating, or exposing or treating the plant cell the cell with an HDR promoting agent or a gene editing molecule. In certain embodiments, the plant cell, plant, plant explant, or plant part is treated with an abrasive, a caustic agent, a surfactant such as Silwet L-77 or a cationic lipid, or an enzyme such as cellulase. In any of the aforementioned embodiments, it is further contemplated that other polynucleotides of interest including genome editing molecules can also be delivered before, during, or after delivery of the HDR promoting agents.

In certain embodiments, one or more than one chemical, enzymatic, or physical agent, separately or in combination with (e.g., as a part of) the composition comprising the HDR promoting agent (e.g., a compound of Table 1, a compound of Table 2, any bioactive analog thereof, a plant cell-compatible salt thereof, an ester thereof, and any combination thereof), is provided/applied at a location in the plant or plant part other than the plant location, part, or tissue from which the plant cell is treated, obtained, or isolated. In certain embodiments, the polynucleotide composition is applied to adjacent or distal cells or tissues and is transported (e.g., through the vascular system or by cell-to-cell movement) to the meristem from which plant cells are subsequently isolated. In certain embodiments, the polynucleotide-containing composition is applied by soaking a seed or seed fragment or zygotic or somatic embryo in the composition, whereby the HDR promoting agent is delivered to the plant cell. In certain embodiments, a flower bud or shoot tip is contacted with an HDR promoting agent-containing composition, whereby the polynucleotide is delivered to cells in the flower bud or shoot tip from which desired plant cells are obtained. In certain embodiments, a HDR promoting agent-containing composition is applied to the surface of a plant or of a part of a plant (e.g., a leaf surface), whereby the HDR promoting agents are delivered to tissues of the plant from which desired plant cells are obtained. In certain embodiments a whole plant or plant tissue is subjected to particle- or nanoparticle-mediated delivery (e.g., Biolistics or carbon nanotube or nanoparticle delivery) of a HDR promoting agent-containing composition, whereby the polynucleotide(s) are delivered to cells or tissues from which plant cells are subsequently obtained. In any of the aforementioned embodiments, it is further contemplated that other polynucleotides of interest including genome editing molecules can also be delivered before, during, or after delivery of the HDR promoting agents.

Genome editing molecules include gene editing molecules for inducing a genetic modification in the plant cells having increased HDR-mediated genome modification frequencies provided herein. In certain embodiments, such genome editing molecules can include: (i) a polynucleotide selected from the group consisting of an RNA guide for an RNA-guided nuclease, a DNA encoding an RNA guide for an RNA-guided nuclease; (ii) a nuclease selected from the group consisting of an RNA-guided nuclease, an RNA-guided DNA endonuclease, a type II Cas nuclease, a Cas9, a type V Cas nuclease, a Cas12a, a CasY, a CasX, a Cas12b, a Cas12c, an engineered nuclease, a codon-optimized nuclease, a zinc-finger nuclease (ZFN), a transcription activator-like effector nuclease (TAL-effector nuclease), Argonaute, a meganuclease or engineered meganuclease; (iii) a polynucleotide encoding one or more nucleases capable of effectuating site-specific modification of a target nucleotide sequence; and/or (iv) a donor template DNA molecule. In certain embodiments, at least one delivery agent is selected from the group consisting of solvents, fluorocarbons, glycols or polyols, surfactants; primary, secondary, or tertiary amines and quaternary ammonium salts; organosilicone surfactants; lipids, lipoproteins, lipopolysaccharides; acids, bases, caustic agents; peptides, proteins, or enzymes; cell-penetrating peptides; RNase inhibitors; cationic branched or linear polymers; dendrimers; counter-ions, amines or polyamines, osmolytes, buffers, and salts; polynucleotides; transfection agents; antibiotics; chelating agents such as ammonium oxalate, EDTA, EGTA, or cyclohexane diamine tetraacetate, non-specific DNA double-strand-break-inducing agents; and antioxidants; particles or nanoparticles, magnetic particles or nanoparticles, abrasive or scarifying agents, needles or microneedles, matrices, and grids. In certain embodiments, the eukaryotic cell (e.g., plant cell), system, method, or composition comprising the cells provided herein further includes (a) at least one cell having a Cas9, a Cas12a, a CasY, a CasX, a Cas12b, or a C2c3 nuclease; (b) at least one guide RNA; and (c) optionally, at least one chemical, enzymatic, or physical delivery agent.

Gene editing molecules of use in the cells, systems, methods, compositions, and reaction mixtures provided herein include molecules capable of introducing a double-strand break ("DSB") in double-stranded DNA, such as in genomic DNA or in a target gene located within the genomic DNA as well as accompanying guide RNA or donor template polynucleotides. Examples of such gene editing molecules include: (a) a nuclease selected from the group consisting of an RNA-guided nuclease, an RNA-guided DNA endonuclease, a type II Cas nuclease, a Cas9, a type V Cas nuclease, a Cas12a, a CasY, a CasX, a Cas12b, a Cas12c, an engineered nuclease, a codon-optimized nuclease, a zinc-finger nuclease (ZFN), a transcription activator-like effector nuclease (TAL-effector nuclease), an Argonaute, and a meganuclease or engineered meganuclease; (b) a polynucleotide encoding one or more nucleases capable of effectuating site-specific alteration (such as introduction of a DSB) of a target nucleotide sequence; (c) a guide RNA (gRNA) for an RNA-guided nuclease, or a DNA encoding a gRNA for an RNA-guided nuclease; and (d) donor template polynucleotides.

CRISPR-type genome editing can be adapted for use in the eukaryotic cells (e.g., plant cells), systems, methods, and compositions provided herein in several ways. CRISPR elements, i.e., gene editing molecules comprising CRISPR endonucleases and CRISPR single-guide RNAs or polynucleotides encoding the same, are useful in effectuating genome editing without remnants of the CRISPR elements or selective genetic markers occurring in progeny. In certain embodiments, the CRISPR elements are provided directly to the eukaryotic cell (e.g., plant cells), systems, methods, and compositions as isolated molecules, as isolated or semi-purified products of a cell free synthetic process (e.g., in vitro translation), or as isolated or semi-purified products of in a cell-based synthetic process (e.g., such as in a bacterial or other cell lysate). In certain embodiments, genome-inserted CRISPR elements are useful in plant lines adapted for use in the systems, methods, and compositions provide herein. In certain embodiments, plants or plant cells used in the systems, methods, and compositions provided herein can comprise a transgene that expresses a CRISPR endonuclease (e.g., a Cas9, a 12a-type or other CRISPR endonuclease). In certain embodiments, one or more CRISPR endonucleases with unique PAM recognition sites can be used. Guide RNAs (sgRNAs or crRNAs and a tracrRNA) to form an RNA-guided endonuclease/guide RNA complex which can specifically bind sequences in the gDNA target site that are adjacent to a protospacer adjacent motif (PAM) sequence. The type of RNA-guided endonuclease typically informs the location of suitable PAM sites and design of crRNAs or sgRNAs. C-rich PAM sites, e.g., 5'-NGG are typically targeted for design of crRNAs or sgRNAs used with Cas9 proteins. T-rich PAM sites (e.g., 5'-TTTV [1], where "V" is A, C, or G) are typically targeted for design of crRNAs or sgRNAs used with Cas12a proteins (e.g., SEQ ID NO:1, 2, and 3). PAM sites including TTN, CTN, TCN, CCN, TTTN, TCTN, TTCN, CTTN, ATTN, TCCN, TTGN, GTTN, CCCN, CCTN, TTAN, TCGN, CTCN, ACTN, GCTN, TCAN, GCCN, and CCGN targeted for design of crRNAs or sgRNAs used with CasJ proteins (e.g., SEQ ID NO:4). Cpf1 endonuclease and corresponding guide RNAs and PAM sites are disclosed in US Patent Application Publication 2016/0208243 A1, which is incorporated herein by reference for its disclosure of DNA encoding Cpf1 endonucleases and guide RNAs and PAM sites. Introduction of one or more of a wide variety of CRISPR guide RNAs that interact with CRISPR endonucleases integrated into a plant genome or otherwise provided to a plant is useful for genetic editing for providing desired phenotypes or traits, for trait screening, or for gene editing mediated trait introgression (e.g., for introducing a trait into a new genotype without backcrossing to a recurrent parent or with limited backcrossing to a recurrent parent). Multiple endonucleases can be provided in expression cassettes with the appropriate promoters to allow multiple genome editing in a spatially or temporally separated fashion in either in chromosome DNA or episome DNA.

CRISPR technology for editing the genes of eukaryotes is disclosed in US Patent Application Publications 2016/0138008A1 and US2015/0344912A1, and in U.S. Pat. Nos. 8,697,359, 8,771,945, 8,945,839, 8,999,641, 8,993,233, 8,895,308, 8,865,406, 8,889,418, 8,871,445, 8,889,356, 8,932,814, 8,795,965, and 8,906,616. Cpf1 endonuclease and corresponding guide RNAs and PAM sites are disclosed in US Patent Application Publication 2016/0208243 A1. Other CRISPR nucleases useful for editing genomes include Cas12b and Cas12c (see Shmakov et al. (2015) *Mol. Cell*, 60:385-397) and CasX and CasY (see Burstein et al. (2016) *Nature*, doi:10.1038/nature21059). Plant RNA promoters for expressing CRISPR guide RNA and plant codon-optimized CRISPR Cas9 endonuclease are disclosed in International Patent Application PCT/US2015/018104 (published as WO 2015/131101 and claiming priority to U.S. Provisional Patent Application 61/945,700). Methods of using CRISPR technology for genome editing in plants are disclosed in US Patent Application Publications US 2015/0082478A1 and US 2015/0059010A1 and in International Patent Application PCT/US2015/038767 A1 (published as WO 2016/007347 and claiming priority to U.S. Provisional Patent Application 62/023,246). All of the patent publications referenced in this paragraph are incorporated herein by reference in their entirety.

For the purposes of gene editing, CRISPR arrays can be designed to contain one or multiple guide RNA sequences corresponding to a desired target DNA sequence; see, for example, Cong et al. (2013) *Science,* 339:819-823; Ran et al. (2013) *Nature Protocols,* 8:2281-2308. At least 16 or 17 nucleotides of gRNA sequence are required by Cas9 for DNA cleavage to occur; for Cpf1 at least 16 nucleotides of gRNA sequence are needed to achieve detectable DNA cleavage and at least 18 nucleotides of gRNA sequence were reported necessary for efficient DNA cleavage in vitro; see Zetsche et al. (2015) *Cell,* 163:759-771. In practice, guide RNA sequences are generally designed to have a length of 17-24 nucleotides (frequently 19, 20, or 21 nucleotides) and exact complementarity (i.e., perfect base-pairing) to the targeted gene or nucleic acid sequence; guide RNAs having less than 100% complementarity to the target sequence can be used (e.g., a gRNA with a length of 20 nucleotides and 1-4 mismatches to the target sequence) but can increase the potential for off-target effects. The design of effective guide RNAs for use in plant genome editing is disclosed in US Patent Application Publication 2015/0082478 A1, the entire specification of which is incorporated herein by reference. More recently, efficient gene editing has been achieved using a chimeric "single guide RNA" ("sgRNA"), an engineered (synthetic) single RNA molecule that mimics a naturally occurring crRNA-tracrRNA complex and contains both a tracrRNA (for binding the nuclease) and at least one crRNA (to guide the nuclease to the sequence targeted for editing); see, for example, Cong et al. (2013) *Science,* 339:819-823; Xing et al. (2014) *BMC Plant Biol.,* 14:327-340. Chemically modified sgRNAs have been demonstrated to be effective in genome editing; see, for example, Hendel et al. (2015) *Nature Biotechnol.,* 985-991. The design of effective gRNAs for use in plant genome editing is disclosed in US Patent Application Publication 2015/0082478 A1, the entire specification of which is incorporated herein by reference.

Other sequence-specific endonucleases capable of effecting site-specific modification of a target nucleotide sequence in the systems, methods, and compositions provided herein include zinc-finger nucleases (ZFNs), transcription activator-like effector nucleases (TAL-effector nucleases or TAL-ENs), Argonaute proteins, and a meganuclease or engineered meganuclease. Zinc finger nucleases (ZFNs) are engineered proteins comprising a zinc finger DNA-binding domain fused to a nucleic acid cleavage domain, e.g., a nuclease. The zinc finger binding domains provide specificity and can be engineered to specifically recognize any desired target DNA sequence. For a review of the construction and use of ZFNs in plants and other organisms, see, e.g., Urnov et al. (2010) *Nature Rev. Genet.,* 11:636-646. The zinc finger DNA binding domains are derived from the DNA-binding domain of a large class of eukaryotic transcription factors called zinc finger proteins (ZFPs). The DNA-binding domain of ZFPs typically contains a tandem array of at least three zinc "fingers" each recognizing a specific triplet of DNA. A number of strategies can be used to design the binding specificity of the zinc finger binding domain. One approach, termed "modular assembly", relies on the functional autonomy of individual zinc fingers with DNA. In this approach, a given sequence is targeted by identifying zinc fingers for each component triplet in the sequence and linking them into a multifinger peptide. Several alternative strategies for designing zinc finger DNA binding domains have also been developed. These methods are designed to accommodate the ability of zinc fingers to contact neighboring fingers as well as nucleotide bases outside their target triplet. Typically, the engineered zinc finger DNA binding domain has a novel binding specificity, compared to a naturally-occurring zinc finger protein. Engineering methods include, for example, rational design and various types of selection. Rational design includes, for example, the use of databases of triplet (or quadruplet) nucleotide sequences and individual zinc finger amino acid sequences, in which each triplet or quadruplet nucleotide sequence is associated with one or more amino acid sequences of zinc fingers which bind the particular triplet or quadruplet sequence. See, e.g., U.S. Pat. Nos. 6,453,242 and 6,534,261, both incorporated herein by reference in their entirety. Exemplary selection methods (e.g., phage display and yeast two-hybrid systems) are well known and described in the literature. In addition, enhancement of binding specificity for zinc finger binding domains has been described in U.S. Pat. No. 6,794,136, incorporated herein by reference in its entirety. In addition, individual zinc finger domains may be linked together using any suitable linker sequences. Examples of linker sequences are publicly known, e.g., see U.S. Pat. Nos. 6,479,626; 6,903,185; and 7,153,949, incorporated herein by reference in their entirety. The nucleic acid cleavage domain is non-specific and is typically a restriction endonuclease, such as FokI. This endonuclease must dimerize to cleave DNA. Thus, cleavage by FokI as part of a ZFN requires two adjacent and independent binding events, which must occur in both the correct orientation and with appropriate spacing to permit dimer formation. The requirement for two DNA binding events enables more specific targeting of long and potentially unique recognition sites. FokI variants with enhanced activities have been described; see, e.g., Guo et al. (2010) *J. Mol. Biol.,* 400:96-107.

Transcription activator like effectors (TALEs) are proteins secreted by certain *Xanthomonas* species to modulate gene expression in host plants and to facilitate the colonization by and survival of the bacterium. TALEs act as transcription factors and modulate expression of resistance genes in the plants. Recent studies of TALEs have revealed the code linking the repetitive region of TALEs with their target DNA-binding sites. TALEs comprise a highly conserved and repetitive region consisting of tandem repeats of mostly 33 or 34 amino acid segments. The repeat monomers differ from each other mainly at amino acid positions 12 and 13. A strong correlation between unique pairs of amino acids at positions 12 and 13 and the corresponding nucleotide in the TALE-binding site has been found. The simple relationship between amino acid sequence and DNA recognition of the TALE binding domain allows for the design of DNA binding domains of any desired specificity. TALEs can be linked to a non-specific DNA cleavage domain to prepare sequence-specific endonucleases referred to as TAL-effector nucleases or TALENs. As in the case of ZFNs, a restriction endonuclease, such as FokI, can be conveniently used. For a description of the use of TALENs in plants, see Mahfouz et al. (2011) *Proc. Natl. Acad. Sci. USA,* 108:2623-2628 and Mahfouz (2011) *GM Crops,* 2:99-103.

Argonautes are proteins that can function as sequence-specific endonucleases by binding a polynucleotide (e.g., a single-stranded DNA or single-stranded RNA) that includes sequence complementary to a target nucleotide sequence) that guides the Argonaut to the target nucleotide sequence and effects site-specific alteration of the target nucleotide sequence; see, e.g., US Patent Application Publication 2015/0089681, incorporated herein by reference in its entirety.

Donor template DNA molecules used in the methods, systems, eukaryotic cells (e.g., plant cells), and compositions provided herein include DNA molecules comprising, from 5' to 3', a first homology arm, a replacement DNA, and a second homology arm, wherein the homology arms containing sequences that are partially or complete homologous to genomic DNA (gDNA) sequences flanking a target site-specific endonuclease cleavage site in the gDNA and wherein the replacement DNA can comprise an insertion, deletion, or substitution of 1 or more DNA base pairs relative to the target gDNA. In certain embodiments, a donor DNA template homology arm can be about 200, 400, or 600 to about 800, or 1000 base pairs in length. In certain embodiments, a donor template DNA molecule can be delivered to a eukaryotic cell (e.g., a plant cell) in a circular (e.g., a plasmid or a viral vector including a geminivirus vector) or a linear DNA molecule. Donor DNA templates can be synthesized either chemically or enzymatically (e.g., in a polymerase chain reaction (PCR)).

Other genome editing molecules used in plant cells and methods provided herein include transgenes or vectors comprising the same. Such transgenes can confer useful traits that include herbicide tolerance, pest tolerance (e.g., tolerance to insects, nematodes, or plant pathogenic fungi and bacteria), unproved yield, increased and/or qualitatively improved oil, starch, and protein content, improved abiotic stress tolerance (e.g., improved or enhanced water use efficiency or drought tolerance, osmotic stress tolerance, high salinity stress tolerance, heat stress tolerance, enhanced cold tolerance, including cold germination tolerance), and the like. Such transgenes include both transgenes that confer the trait by expression of an exogenous protein as well as transgenes that confer the trait by inhibiting expression of endogenous plant genes (e.g., by inducing an siRNA response which inhibits expression of the endogenous plant genes). Transgenes that can provide such traits are disclosed in US Patent Application Publication Nos. 20170121722 and 20170275636, which are each incorporated herein by reference in their entireties and specifically with respect to such disclosures.

In some embodiments, one or more polynucleotides or vectors driving expression of one or more polynucleotides encoding any of the aforementioned HDR promoting agents and/or genome editing molecules are introduced into a eukaryotic cell (e.g., plant cell). In certain embodiments, a polynucleotide vector comprises a regulatory element such as a promoter operably linked to one or more polynucleotides encoding HDR promoting agents or genome editing molecules. In such embodiments, expression of these polynucleotides can be controlled by selection of the appropriate promoter, particularly promoters functional in a eukaryotic cell (e.g., plant cell); useful promoters include constitutive, conditional, inducible, and temporally or spatially specific promoters (e.g., a tissue specific promoter, a developmentally regulated promoter, or a cell cycle regulated promoter). Developmentally regulated promoters that can be used in plant cells include Phospholipid Transfer Protein (PLTP), fructose-1,6-bisphosphatase protein, NAD(P)-binding Rossmann-Fold protein, adipocyte plasma membrane-associated protein-like protein, Rieske [2Fe-2S] iron-sulfur domain protein, chlororespiratory reduction 6 protein, D-glycerate 3-kinase, chloroplastic-like protein, chlorophyll a-b binding protein 7, chloroplastic-like protein, ultraviolet-B-repressible protein, Soul heme-binding family protein, Photosystem I reaction center subunit psi-N protein, and short-chain dehydrogenase/reductase protein that are disclosed in US Patent Application Publication No. 20170121722, which is incorporated herein by reference in its entirety and specifically with respect to such disclosure. In certain embodiments, the promoter is operably linked to nucleotide sequences encoding multiple guide RNAs, wherein the sequences encoding guide RNAs are separated by a cleavage site such as a nucleotide sequence encoding a microRNA recognition/cleavage site or a self-cleaving ribozyme (see, e.g., Ferré-D'Amaré and Scott (2014) *Cold Spring Harbor Perspectives Biol.,* 2:a003574). In certain embodiments, the promoter is an RNA polymerase III promoter operably linked to a nucleotide sequence encoding one or more guide RNAs. In certain embodiments, the promoter operably linked to one or more polynucleotides is a constitutive promoter that drives gene expression in eukaryotic cells (e.g., plant cells). In certain embodiments, the promoter drives gene expression in the nucleus or in an organelle such as a chloroplast or mitochondrion. Examples of constitutive promoters for use in plants include a CaMV 35S promoter as disclosed in U.S. Pat. Nos. 5,858,742 and 5,322,938, a rice actin promoter as disclosed in U.S. Pat. No. 5,641,876, a maize chloroplast aldolase promoter as disclosed in U.S. Pat. No. 7,151,204, and the nopaline synthase (NOS) and octopine synthase (OCS) promoters from *Agrobacterium tumefaciens*. In certain embodiments, the promoter operably linked to one or more polynucleotides encoding elements of a genome-editing system is a promoter from figwort mosaic virus (FMV), a RUBISCO promoter, or a pyruvate phosphate dikinase (PPDK) promoter, which is active in photosynthetic tissues. Other contemplated promoters include cell-specific or tissue-specific or developmentally regulated promoters, for example, a promoter that limits the expression of the nucleic acid targeting system to germline or reproductive cells (e.g., promoters of genes encoding DNA ligases, recombinases, replicases, or other genes specifically expressed in germline or reproductive cells). In certain embodiments, the genome alteration is limited only to those cells from which DNA is inherited in subsequent generations, which is advantageous where it is desirable that expression of the genome-editing system be limited in order to avoid genotoxicity or other unwanted effects. All of the patent publications referenced in this paragraph are incorporated herein by reference in their entirety.

Expression vectors or polynucleotides provided herein may contain a DNA segment near the 3' end of an expression cassette that acts as a signal to terminate transcription and directs polyadenylation of the resultant mRNA, and may also support promoter activity. Such a 3' element is commonly referred to as a "3'-untranslated region" or "3'-UTR" or a "polyadenylation signal." In some cases, plant gene-based 3' elements (or terminators) consist of both the 3'-UTR and downstream non-transcribed sequence (Nuccio et al., 2015). Useful 3' elements include: *Agrobacterium tumefaciens* nos 3', tml 3', tmr 3', tms 3', ocs 3', and tr7 3' elements disclosed in U.S. Pat. No. 6,090,627, incorporated herein by reference, and 3' elements from plant genes such as the heat shock protein 17, ubiquitin, and fructose-1,6-biphosphatase genes from wheat (*Triticum aestivum*), and the glutelin, lactate dehydrogenase, and beta-tubulin genes from rice (*Oryza sativa*), disclosed in US Patent Application Publication 2002/0192813 A1, incorporated herein by reference.

In certain embodiments, a vector or polynucleotide comprising an expression cassette includes additional components, e.g., a polynucleotide encoding a drug resistance or herbicide gene or a polynucleotide encoding a detectable marker such as green fluorescent protein (GFP) or beta-glucuronidase (gus) to allow convenient screening or selection of cells expressing the vector or polynucleotide. Selectable markers include genes that confer resistance to herbicidal compounds, such as glyphosate, sulfonylureas, glufosinate ammonium, bromoxynil, imidazolinones, and 2,4-dichlorophenoxyacetate (2,4-D). Such selectable marker genes and selective agents include the maize HRA gene (Lee et al., 1988, EMBO J 7:1241-1248) which confers resistance to sulfonylureas and imidazolinones, the CP4 gene that confers resistance to glyphosate (U.S. Reissue patent RE039247, specifically incorporated herein by reference in its entirety and with respect to such genes and related selection methods), the GAT gene which confers resistance to glyphosate (Castle et al., 2004, Science 304:1151-1154), genes that confer resistance to spectinomycin such as the aadA gene (Swab et al., 1990, Plant Mol Biol. 14:197-205) and the bar gene that confers resistance to glufosinate ammonium (White et al., 1990, Nucl. Acids Res. 25:1062), and PAT (or moPAT for corn, see Rasco-Gaunt et al., 2003, Plant Cell Rep. 21:569-76; also see Sivamani et al., 2019) and the PMI gene that permits growth on mannose-containing medium (Negrotto et al., 2000, Plant Cell Rep. 22:684-690).

In certain embodiments, a counter-selectable marker can be used in the eukaryotic cells (e.g., plant), methods, systems, and compositions provided herein. Such counter-selectable markers can in certain embodiments be incorporated into any DNA that is not intended for insertion into a host cell genome ar target editing sites. In such embodiments, non-limiting examples of DNAs with counter-selectable markers include any DNA molecules that are linked to DNAs encoding gene-editing molecules, and/or donor template DNA molecules. Vectors or DNA molecules comprising donor template DNA molecules wherein the counter-selectable marker is linked to the donor template DNA and optionally separated from the donor template DNA by a target editing site sequence. Examples of counter-selectable markers that can be used in Plants include cytosine deaminase genes (e.g., used in conjunction with 5-fluorocytosine; Schlaman and Hooykaas, 1997), phosphonate ester hydrolases (e.g., used in conjunction with phosphonate esters of glyphosate including glycerol glyphosate; Dotson, et al. 1996), a nitrate reductase (e.g., used in conjunction with chlorate on media containing ammonia as a sole nitrogen source; Nussaume, et al. 1991).

In certain embodiments, the use of a selectable marker is obviated by the increased frequency of HDR provided by the HDR promoting agents (i.e., HDR promoting agents). In such embodiments, a selectable marker and/or a counter-selectable marker can be omitted from any of a donor template DNA molecule, a plasmid used to deliver a donor-template or other DNA molecule, or any other vector (e.g., viral vector) or polynucleotide used in the cells, system, method, or composition provided herein.

EMBODIMENTS

Various embodiments of the eukaryotic cells (e.g., plant cells), systems, and methods provided herein are included in the following non-limiting list of embodiments.

1. A method for increasing Homology Directed Repair (HDR)-mediated genome modification of a plant cell genome, comprising:
  providing genome editing molecules to a plant cell,
  wherein the plant cell is exposed to an effective concentration of a composition comprising at least one HDR promoting agent selected from the group consisting of a 5-substituted 2,4-oxazolidinedione, a 5-substituted 2,4-thiazolidinedione, CAS No. 102649-78-5, CAS No. 128-20-1, CAS No. 549505-65-9, CAS No. 1596-84-5, CAS No. 940929-33-9, CAS No. 336113-53-2, CAS No. 146-77-0, CAS No. 28822-58-4, CAS No. 477845-12-8, CAS No. 872573-93-8, CAS No. 724741-75-7, CAS No. 1357171-62-0, CAS No. 715934-43-2, any bioactive analog thereof, a plant cell-compatible salt thereof, an ester thereof, and any combination thereof;
  wherein the genome editing molecules comprise an RNA-guided nuclease or a polynucleotide encoding an RNA-guided nuclease, a guide RNA or a polynucleotide encoding a guide RNA, and a donor template DNA molecule;
  whereby the genome editing molecules modify the plant cell genome by HDR at a frequency that is increased in comparison to a control method wherein a control plant cell is provided with the genome editing molecules but is not exposed to at least one of said HDR promoting agents or any combination thereof.

2. The method of embodiment 1, wherein the frequency of HDR is increased by at least 1.5-fold, at least 2-fold, or at least 3-fold in comparison to the control method wherein a control plant cell is provided with the genome editing molecules but is not exposed to at least one of said HDR promoting agents or any combination thereof.

3. The method of embodiment 1 or 2, wherein the plant cell is haploid, diploid, or polyploid.

4. The method of any one of embodiments 1 to 3, wherein the plant cell is in a culture medium, in a plant, or in a plant tissue.

5. The method of any one of embodiments 1 to 4, wherein the level of at least one oxygen species is lowered in the plant cell by exposure of the plant cell to a hypoxic condition, or by exposure of the plant cell to at least one reactive oxygen species (ROS) concentration lowering agent, or by exposure of the plant cell to both a hypoxic condition and to at least one ROS concentration lowering agent.

6. The method of embodiment 5, wherein the hypoxic condition comprises maintaining the cell in air comprising an oxygen concentration of about 12% to about 5% oxygen by volume, or wherein the cell is in a liquid culture medium and the hypoxic condition comprises maintaining the cell and the medium in air comprising an oxygen concentration of about 12% to about 5% oxygen by volume.

7. The method of embodiment 5 or 6, wherein the reactive oxygen species (ROS) concentration lowering agent comprises an exogenously provided enzymatic ROS scavenging agent or an exogenously provided non-enzymatic ROS scavenging agent or a combination thereof.

8. The method of any one of embodiments 5 to 7, wherein the HDR promoting agent is selected from the group consisting of a 5-substituted 2,4-oxazolidinedione, a 5-substituted 2, 4-thiazolidinedione, CAS No. 102649-78-5, CAS No. 549505-65-9, CAS No. 336113-53-2, CAS No. 146-77-0, CAS No. 28822-58-4, CAS No. 477845-12-8, CAS No. 872573-93-8, CAS No. 724741-75-7, CAS No. 1357171-62-0, CAS No. 715934-43-2, any bioactive analog thereof, a plant cell-compatible salt thereof, an ester thereof, and any combination thereof.

9. The method of embodiment 8, wherein the 5-substituted 2, 4-thiazolidinedione is selected from the group consisting of Rosiglitazone (CAS No. 122320-73-4), Edaglitazone (CAS No. 213411-83-7), Ciglitazone (CAS No. 74772-77-3), Lobeglitazone (CAS No. 607723-33-1), Pioglitazone hydrochloride (CAS No. 112529-15-4), Troglitazone (CAS No. 97322-87-7), Mitoglitazone (CAS No. 146062-49-9), Darglitazone (CAS No. 141200-24-0), Englitazone (CAS No. 109229-58-5), Netoglitazone (CAS No. 161600-01-7), Rivoglitazone (CAS No. 185428-18-6), Balaglitazone (CAS No. 199113-98-9), and a plant cell-compatible salt thereof.

10. The method of any one of embodiments 1 to 4, wherein the HDR-promoting agent is a 5-substituted 2, 4-thiazolidinedione.

11. The method of embodiment 10, wherein the 5-substituted 2, 4-thiazolidinedione is selected from the group consisting of Rosiglitazone (CAS No. 122320-73-4), Edaglitazone (CAS No. 213411-83-7), Ciglitazone (CAS No. 74772-77-3), Lobeglitazone (CAS No. 607723-33-1), Pioglitazone hydrochloride (CAS No. 112529-15-4), Troglitazone (CAS No. 97322-87-7), Mitoglitazone (CAS No. 146062-49-9), Darglitazone (CAS No. 141200-24-0), Englitazone (CAS No. 109229-58-5). Netoglitazone (CAS No. 161600-01-7), Rivoglitazone (CAS No. 185428-18-6), Balaglitazone (CAS No. 199113-98-9), and a plant cell-compatible salt thereof.

12. The method of any one of embodiments 1 to 11, wherein a bioactive analog thereof is:
    (i) a substitution of a halogen with another halogen;
    (ii) a substitution of a C1 to C6 alkyl group or a C1 to C6 alkoxy group with a different C1 to C6 alkyl group or a different C1 to C6 alkoxy group, respectively;
    (iii) a substitution of an unsubstituted phenyl group with a substituted phenyl group, wherein optionally the substitutions in the phenyl group are selected from a methyl, an alkoxy, aminoalkyl, or halogen; and/or,
    (iv) a substitution of a substituted phenyl group with a different substituted phenyl group wherein optionally the substitutions in the phenyl group are selected from a methyl, an alkoxy, aminoalkyl, or halogen.

13. The method of any one of embodiments 1 to 11, wherein the composition comprising the HDR promoting agent further comprises an agriculturally acceptable adjuvant and/or excipient.

14. The method of any one of embodiments 1 to 11, wherein the plant cell is contained or supported by a plant cell culture medium and Ca2+ and/or Mg2+ is provided in the plant cell culture medium at a concentration of about 40 mM to 150 mM.

15. The method of any one of embodiments 1 to 11, further comprising the step of isolating and/or growing a plant cell, propagule, or plant obtained from the plant cell comprising the genomic modification, wherein the genome of the plant cell, propagule, or plant comprises the genomic modification.

16. A system for modification of a plant gene, comprising:
    (a) a plant cell;
    (b) at least one HDR promoting agent selected from the group consisting of a 5-substituted 2,4-oxazolidinedione, a 5-substituted 2, 4-thiazolidinedione, CAS No. 102649-78-5. CAS No. 128-20-1, CAS No. 549505-65-9, CAS No. 1596-84-5, CAS No. 940929-33-9, CAS No. 336113-53-2, CAS No. 146-77-0, CAS No. 28822-58-4, CAS No. 477845-12-8, CAS No. 872573-93-8, CAS No. 724741-75-7, CAS No. 1357171-62-0, CAS No. 715934-43-2, any bioactive analog thereof, a plant cell-compatible salt thereof, an ester thereof, and any combination thereof; and
    (c) genome editing molecule(s) comprising: an RNA-guided nuclease or a polynucleotide encoding an RNA-guided nuclease, a guide RNA or a polynucleotide encoding a guide RNA, and a donor template DNA molecule;
    (d) wherein the plant cell is associated with, contacts, and/or contains an effective amount of the HDR promoting agent and the genome editing molecule(s).

17. The system of embodiment 16, wherein the plant cell is haploid, diploid, or polyploid.

18. The system of embodiment 16 or 17, wherein the plant cell is in a culture medium, in a plant, or in a plant tissue.

19. The system of any one of embodiments 16 to 18, wherein the level of at least one oxygen species is lowered in the plant cell by exposure of the plant cell to a hypoxic condition, or by exposure of the plant cell to at least one reactive oxygen species (ROS) concentration lowering agent, or by exposure of the plant cell to both a hypoxic condition and to at least one ROS concentration lowering agent.

20. The system of embodiment 19, wherein the hypoxic condition comprises maintaining the cell in air comprising an oxygen concentration of about 12% to about 5% oxygen by volume, or wherein the cell is in a liquid culture medium and the hypoxic condition comprises maintaining the cell and the medium in air comprising an oxygen concentration of about 12% to about 5% oxygen by volume.

21. The system of embodiment 19, wherein the reactive oxygen species (ROS) concentration lowering agent comprises an exogenously provided enzymatic ROS scavenging agent or an exogenously provided non-enzymatic ROS scavenging agent or a combination thereof.

22. The system of any one of embodiments 19 to 21, wherein the HDR promoting agent is selected from the group consisting of a 5-substituted 2,4-oxazolidinedione, a 5-substituted 2, 4-thiazolidinedione, CAS No. 102649-78-5, CAS No. 549505-65-9, CAS No. 336113-53-2, CAS No. 146-77-0, CAS No. 28822-58-4, CAS No. 477845-12-8, CAS No. 872573-93-8, CAS No. 724741-75-7, CAS No. 1357171-62-0, CAS No. 715934-43-2, any bioactive analog thereof, a plant cell-compatible salt thereof, an ester thereof, and any combination thereof.

23. The system of embodiment 22, wherein the 5-substituted 2, 4-thiazolidinedione is selected from the group consisting of Rosiglitazone (CAS No. 122320-73-4), Edaglitazone (CAS No. 213411-83-7), Ciglitazone (CAS No. 74772-77-3), Lobeglitazone (CAS No. 607723-33-1), Pioglitazone hydrochloride (CAS No. 112529-15-4), Troglitazone (CAS No. 97322-87-7), Mitoglitazone (CAS No. 146062-49-9), Darglitazone (CAS No. 141200-24-0), Englitazone (CAS No. 109229-58-5), Netoglitazone (CAS No. 161600-01-7), Rivoglitazone (CAS No. 185428-18-6), Balaglitazone (CAS No. 199113-98-9), and a plant cell-compatible salt thereof.

24. The system of any one of embodiments 16 to 18, wherein the HDR-promoting agent is a 5-substituted 2, 4-thiazolidinedione.

25. The system of embodiment 24, wherein the 5-substituted 2, 4-thiazolidinedione is selected from the group consisting of Rosiglitazone (CAS No. 122320-73-4), Edaglitazone (CAS No. 213411-83-7), Ciglitazone (CAS No. 74772-77-3), Lobeglitazone (CAS No. 607723-33-1), Pioglitazone hydrochloride (CAS No. 112529-15-4), Troglitazone (CAS No. 97322-87-7), Mitoglitazone (CAS No. 146062-49-9), Darglitazone (CAS No. 141200-24-0), Englitazone (CAS No. 109229-58-5), Netoglitazone (CAS No. 161600-01-7), Rivoglitazone (CAS No. 185428-18-6), Balaglitazone (CAS No. 199113-98-9), a bioactive analog thereof, and a plant cell-compatible salt thereof.

26. The system of any one of embodiments 16 to 25, wherein a bioactive analog thereof is:
  (i) a substitution of a halogen with another halogen;
  (ii) a substitution of a C1 to C6 alkyl group or a C1 to C6 alkoxy group with a different C1 to C6 alkyl group or a different C1 to C6 alkoxy group, respectively;
  (iii) a substitution of an unsubstituted phenyl group with a substituted phenyl group, wherein optionally the substitutions in the phenyl group are selected from a methyl, an alkoxy, aminoalkyl, or halogen; and/or,
  (iv) a substitution of a substituted phenyl group with a different substituted phenyl group wherein optionally the substitutions in the phenyl group are selected from a methyl, an alkoxy, aminoalkyl, or halogen.

27. The system of any one of embodiments 16 to 25, wherein the plant cell is contained or supported by a plant cell culture medium and Ca2+ and/or Mg2+ is provided in the plant cell culture medium at a concentration of about 40 mM to 150 mM.

28. The system of any one of embodiments 16 to 25, wherein the composition comprising the HDR promoting agent further comprises an agriculturally acceptable adjuvant and/or excipient.

29. A method for making a plant cell having a genomic modification, comprising:
  (a) providing genome editing molecules to a plant cell, wherein the plant cell is exposed to an effective amount of at least one HDR promoting agent selected from the group consisting of a 5-substituted 2,4-oxazolidinedione, a 5-substituted 2, 4-thiazolidinedione, CAS No. 102649-78-5, CAS No. 128-20-1, CAS No. 549505-65-9, CAS No. 1596-84-5, CAS No. 940929-33-9, CAS No. 336113-53-2, CAS No. 146-77-0, CAS No. 28822-58-4, CAS No. 477845-12-8, CAS No. 872573-93-8, CAS No. 724741-75-7, CAS No. 1357171-62-0, CAS No. 715934-43-2, any bioactive analog thereof, a plant cell-compatible salt thereof, an ester thereof, and any combination thereof;
  wherein the genome editing molecules comprise an RNA-guided nuclease or a polynucleotide encoding an RNA-guided nuclease, a guide RNA or a polynucleotide encoding a guide RNA, and a donor template DNA molecule;
  (b) whereby the genome editing molecules modify the plant cell genome by homology directed repair (HDR) at a frequency that is increased in comparison to a control; and isolating or propagating a plant cell comprising the genome modification, thereby making the plant cell having a genomic modification.

30. The method of embodiment 29, wherein the genome modification comprises homology directed repair (HDR) of the plant cell genome.

31. The method of embodiment 29 or 30, wherein the frequency of HDR is increased by at least 1.5-fold, 2-fold, or 3-fold in comparison to a control method wherein a control plant cell is provided with the genome editing molecules but is not exposed to the HDR promoting agent.

32. The method of any one of embodiments 29 to 31, wherein the plant cell is haploid, diploid, or polyploid.

33. The method of any one of embodiments 29 to 32, wherein the plant cell is in a culture medium, in a plant, or in a plant tissue.

34. The method of any one of embodiments 29 to 33, wherein the level of at least one oxygen species is lowered in the plant cell by exposure of the plant cell to a hypoxic condition, or by exposure of the plant cell to at least one reactive oxygen species (ROS) concentration lowering agent, or by exposure of the plant cell to both a hypoxic condition and to at least one ROS concentration lowering agent.

35. The method of embodiment 34, wherein the hypoxic condition comprises maintaining the cell in air comprising an oxygen concentration of about 12% to about 5% oxygen by volume, or wherein the cell is in a liquid culture medium and the hypoxic condition comprises maintaining the cell and the medium in air comprising an oxygen concentration of about 12% to about 5% oxygen by volume.

36. The method of embodiment 34, wherein the reactive oxygen species (ROS) concentration lowering agent comprises an exogenously provided enzymatic ROS scavenging agent or an exogenously provided non-enzymatic ROS scavenging agent or a combination thereof.

37. The method of any one of embodiments 34 to 36, wherein the HDR promoting agent is selected from the group consisting of a 5-substituted 2,4-oxazolidinedione, a 5-substituted 2, 4-thiazolidinedione, CAS No. 102649-78-5, CAS No. 549505-65-9, CAS No. 336113-53-2, CAS No. 146-77-0, CAS No. 28822-58-4, CAS No. 477845-12-8, CAS No. 872573-93-8, CAS No. 724741-75-7, CAS No. 1357171-62-0, CAS No. 715934-43-2, any bioactive analog thereof, a plant cell-compatible salt thereof, an ester thereof, and any combination thereof.

38. The method of embodiment 37, wherein the 5-substituted 2, 4-thiazolidinedione is selected from the group consisting of Rosiglitazone (CAS No. 122320-73-4), Edaglitazone (CAS No. 213411-83-7), Ciglitazone (CAS No. 74772-77-3), Lobeglitazone (CAS No. 607723-33-1), Pioglitazone hydrochloride (CAS No. 112529-15-4), Troglitazone (CAS No. 97322-87-7), Mitoglitazone (CAS No. 146062-49-9), Darglitazone (CAS No. 141200-24-0), Englitazone (CAS No. 109229-58-5), Netoglitazone (CAS No. 161600-01-7), Rivoglitazone (CAS No. 185428-18-6), Balaglitazone (CAS No. 199113-98-9), and a plant cell-compatible salt thereof.

39. The method of any one of embodiments 29 to 33, wherein the HDR-promoting agent is a 5-substituted 2, 4-thiazolidinedione.

40. The method of embodiment 39, wherein the 5-substituted 2, 4-thiazolidinedione is selected from the group consisting of Rosiglitazone (CAS No. 122320-73-4), Edaglitazone (CAS No. 213411-83-7), Ciglitazone (CAS No. 74772-77-3), Lobeglitazone (CAS No. 607723-33-1), Pioglitazone hydrochloride (CAS No. 112529-15-4), Troglitazone (CAS No. 97322-87-7), Mitoglitazone (CAS No. 146062-49-9), Darglitazone (CAS No. 141200-24-0), Englitazone (CAS No. 109229-58-5), Netoglitazone (CAS No. 161600-01-7), Rivoglitazone (CAS No. 185428-18-6), Balaglitazone (CAS No. 199113-98-9), and a plant cell-compatible salt thereof.

41. The method of any one of embodiments 29 to 40, wherein a bioactive analog thereof is:
  (i) a substitution of a halogen with another halogen;
  (ii) a substitution of a C1 to C6 alkyl group or a C1 to C6 alkoxy group with a different C1 to C6 alkyl group or a different C1 to C6 alkoxy group, respectively;
  (iii) a substitution of an unsubstituted phenyl group with a substituted phenyl group, wherein optionally the substitutions in the phenyl group are selected from a methyl, an alkoxy, aminoalkyl, or halogen; and/or, (iv) a substitution of a substituted phenyl group with a different substituted phenyl group wherein optionally the substitutions in the phenyl group are selected from a methyl, an alkoxy, aminoalkyl, or halogen.

42. The method of any one of embodiments 29 to 40, wherein the plant cell in at least step (a) is contained or supported by a plant cell culture medium and $Ca^{2+}$ and/or $Mg^{2+}$ is provided in the plant cell culture medium at a concentration of about 40 mM to 150 mM.

43. The method of any one of embodiments 29 to 40, wherein the composition comprising the HDR promoting agent further comprises an agriculturally acceptable adjuvant and/or excipient.

44. The method of any one of embodiments 29 to 40, further comprising the step of isolating and/or growing a plant cell, propagule, or plant obtained from the plant cell comprising the genomic modification, wherein the genome of the plant cell, propagule, or plant comprises the genomic modification.

45. The method of any one of embodiments 1 to 15 or 29 to 44, wherein the effective concentration of the HDR-promoting agent is about 0.1 µM, 0.25 µM, 0.5 µM, or 1 µM to about 10 µM, 25 µM, 50 µM, 100 µM, or 500 µM.

46. The method of embodiment 45, wherein the effective concentration of the HDR-promoting agent is about 0.5 µM or 1 µM to about 10 µM, 25 µM, or 50 µM.

47. The system of any one of embodiments 16 to 28, wherein the effective concentration of the HDR-promoting agent is about 0.1 µM, 0.25 µM, 0.5 µM, or about 1 µM to about 10 µM, 25 µM, 50 µM, 100 µM, or 500 µM.

48. The system of embodiment 47, wherein the effective concentration of the HDR-promoting agent is about 0.1 µM, 0.05 µM, or 1 µM to about 10 µM, 25 µM, or 50 µM.

49. The system of any one of embodiments 16 to 28, 47, or 48, wherein the plant cell is contacted with a ROS concentration lowering agent, wherein the plant cell is in a hypoxic medium and/or medium comprising a ROS concentration lowering agent, or wherein the system is maintained under hypoxic conditions.

50. A composition comprising:
    (a) a plant cell;
    (b) at least one HDR promoting agent selected from the group consisting of a 5-substituted 2,4-oxazolidinedione, a 5-substituted 2, 4-thiazolidinedione, CAS No. 102649-78-5, CAS No. 128-20-1, CAS No. 549505-65-9, CAS No. 1596-84-5, CAS No. 940929-33-9, CAS No. 336113-53-2, CAS No. 146-77-0, CAS No. 28822-58-4, CAS No. 477845-12-8, CAS No. 872573-93-8, CAS No. 724741-75-7, CAS No. 1357171-62-0, CAS No. 715934-43-2, any bioactive analog thereof, a plant cell-compatible salt thereof, an ester thereof, and any combination thereof; and
    (c) genome editing molecule(s) comprising: an RNA-guided nuclease or a polynucleotide encoding an RNA-guided nuclease, a guide RNA or a polynucleotide encoding a guide RNA, and a donor template DNA molecule;
        wherein the plant cell is associated with, contacts, and/or contains an effective amount of the HDR promoting agent and the genome editing molecule(s).

51. The composition of embodiment 50, wherein the plant cell is haploid, diploid, or polyploid.

52. The composition of embodiment 50 or 51, wherein the plant cell is in a culture medium, in a plant, in plant part, or in a plant tissue.

53. The composition of any one of embodiments 50 to 52, wherein the plant cell is grown under a hypoxic condition, or treated with an exogenous reactive oxygen species (ROS) one reactive oxygen species (ROS) concentration lowering agent, or both grown under the hypoxic condition and treated with the ROS scavenging agent.

54. The composition of embodiment 53, wherein the hypoxic condition comprises maintaining the cell in air comprising an oxygen concentration of about 12% to about 5% oxygen by volume, or wherein the cell is in a liquid culture medium and the hypoxic condition comprises maintaining the cell and the medium in air comprising an oxygen concentration of about 12% to about 5% oxygen by volume.

55. The composition of embodiment 53, wherein the reactive oxygen species (ROS) concentration lowering agent comprises an exogenously provided enzymatic ROS scavenging agent or an exogenously provided non-enzymatic ROS scavenging agent or a combination thereof.

56. The composition of any one of embodiments 53 to 55, wherein the HDR promoting agent is selected from the group consisting of a 5-substituted 2,4-oxazolidinedione, a 5-substituted 2, 4-thiazolidinedione, CAS No. 102649-78-5, CAS No. 549505-65-9, CAS No. 336113-53-2, CAS No. 146-77-0. CAS No. 28822-58-4, CAS No. 477845-12-8, CAS No. 872573-93-8, CAS No. 724741-75-7, CAS No. 1357171-62-0, CAS No. 715934-43-2, any bioactive analog thereof, a plant cell-compatible salt thereof, an ester thereof, and any combination thereof.

57. The composition of embodiment 56, wherein the 5-substituted 2, 4-thiazolidinedione is selected from the group consisting of Rosiglitazone (CAS No. 122320-73-4), Edaglitazone (CAS No. 213411-83-7), Ciglitazone (CAS No. 74772-77-3), Lobeglitazone (CAS No. 607723-33-1), Pioglitazone hydrochloride (CAS No. 112529-15-4), Troglitazone (CAS No. 97322-87-7), Mitoglitazone (CAS No. 146062-49-9), Darglitazone (CAS No. 141200-24-0), Englitazone (CAS No. 109229-58-5). Netoglitazone (CAS No. 161600-01-7), Rivoglitazone (CAS No. 185428-18-6), Balaglitazone (CAS No. 199113-98-9), and a plant cell-compatible salt thereof.

58. The composition of any one of embodiments 50 to 52, wherein the HDR-promoting agent is a 5-substituted 2, 4-thiazolidinedione.

59. The composition of embodiment 58, wherein the 5-substituted 2, 4-thiazolidinedione is selected from the group consisting of Rosiglitazone (CAS No. 122320-73-4), Edaglitazone (CAS No. 213411-83-7), Ciglitazone (CAS No. 74772-77-3), Lobeglitazone (CAS No. 607723-33-1), Pioglitazone hydrochloride (CAS No. 112529-15-4), Troglitazone (CAS No. 97322-87-7), Mitoglitazone (CAS No. 146062-49-9), Darglitazone (CAS No. 141200-24-0), Englitazone (CAS No. 109229-58-5), Netoglitazone (CAS No. 161600-01-7), Rivoglitazone (CAS No. 185428-18-6), Balaglitazone (CAS No. 199113-98-9), a bioactive analog thereof, and a plant cell-compatible salt thereof.

60. The composition of any one of embodiments 50 to 59, wherein a bioactive analog thereof is:
    (v) a substitution of a halogen with another halogen;
    (vi) a substitution of a C1 to C6 alkyl group or a C1 to C6 alkoxy group with a different C1 to C6 alkyl group or a different C1 to C6 alkoxy group, respectively;
    (vii) a substitution of an unsubstituted phenyl group with a substituted phenyl group, wherein optionally the substitutions in the phenyl group are selected from a methyl, an alkoxy, aminoalkyl, or halogen; and/or,
    (viii) a substitution of a substituted phenyl group with a different substituted phenyl group wherein optionally the substitutions in the phenyl group are selected from a methyl, an alkoxy, aminoalkyl, or halogen.

61. The composition of any one of embodiments 50 to 60, wherein the plant cell is contained or supported by a plant cell culture medium and Ca2+ and/or Mg2+ is provided in the plant cell culture medium at a concentration of about 40 mM to 150 mM.

62. The composition of any one of embodiments 50 to 61, wherein the composition comprising the HDR promoting agent further comprises an agriculturally acceptable adjuvant and/or excipient.

63. The composition of any one of embodiments 50 to 62, wherein the effective concentration of the HDR-promoting agent is about 0.1 µM, 0.25 µM, 0.5 µM, or about 1 µM to about 10 µM, 25 µM, 50 µM, 100 µM, or 500 µM.

64. The composition of embodiment 63, wherein the effective concentration of the HDR-promoting agent is about 0.1 µM, 0.05 µM, or 1 µM to about 10 µM, 25 µM, or 50 µM.

65. A composition comprising:
  (a) a eukaryotic cell;
  (b) at least one HDR promoting agent selected from the group consisting of a 5-substituted 2,4-oxazolidinedione, 5-substituted 2, 4-thiazolidinedione, CAS No. 102649-78-5, CAS No. 549505-65-9, CAS No. 336113-53-2, CAS No. 146-77-0, CAS No. 28822-58-4, CAS No. 477845-12-8, CAS No. 872573-93-8, CAS No. 724741-75-7, CAS No. 1357171-62-0, CAS No. 715934-43-2, any bioactive analog thereof, a eukaryotic cell-compatible salt thereof, an ester thereof, and any combination thereof; and
  (c) genome editing molecule(s) comprising: an RNA-guided nuclease or a polynucleotide encoding an RNA-guided nuclease, a guide RNA or a polynucleotide encoding a guide RNA, and a donor template DNA molecule;
    wherein the eukaryotic cell is a plant cell or an animal cell or a fungal cell or a protist cell; wherein the eukaryotic cell is associated with, contacts, and/or contains an effective amount of the HDR promoting agent and the genome editing molecule(s); and
    wherein the eukaryotic cell is grown under a hypoxic condition, or treated with an exogenous reactive oxygen species (ROS) one reactive oxygen species (ROS) concentration lowering agent, or both grown under the hypoxic condition and treated with the ROS scavenging agent.

66. The composition of embodiment 65, wherein the hypoxic condition comprises maintaining the eukaryotic cell in air comprising an oxygen concentration of about 12% to about 5% oxygen by volume, or wherein the eukaryotic cell is in a liquid culture medium and the hypoxic condition comprises maintaining the eukaryotic cell and the medium in air comprising an oxygen concentration of about 12% to about 5% oxygen by volume.

67. The composition of embodiment 65, wherein the reactive oxygen species (ROS) concentration lowering agent comprises an exogenously provided enzymatic ROS scavenging agent or an exogenously provided non-enzymatic ROS scavenging agent or a combination thereof.

EXAMPLES

Example 1

This example describes the use of small molecules having homology-dependent repair (HDR) promoting activity, including the use of such small molecules in combination with hypoxia to increase HDR efficiency. Experiments were designed to test the effects of small molecules and/or hypoxia on Homology Directed Repair (HDR) and Non-Homologous End Joining (NHEJ) on editing a reporter or endogenous gene.

The tests utilized a "traffic light" BFP-LP4/2A-mCherry reporter as the target gene to be edited. A ribonucleoprotein (RNP) with guide RNA (gRNA) targeting the BFP coding sequence (181-200 bp) was designed to introduce a double strand DNA break at 197 bp; this DNA break can be repaired through NHEJ pathway with a small indel which leads to in-frame expression of mCherry-NLS, or can be repaired through the HDR pathway when providing the donor template which leads to a 1bp single nucleotide variant (SNV) and the expression of Blue Fluorescent protein (BFP) to be changed to Green Fluorescent Protein (GFP). The experiments were carried out with protoplasts produced from etiolated leaves of B73 maize grown in the dark for 11 days. The protoplasts were co-transfected with the RNP and donor template along with the reporter plasmid. The small molecules in DMSO were provided to the cells at a final concentration of about 5 micromolar. Control cells were incubated with DMSO in the absence of the small molecules at a final concentration of 0.5% by volume. Transfected cells were incubated 48 hours at 26 degrees Celsius in the dark under either normoxic or hypoxic conditions in the presence and absence of the small molecules, and then harvested for imaging on a fluorescent microscope. Results as averaged relative fluorescence units (RFUs), total protoplast count, and GFP-expressing protoplast count per plate.

In this set of experiments, 81 small molecules effected a general increase in HDR efficiency. Fifty-one of the 81 small molecules showed a higher general increase in HDR efficiency under hypoxic conditions than normoxic conditions. Twenty-eight of the 81 small molecules showed a higher general increase under normoxic condition than hypoxic conditions.

Example 2

This example describes a second set of experiments which investigated the effects of the 81 small molecules previously identified in the "traffic light" screen (Example 1) on HDR efficiency in editing an endogenous gene, the maize (Zea mays) r1-colored1 gene with partial genomic sequence SEQ ID NO: 5. A ribonucleoprotein (RNP) was prepared with a guide RNA designed to edit the promoter located at positions 313-333 of SEQ ID NO:5. A donor template was provided as a dsDNA for HDR repair. The experiments were carried out with protoplasts produced from etiolated leaves of B104 maize grown in the dark for 11 days. The protoplasts were co-transfected with the RNP and donor template. Transfected cells were incubated 48 hours at 26 degrees Celsius in the dark under either normoxic or hypoxic conditions with the indicated negative controls, positive controls, and small molecules and then harvested. The negative controls comprised cells transfected with the RNP only (no donor template). DMSO controls comprised the RNP and donor template and DMSO at a final concentration of 0.5% by volume DMSO. The positive control was a mixture of KU-0060648 (CAS No. 881375-00-4; Fischer Scientific, Waltham, Mass., USA), STL127705 (7-[2-(3,4-dimethoxyphenyl)ethyl]amino-3-(3-fluorophenyl)pyrimido[4,5-d]pyrimidine-2,4(1H,3H)-dione); Vitas-M, Champaign, Ill., USA), NU7441 (CAS No. 503468-95-9; Fischer Scientific Waltham, Mass., USA), and SCR7 pyrazine (CAS No. 14892-97-8; Tocris, Minneapolis, Minn., USA) (all at a stock concentration of 5 mM in DMSO) that was provided to the protoplasts at a final concentration of each of the four compounds of 5 µM. Certain positive control compounds have been reported to increase CRISPR-mediated HDR (Robert et al. 2015; Chu et al., 2015). All of the tested small molecules were also provided to the protoplasts at a final concentration of 5 µM of the compound and a final DMSO concentration of 0.1% by volume. Genomic DNA was isolated using KAPA Pure Bead capture (Kapa Biosystem) and the isolated gDNA was used as the template for a PCR with PHUSION FLASH (ThermoFisher). Samples were cleaned with KAPA Pure Bead capture and Illumina libraries were prepared and sequenced on MiSeq.

In this set of experiments 63 small molecules showed a higher general increase in HDR editing of the endogenous target gene. Fifty-one small molecules of the 81 showed a higher general increase in HDR under hypoxic conditions than normoxic conditions. Twelve small molecules of the 81 showed a higher general increase in HDR under normoxic conditions than in hypoxic conditions.

A summary of the results obtained for selected small molecules which increased HDR is provided in the following Table. Small molecules which increased HDR in hypoxic conditions are in boldface.

TABLE 3

| Chemical | CAS NO. | Hypoxia Avg. | Hypoxia St. Dev | Normoxia Avg. | Normoxia St. Dev |
| --- | --- | --- | --- | --- | --- |
| NEG. CTRL 1 | | 0.06 | 0.03 | 2.90 | 0.33 |
| NEG. CTRL 2 | | 0.02 | 0.02 | 0.39 | 0.05 |
| NEG. CTRL 3 | | 1.26 | 0.05 | 0.23 | 0.17 |
| NEG. CTRL 4 | | 2.56 | 0.46 | 0.01 | 0.01 |
| NEG. CTRL. AVG1 | | 1.29 | 1.25 | 1.04 | 1.61 |
| DMSO 1 | | 0.81 | 0.28 | 1.69 | 0.35 |
| DMSO 2 | | 1.49 | 0.12 | 1.37 | 0.17 |
| DMSO 3 | | 0.01 | 0.00 | 0.00 | 0.00 |
| DMSO 4 | | 1.40 | 0.21 | 3.03 | 0.58 |
| DMSO 5 | | 0.01 | 0.00 | 0.01 | 0.02 |
| DMSO 6 | | 0.76 | 0.28 | 1.29 | 0.30 |
| DMSO 7 | | 0.03 | 0.04 | 5.14 | 0.28 |
| DMSO AVG2 | | 0.64 | 0.65 | 1.79 | 1.81 |
| POS. CTRL 1 | | 2.24 | 0.13 | 2.51 | 0.13 |
| POS. CTRL 2 | | 2.80 | 0.01 | 2.31 | 0.18 |
| POS. CTRL 3 | | 3.94 | 0.20 | 2.48 | 0.17 |
| POS. CTRL 4 | | 2.76 | 0.05 | 1.78 | 0.04 |
| POS. CTRL. AVG.3 | | 2.94 | 0.72 | 2.27 | 0.34 |
| SC-9 | 102649-78-5 | 5.11 | 0.39 | 2.67 | 0.39 |
| Pregnanolone | 128-20-1 | 2.52 | 0.16 | 4.43 | 0.27 |
| ML 3403 | 549505-65-9 | 4.36 | 0.43 | 1.47 | 0.27 |
| Daminozide | 1596-84-5 | 0.48 | 0.20 | 4.57 | 0.57 |
| Rosiglitazone | 122320-73-4 | 4.97 | 0.50 | 3.20 | 0.37 |
| SB 743921 Hydrochloride | 940929-33-9 | 2.97 | 0.22 | 4.76 | 0.72 |
| Ispinesib | 336113-53-2 | 4.04 | 0.25 | 3.36 | 0.22 |
| 2-Chloroadenosine | 146-77-0 | 5.00 | 0.63 | 2.45 | 0.16 |
| Edaglitazone | 213411-83-7 | 6.28 | 0.74 | 3.56 | 0.52 |
| IBMX | 28822-58-4 | 4.23 | 0.33 | 3.05 | 0.15 |
| PIM-1 Inhibitor 2 | 477845-12-8 | 5.19 | 0.12 | 1.37 | 0.30 |
| Ro 3306 | 872573-93-8 | 4.91 | 0.25 | 1.64 | 0.15 |
| STF 31 | 724741-75-7 | 5.00 | 0.67 | 0.40 | 0.04 |
| ML 228 | 1357171-62-0 | 4.49 | 0.52 | 0.46 | 0.03 |
| MI 14 | 715934-43-2 | 7.75 | 1.54 | 0.37 | 0.14 |

[1]Negative control cells were treated with RNPs only (no donor template). Negative control 1, 2, 3, and 4 averages are for triplicate samples and the standard deviation for the triplicate samples is shown. Negative control average is an average of the Negative Control 1, 2, 3, and 4 average values for each of the hypoxia and normoxia samples.
[2]DMSO control is RNP and donor template with DMSO at a final concentration of 0.5% by volume. DMSO 1-7 averages are for triplicate samples and the standard deviation for the triplicate samples is shown. DMSO Average is an average of the DMSO 1-7 average values for each of the hypoxia and normoxia samples.
[3]Positive control is at a final concentration of 5 µM for each compound (KU-0060648, CAS No. 881375-00-4; STL127705 (7-[2-(3,4-dimethoxyphenyl)ethyl]amino}-3-(3-fluorophenyl)pyrimido[4,5-dipyrimidine-2,4(1H, 3H)-dione); NU7441 (CAS No. 503468-95-9) and SCR7 pyrazine (CAS No. 14892-97-8). Positive control 1-4 averages are for triplicate samples and the standard deviation for the triplicate samples is shown. Positive control average is an average of the positive control 1-4 average values for each of the hypoxia and normoxia samples.

Example 3

Biological Sequences

This example provides non-limiting embodiments of protein and nucleic acid sequences referred to herein. Biological sequences and their SEQ ID NOs are set forth in Table 4.

TABLE 4

Biological Sequences

| SEQ ID NO: | DESCRIPTION | SEQUENCE | COMMENTS |
| --- | --- | --- | --- |
| 1 | As Cpf1 (wild type) | MTQFEGFTNLYQVSKTLRFELIPQGKTLKHIQEQGFIEED KARNDHYKELKPIIDRIYKTYADQCLQLVQLDWENLSAAI DSYRKEKTEETRNALIEEQATYRNAIHDYFIGRTDNLTDA INKRHAEIYKGLFKAELFNGKVLKQLGTVTTTEHENALLR | *Acidaminococcus* sp. (As) Cpf1 |

TABLE 4-continued

Biological Sequences

| SEQ ID NO: | DESCRIPTION | SEQUENCE | COMMENTS |
|---|---|---|---|
| | | SFDKFTTYFSGFYENRKNVFSAEDISTAIPHRIVQDNFPK FKENCHIFTRLITAVPSLREHFENVKKAIGIFVSTSIEEV FSFPPFYNQLLTQTQIDLYNQLLGGISREAGTEKIKGLNEV LNLAIQKNDETAHIIASLPHRFIPLFKQILSDRNTLSFIL EEFKSDEEVIQSFCKYKTLLRNENVLETAEALFNELNSID LTHIFISHKKLETISSALCDHWDTLRNALYERRISELTGK ITKSAKEKVQRSLKHEDINLQEIISAAGKELSEAFKQKTS EILSHAHAALDQPLPTTLKKQEEKEILKSQLDSLLGLYHL LDWFAVDESNEVDPEFSARLTGIKLEMEPSLSFYNKARNY ATKKPYSVEKEKLNEQMPTLASGWDVNKEKNNGAILFVKN GLYYLGIMPKQKGRYKALSFEPTEKTSEGFDKMYYDYFPD AAKMIPKCSTQLKAVTAHFQTHTTPILLSNNFIEPLEITK EIYDLNNPEKEPKKFQTAYAKKTGDQKGYREALCKWIDFT RDFLSKYTKTTSIDLSSLRPSSQYKDLGEYYAELNPLLYH ISFQRIAEKEIMDAVETGKLYLFQIYNKDFAKGHHGKPNL HTLYWTGLFSPENLAKTSIKLNGQAELFYRPKSRMKRMAH RLGEKMLNKKLKDQKTPIPDTLYQELYDYVNHRLSHDLSD EARALLPNVITKEVSHEIIKDRRFTSDKFFFHVPITLNYQ AANSPSKFNQRVNAYLKEHPETPIIGIDRGERNLIYITVI DSTGKILEQRSLNTIQQFDYQKKLDNREKERVAARQAWSV VGTIKDLKQGYLSQVIHEIVDLMIHYQAVVVLENLNFGFK SKRTGIAEKAVYQQFEKMLIDKLNCLVLKDYPAEKVGGVL NPYQLTDQFTSFAKMGTQSGFLFYVPAPYTSKIDPLTGFV DPEVWKTIKNHESRKHELEGEDFLHYDVKTGDFILHEKMN RNLSFQRGLPGEMPAWDIVFEKNETQFDAKGTPFIAGKRI VPVIENHRFTGRYRDLYPANELIALLEEKGIVFRDGSNIL PKLLENDDSHAIDTMVALIRSVLQMRNSNAATGEDYINSP VRDLNGVCFDSRFQNPEWPMDADANGAYHIALKGQLLLNH LKESKDLKLQNGISNQDWLAYIQELRN | |
| 2 | LbCpf1 (wild type) | MSKLEKFTNCYSLSKTLRFKAIPVGKTQENIDNKRLLVED EKRAEDYKGVKKLLDRYYLSFINDVLHSIKLKNLNNYISL FRKKTRTEKENKELENLEINLRKEIAKAFKGNEGYKSLFK KDIIETILPEFLDDKDEIALVNSFNGFTTAFTGFFDNREN MFSEEAKSTSIAFRCINENLTRYISNMDIFEKVDAIEDKH EVQEIKEKILNSDYDVEDFFEGEFFNFVLTQEGIDVYNAI IGGFVTESGEKIKGLNEYINLYNQKTKQKLPKFKPLYKQV LSDRESLSFYGEGYTSDEEVLEVFRNTLNKNSEIFSSIKK LEKLFKNFDEYSSAGIFVKNGPAISTISKDIFGEWNVIRD KWNAEYDDIHLKKKAVVTEKYEDDRRKSFKKIGSFSLEQL QEYADADLSVVEKLKEIIIQKVDEIYKVYGSSEKLFDADF VLEKSLKKNDAVVAIMKDLLDSVKSFENYIKAFFGEGKET NRDESFYGDFVLAYDILLKVDHIYDAIRNYVTQKPYSKDK FKLYFQNPQFMGGWDKDKETDYRATILRYGSKYYLAIMDK KYAKCLQKIDKDDVNGNYEKINYKLLPGPNKMLPKVFFSK KWMAYYNPSEDIQKIYKNGTFKKGDMFNLNDCHKLIDFFK DSISRYPKWSNAYDFNFSETEKYKDIAGFYREVEEQGYKV SFESASKKEVDKLVEEGKLYMFQIYNKDFSDKSHGTPNLH TMYFKLLFDENNHGQIRLSGGAELFMRRASLKKEELVVHP ANSPIANKNPDNPKKTTTLSYDVYKDKRFSEDQYELHIPI AINKCPKNIFKINTEVRVLLKHDDNPYVIGIDRGERNLLY IVVVDGKGNIVEQYSLNEIINNFNGIRIKTDYHSLLDKKE KERFEARQNWTSIENIKELKAGYISQVVHKICELVEKYDA VIALEDLNSGFKNSRVKVEKQVYQKFEKMLIDKLNYMVDK KSNPCATGGALKGYQITNKFESFKSMSTQNGFIFYIPAWL TSKIDPSTGFVNLLKTKYTSIADSKKFISSFDRIMYVPEE DLFEFALDYKNFSRTDADYIKKWKLYSYGNRIRIFRNPKK NNVFDWEEVCLTSAYKELFNKYGINYQQGDIRALLCEQSD KAFYSSFMALMSLMLQMRNSITGRTDVDFLISPVKNSDGI FYDSRNYEAQENAILPKNADANGAYNIARKVLWAIGQFKK AEDEKLDKVKIAISNKEWLEYAQTSVKH | Lachnospiraceae bacterium (Lb) Cpf1 |
| 3 | Fn Cpf1 (wild type) | MSIYQEFVNKYSLSKTLRFELIPQGKTLENIKARGLILDD EKRAKDYKKAKQIIDKYHQFFIEEILSSVCISEDLLQNYS DVYFKLKKSDDDNLQKDFKSAKDTIKKQISEYIKDSEKFK NLFNQNLIDAKKGQESDLILWLKQSKDNGIELFKANSDIT DIDEALEIIKSFKGWTTYFKGFHENRKNVYSSNDIPTSII YRIVDDNLPKFLENKAKYESLKDKAPEAINYEQIKKDLAE ELTFDIDYKTSEVNQRVFSLDEVFEIANFNNYLNQSGITK FNTIIGGKFVNGENTKRKGINEYINLYSQQINDKTLKKYK MSVLFKQILSDTESKSFVIDKLEDDSDVVTTMQSFYEQIA AFKTVEEKSIKETLSLLFDDLKAQKLDLSKIYFKNDKSLT DLSQQVFDDYSVIGTAVLEYITQQIAPKNLDNPSKKEQEL IAKKTEKAKYLSLETIKLALEEFNKHRDIDKQCRFEEILA NFAAIPMIFDEIAQNKDNLAQISIKYQNQGKKDLLQASAE DDVKAIKDLLDQTNNLLHKLKIFHISQSEDKANILDKDEH | Francisella novicida (Fn) Cpf1 |

TABLE 4-continued

Biological Sequences

| SEQ ID NO: | DESCRIPTION | SEQUENCE | COMMENTS |
|---|---|---|---|
| | | FYLVFEECYFELANIVPLYNKIRNYITQKPYSDEKFKLNF<br>ENSTLANGWDKNKEPDNTAILFIKDDKYYLGVMNKKNNKI<br>FDDKAIKENKGEGYKKIVYKLLPGANKMLPKVFFSAKSIK<br>FYNPSEDILRIRNHSTHTKNGSPQKGYEKFEFNIEDCRKF<br>IDFYKQSISKHPEWKDFGFRFSDTQRYNSIDEFYREVENQ<br>GYKLTFENISESYIDSVVNQGKLYLFQIYNKDFSAYSKGR<br>PNLHTLYWKALFDERNLQDVVYKLNGEAELFYRKQSIPKK<br>ITHPAKEAIANKNKDNPKKESVFEYDLIKDKRFTEDKFFF<br>HCPITINFKSSGANKFNDEINLLLKEKANDVHILSIDRGE<br>RHLAYYTLVDGKGNIIKQDTFNIIGNDRMKTNYHDKLAAI<br>EKDRDSARKDWKKINNIKEMKEGYLSQVVHEIAKLVIEYN<br>AIVVEEDLNEGEKRGREKVEKQVYQKLEKMLIEKLNYLVE<br>KDNEEDKTGGVLRAYQLTAPEETEKKMGKQTGITYYVPAG<br>ETSKICPVTGEVNQLYPKYESVSKSQEFFSKEDKICYNLD<br>KGYFEESEDYKNEGDKAAKGKWTIASFGSRLINFRNSDKN<br>HNWDTREVYPTKELEKLLKDYSIEYGHGECIKAAICGESD<br>KKFFAKLTSVLNTILQMRNSKTGTELDYLISPVADVNGNE<br>EDSRQAPKNMPQDADANGAYHIGLKGLMLLGRIKNNQEGK<br>KLNLVIKNEEYFEFVQNRNN | |
| 4 | CasJ<br>(wild type) | MQQYQVSKTVRFGLTLKNSEKKHATHLLLKDLVNVSEERI<br>KNEITKDDKNQSELSFFNEVIETLDLMDKYIKDWENCFYR<br>TDQIQLTKEYYKVIAKKACEDWFWTNDRGMKEPTSSIISF<br>NSLKSSDKSKTSDNLDRKKKILDYWKGNIFKTQKAIKDVL<br>DITEDIQKAIEEKKSHREINRVNHRKMGIHLIHLINDTLV<br>PLCNGSIFEGNISKLDECESENEKLIDEASTEKQDERKEL<br>LSKINEIKQYFEDNGGNVPFARATLNRHTANQKPDRYNEE<br>IKKLVNELGVNSLVRSLKSKTIEEIKTHEEFENKNKINEL<br>KNSFVLSIVEKIQLFKYKTIPASVRFLLADYFEEQKLSTK<br>EEALTIFEEIGKPQNIGFDYIQLKEKDNFTLKKYPLKQAF<br>DYAWENLARLDQNPKANQESVDECKRFEKEVESMEMDNIN<br>EKTYALLLALKEKTTAFDKKGEGAAKNKSEIIEQIKGVFE<br>ELDQPFKIIANTLREEVIKKEDELNVLKRQYRETDRKIKT<br>LQNEIKKIKNQIKNLENSKKYSFPEIIKWIDLTEQEQLLD<br>KNKQAKSNYQKAKGDLGLIRGSQKTSINDYFYLTDKVYRK<br>LAQDFGKKMADLREKLLDKNDVNKIKYLSYIVKDNQGYQY<br>TLLKPLEDKNAEIIELKSEPNGDLKLEEIKSLTSKTLNKF<br>IKNKGAYKEFHSAEFEHKKIKEDWKNKYKYNSDFIVKLKKC<br>LSHSDMANTQNWKAFGWDLDKCKSYETIEKEIDQKSYQLV<br>EIKLSKTTIEKWVKENNYLLLPIVNQDITAEKLKVNTNQF<br>TKDWQHIFEKNPNHRLHPEENIAYRQPTKDYAKEGEKRYS<br>REQLTGQEMYEYIPQDANYISRKEQITLFNDKEEQKIQVE<br>TFNNQIAKILNAEDFYVIGIDRGITQLATLCVLNKNGVIQ<br>GGFEIFTREEDYTNKQWKHTKLKENRNILDISNLKVETTV<br>NGEKVLVDLSEVKTYLRDENGEPMKNEKGVILTKDNLQKI<br>KLKQLAYDRKLQYKMQHEPELVLSFLDRLENKEQIPNLLA<br>STKLISAYKEGTAYADIDIEQFWNILQTFQTIVDKEGGIE<br>NAKKTMEERQYTELDASFDLKNGVVANMVGVVKFIMEKYN<br>YKTFIALEDLTFAFGQSIDGINGERLRSTKEDKEVDFKEQ<br>ENSTLAGLGTYHEFEMQLLKKLSKTQIGNEIKHEVPAERS<br>TENYEKIVRKDKNVKAKIVSYPEGIVSFVNPRNTSISCPN<br>CKNANKSNRIKKENDRILCKHNIEKTKGNCGEDTANEDEN<br>KLRAENKGKNFKYISSGDANAAYNIAVKLLEDKIFEINKK | CasJ |
| 5 | | GGGTTGTTGTGGGTTGAACCCGTCCCAACCATCATCAACT<br>CGCTAGCCAAACACACGCTTAGGGGCCAAAGCAGTGCTAT<br>AATATGAGTGGTGGCGCTATTATATATAGCGTCAGAGAAC<br>TTAGATCTGATATTCTGATGAAGAAAAAATGACTACTGAC<br>TACGAAAGAAGAAGAAAGGAGCTATAGAGAGAGAAGAGGG<br>GTCGTGTAGTAGTGCTTAAACTGTACATGAACAGCAGTAG<br>TGTTACAGAAGCTAAACTCAACCAGAGCTCCACCAAAGAC<br>AAAGAGGGTCTACTTCCATCACCGTCTTGCTCGGTCACTT<br>GGAGCTCTGTCCATAAATTAAACCCATCGTGGCATATCTG<br>TAGGCATCTACCCCGTCTTCGTCGTCCGTTCCTCACTAGC<br>TACCAAGAGGTCGCCATTATTGCCAACATAGAGTGTACGT<br>GGATGTCTATATATATGCCTACTTGCACCCATATGGC | |
| 6 | type II CRISPR<br>RNA-guided<br>endonuclease<br>Cas9<br>[Actinobacillus<br>suis] | MKLTPLNYILGLDLGIASVGWAVVEIDEQENPLGLIDVGV<br>RTFDRAEVPKTGESLALARRLARSARRLVKRRADRIKKAK<br>RLLKAENILLSADEHLPNDVWQLRVKGLDQKLERQEWAAV<br>LLHLLKHRGYLSQRKNESKSENKELGALLSGVETNHQILQ<br>SAEYRTPAEIAVKKFHVEDGHIRNQRGAYTHTFSRLDLLA<br>EMELLFQRQTDLGNPHTSAKLLENLTALLMWQKPALAGEA<br>ILKMLGKCTFEPTEYKAAKNSYSAERFVWLTKLNNLRILE<br>QGAERALTDNERFALLDQPYEKAKFTYAQARTMLALPDEA<br>IFKGVRYQGEDKKAVETKTILMEMKAYHQIRKALENADLK | WP_014991277.1 |

TABLE 4-continued

Biological Sequences

| SEQ ID NO: | DESCRIPTION | SEQUENCE | COMMENTS |
|---|---|---|---|
| | | AEWNELKNNSELLDDIGTAFSLHKTDEDICRYLDGKLSES<br>ILNALLENLNFDKFIQLSLKALQQILPLMLQGQRYDEAVS<br>AIYGDHYGKKSAEINRLLPTIPADEIRNPVVLRTLTQARK<br>VINAVVRLYGSPARIHIETGREVGKSYQDRKKLEKQQEDN<br>RKQRESAVKKFKEYFPNFVGEPKGKDILKMRLYELQQAKC<br>LYSGKSLELHRLLEKGYVEVDHALPFSRTWDDSFNNKVLV<br>LANENQNKGNLTPYEWLDGKNNSEHWQNEVARVQTSGESH<br>TKKQRILSHKLDEKGFIERNLNDTRYVARFLCNFIADNML<br>LTGKGKRKVFASNGQITALLRGRWGLQKVRDDNDRHHALD<br>AVVVACSTVVMQQKITRFVRYEEGNVFSGERIDRETGEII<br>PLHEPSPWAFFRENVEIRIFSENPKLELENRLPDYPQYNH<br>EFVQPLFVSRMPTRKMTGQGHMETVKSAKRLDEGLSVLKV<br>PLTQLKLSDLERMVNREREVTLYESLKARLEQFGNDPAKA<br>FAEPFHKKGGAVVKAVRVEQTQKSGVLVRDGNGVADNASM<br>VRVDVFTKGGKYFLVPIYTWQVAKGILPNKAVTANVDEID<br>WLEMDESYQFIFTMYPNDLVKVKLKKEEFFGYYGGLDRAT<br>GAIVIKEHDLEKSKGKQGIYRIGVKLALSFEKYQVDELGK<br>NIRPCRPTKRQHVR | |

The breadth and scope of the present disclosure should not be limited by any of the above-described Examples, but should be defined only in accordance with the preceding embodiments, the following claims, and their equivalents.

REFERENCES

Brettschneider, R., D. Becker, and H. Lörz. 1997. "Efficient Transformation of Scutellar Tissue of Immature Maize Embryos." *Theoretical and Applied Genetics* 94 (6-7): 737-48. doi: 10.1007/s001220050473.

Čermák, Tomáš, Shaun J. Curtin, Javier Gil-Humanes, Radim Čegan, Thomas J. Y. Kono, Eva Koneečná, Joseph J. Belanto, et al. 2017. "A Multipurpose Toolkit to Enable Advanced Genome Engineering in Plants." *The Plant Cell Online* 29 (6): 1196-1217. doi: 10.1105/tpc.16.00922.

Chu V T, Weber T, Wefers B, Wurst W, Sander S, Rajewsky K, Kühn R. Increasing the efficiency of homology-directed repair for CRISPR-Cas9-induced precise gene editing in mammalian cells. Nat Biotechnol. 2015 May; 33 (5):543-8. doi:10.1038/nbt.3198.

Dotson S B, Lanahan M B, Smith A G, Kishore G M. A phosphonate monoester hydrolase from *Burkholderia caryophilli* PG2982 is useful as a conditional lethal gene in plants. Plant J. 1996 August; 10(2):383-92.

Richard M. Clark, Simon Tavaré, John Doebley, Estimating a Nucleotide Substitution Rate for Maize from Polymorphism at a Major Domestication Locus, *Molecular Biology and Evolution,* Volume 22, Issue 11, November 2005, Pages 2304-2312, doi: 10.1093/molbev/msi228.

Frame, Bronwyn, Marcy Main, Rosemarie Schick, and Kan Wang. 2011. "Genetic Transformation Using Maize Immature Zygotic Embryos." *Methods in Molecular Biology* (Clifton, N.J.) 710: 327-41. https://doi.org/10.1007/978-1-61737-988-8_22.

Gao, Caixia, Jin-Long Qiu, Jinxing Liu, Kunling Chen, Yanpeng Wang, Yi Zhang, Yuan Zong, and Zhen Liang. 2016. "Efficient and Transgene-Free Genome Editing in Wheat through Transient Expression of CRISPR/Cas9 DNA or RNA." *Nature Communications* 7 (August): 12617. doi: 10.1038/ncomms12617.

Hamada, Haruyasu, Yuelin Liu, Yozo Nagira, Ryuji Miki, Naoaki Taoka, and Ryozo Imai. 2018. "Biolistic-Delivery-Based Transient CRISPR/Cas9 Expression Enables in Planta Genome Editing in Wheat." *Scientific Reports* 8 (1): 14422. \doi: 10.1038/s41598-018-32714-6.

Honig, Arik, Ira Marton, Michal Rosenthal, J. Jeff Smith, Michael G. Nicholson, Derek Jantz, Amir Zuker, and Alexander Vainstein. 2015. "Transient Expression of Virally Delivered Meganuclease In Planta Generates Inherited Genomic Deletions." *Molecular Plant* 8 (8): 1292-94. doi: 10.1016/j.molp.2015.04.001.

Jiang W, Bikard D, Cox D, Zhang F, Marraffini L A. RNA-guided editing of bacterial genomes using CRISPR-Cas systems. Nat Biotechnol. 2013 March; 31(3):233-9.doi: 10.1038/nbt.2508.

Jinek M, Chylinski K, Fonfara I, Hauer M, Doudna J A, Charpentier E. A programmable dual-RNA-guided DNA endonuclease in adaptive bacterial immunity. Science. 2012 Aug. 17; 337(6096):816-21. doi: 10.1126/science.1225829.

Kirienko D R, Luo A, Sylvester A W. Reliable transient transformation of intact maize leaf cells for functional genomics and experimental study. Plant Physiol. 2012 August; 159(4):1309-18. doi: 10.1104/pp. 112.199737.

Liu, Wusheng, Joshua S. Yuan, and C. Neal Stewart. 2013. "Advanced Genetic Tools for Plant Biotechnology." *Nature Reviews. Genetics* 14 (11): 781-93. doi: 10.1038/nrg3583.

Long L, Guo D D, Gao W, Yang W W, Hou L P, Ma X N, Miao Y C, Botella J R, Song C P. Optimization of CRISPR/Cas9 genome editing in cotton by improved sgRNA expression. Plant Methods. 2018 Oct. 3; 14:85. doi: 10.1186/s13007-018-0353-0.

Lynch M. Evolution of the mutation rate. Trends Genet. 2010 August; 26(8):345-52. doi: 10.1016/j.tig.2010.05.003

Martin-Ortigosa, Susana, and Kan Wang. 2014. "Proteolistics: A Biolistic Method for Intracellular Delivery of Proteins." *Transgenic Research* 23 (5): 743-56. doi: 10.1007/s11248-014-9807-y.

Momose Y, Maekawa T, Yamano T, Kawada M, Odaka H, Ikeda H, Sohda T. Novel 5-substituted 2,4-thiazolidinedione and 2,4-oxazolidinedione derivatives as insulin sensitizers with antidiabetic activities. J Med Chem. 2002 Mar. 28; 45(7):1518-34.

Murphy, K. 2016. λ Recombination and Recombineering, EcoSal Plus 2016. doi:10.1128/ecosalplus.

Nagle M, Déjardin A, Pilate G, Strauss S H. Opportunities for Innovation in Genetic Transformation of Forest Trees. Front Plant Sci. 2018 Oct. 2; 9:1443. doi: 10.3389/fpls.2018.01443.

Nussaume, L. Vincentz, M., and Caboche, M. 1991. Constitutive Nitrate Reductase: a dominant conditional marker for plant genetics. The Plant J. 1(2):267-274.

Nuccio M., Chen X., Conville J., Zhou A., Liu X. (2015) Plant Trait Gene Expression Cassette Design. In: Azhakanandam K., Silverstone A., Daniell H., Davey M. (eds) Recent Advancements in Gene Expression and Enabling Technologies in Crop Plants. Springer, New York, N.Y.

O'Reilly D, Kartje Z J, Ageely E A, Malek-Adamian E, Habibian M, Schofield A, Barkau C L, Rohilla K J, DeRossett L B, Weigle A T, Damha M J, Gagnon K T. Extensive CRISPR RNA modification reveals chemical compatibility and structure-activity relationships for Cas9 biochemical activity. Nucleic Acids Res. 2019 Jan. 25; 47(2):546-558. doi: 10.1093/nar/gky 1214.

Robert F, Barbeau M, Éthier S, Dostie J, Pelletier J. Pharmacological inhibition of DNA-PK stimulates Cas9-mediated genome editing. Genome Med. 2015. Aug. 27; 7:93. doi: 10.1186/s13073-015-0215-6.

Sivamani, E., Nalapalli, S., Prairie, A. et al. Mol Biol Rep (2019). https://doi.org/10.1007/s11033-019-04737-3.

Schindele P, Wolter F, Puchta H. Transforming plant biology and breeding with CRISPR/Cas9, Cas12 and Cas13. FEBS Lett. 2018 June; 592(12):1954-1967. doi:10.1002/1873-3468.13073.

Schlaman, H R M., and Hooykaas, P. J. J. (1997) Effectiveness of the bacterial gene codA encoding cytosine deaminase as a negative selectable marker in *Agrobacterium*-mediated plant transformation. Plant Journal 11(6):1377-1385.

Soda, Neelam, Lokesh Verma, and Mender Giri. 2017. "CRISPR-Cas9 Based Plant Genome Editing: Significance, Opportunities and Recent Advances." *Plant Physiology and Biochemistry*, October. doi: 10.1016/j.plaphy.2017.10.024.

Urnov, Fyodor D., Edward J. Rebar, Michael C. Holmes, H. Steve Zhang, and Philip D. Gregory. 2010. "Genome Editing with Engineered Zinc Finger Nucleases." *Nature Reviews. Genetics* 11 (9): 636-46. doi: 10.1038/nrg2842.

Wang K, Fredens J, Brunner S F, Kim S H, Chia T, Chin J W. Defining synonymous codon compression schemes by genome recoding. Nature. 2016 Nov. 3; 539(7627):59-64. doi: 10.1038/nature20124.

Wang, Kan, and Bronwyn Frame. 2009. "Biolistic Gun-Mediated Maize Genetic Transformation." *Methods in Molecular Biology (Clifton, N.J.)* 526: 29-45. doi: 10.1007/978-1-59745-494-0_3.

Wang, Wei, Qianli Pan, Fei He, Alina Akhunova, Shiaoman Chao, Harold Trick, and Eduard Akhunov. 2018. "Transgenerational CRISPR-Cas9 Activity Facilitates Multiplex Gene Editing in Allopolyploid Wheat." *The CRISPR Journal* 1 (1): 65-74. doi: 10.1089/crispr.2017.0010.

Yin H, Song C Q, Suresh S, Wu Q, Walsh S, Rhym L H, Mintzer E, Bolukbasi M F, Zhu L J, Kauffman K, Mou H, Oberholzer A, Ding J, Kwan S Y, Bogorad R L, Zatsepin T, Koteliansky V, Wolfe S A, Xue W, Langer R, Anderson D G. Structure-guided chemical modification of guide RNA enables potent non-viral in vivo genome editing. Nat. Biotechnol. 2017 December; 35(12):1179-1187. doi: 10.1038/nbt.4005.

Zhang, Yi, Zhen Liang, Yuan Zong, Yanpeng Wang, Jinxing Liu, Kunling Chen, Jin-Long Qiu, and Caixia Gao. 2016. "Efficient and Transgene-Free Genome Editing in Wheat through Transient Expression of CRISPR/Cas9 DNA or RNA." *Nature Communications* 7 (August): 12617. doi: 10.1038/ncomms12617.

---

What is claimed is:

1. A method for increasing Homology Directed Repair (HDR)-mediated genome modification of a maize plant cell genome, comprising:
providing genome editing molecules to a maize plant cell in culture,
wherein the maize plant cell is exposed to a composition comprising at least one HDR promoting agent selected from the group consisting of a 5-substituted 2, 4-thiazolidinedione, CAS No. 102649-78-5, CAS No. 128-20-1, CAS No. 549505-65-9, CAS No. 1596-84-5, CAS No. 940929-33-9, CAS No. 336113-53-2, CAS No. 146-77-0, CAS No. 28822-58-4, CAS No. 477845-12-8, CAS No. 872573-93-8, CAS No. 724741-75-7, CAS No. 1357171-62-0, CAS No. 715934-43-2, a plant cell-compatible salt thereof, an ester thereof, and any combination thereof, wherein said plant cell is exposed to a concentration of about 0.5 μM to about 50 μM of said HDR promoting agent;
wherein the genome editing molecules comprise an RNA-guided nuclease or a polynucleotide encoding an RNA-guided nuclease, a guide RNA or a polynucleotide encoding a guide RNA, and a donor template DNA molecule;
whereby the genome editing molecules modify the maize plant cell genome by HDR at a frequency that is increased in comparison to a control method wherein a control maize plant cell is provided with the genome editing molecules but is not exposed to at least one of said HDR promoting agents or any combination thereof.

2. The method of claim 1, wherein the frequency of HDR is increased by at least 1.5-fold, at least 2-fold, or at least 3-fold in comparison to the control.

3. The method of claim 1, wherein the maize plant cell is haploid, diploid, or polyploid.

4. The method of claim 1, wherein the level of at least one oxygen species is lowered in the maize plant cell by exposure of the plant cell to a hypoxic condition, or by exposure of the maize plant cell to at least one reactive oxygen species (ROS) concentration lowering agent, or by exposure of the maize plant cell to both a hypoxic condition and to at least one ROS concentration lowering agent.

5. The method of claim 4, wherein the hypoxic condition comprises maintaining the maize plant cell in air comprising an oxygen concentration of about 12% to about 5% oxygen by volume, or wherein the maize plant cell is in a liquid culture medium and the hypoxic condition comprises maintaining the cell and the medium in air comprising an oxygen concentration of about 12% to about 5% oxygen by volume.

6. The method of claim 4, wherein the reactive oxygen species (ROS) concentration lowering agent comprises an exogenously provided enzymatic ROS scavenging agent, or an exogenously provided non-enzymatic ROS scavenging agent, or a combination thereof.

7. The method of claim 4, wherein the HDR promoting agent is selected from the group consisting of a 5-substituted 2, 4-thiazolidinedione, CAS No. 102649-78-5, CAS No. 549505-65-9, CAS No. 336113-53-2, CAS No. 146-77-0, CAS No. 28822-58-4, CAS No. 477845-12-8, CAS No. 872573-93-8, CAS No. 724741-75-7, CAS No. 1357171-62-0, CAS No. 715934-43-2, a plant cell-compatible salt thereof, an ester thereof, and any combination thereof.

8. The method of claim 7, wherein the 5-substituted 2, 4-thiazolidinedione is selected from the group consisting of Rosiglitazone (CAS No. 122320-73-4), Edaglitazone (CAS No. 213411-83-7), Ciglitazone (CAS No. 74772-77-3), Lobeglitazone (CAS No. 607723-33-1), Pioglitazone hydrochloride (CAS No. 112529-15-4), Troglitazone (CAS No. 97322-87-7), Mitoglitazone (CAS No. 146062-49-9), Darglitazone (CAS No. 141200-24-0), Englitazone (CAS No. 109229-58-5), Netoglitazone (CAS No. 161600-01-7), Rivoglitazone (CAS No. 185428-18-6), Balaglitazone (CAS No. 199113-98-9), and a plant cell-compatible salt thereof.

9. The method of claim 1, wherein the HDR-promoting agent is a 5-substituted 2, 4-thiazolidinedione.

10. The method of claim 9, wherein the 5-substituted 2, 4-thiazolidinedione is selected from the group consisting of Rosiglitazone (CAS No. 122320-73-4), Edaglitazone (CAS No. 213411-83-7), Ciglitazone (CAS No. 74772-77-3), Lobeglitazone (CAS No. 607723-33-1), Pioglitazone hydrochloride (CAS No. 112529-15-4), Troglitazone (CAS No. 97322-87-7), Mitoglitazone (CAS No. 146062-49-9), Darglitazone (CAS No. 141200-24-0), Englitazone (CAS No. 109229-58-5), Netoglitazone (CAS No. 161600-01-7), Rivoglitazone (CAS No. 185428-18-6), Balaglitazone (CAS No. 199113-98-9), and a plant cell-compatible salt thereof.

11. The method of claim 1, wherein the composition comprising the HDR promoting agent further comprises an agriculturally acceptable adjuvant and/or excipient.

12. The method of claim 1, wherein the maize plant cell is contained or supported by a plant cell culture medium and $Ca^{2+}$ and/or $Mg^{2+}$ is provided in the plant cell culture medium at a concentration of about 40 mM to 150 mM.

13. The method of claim 1, further comprising the step of isolating and/or growing a maize plant cell, propagule, or plant obtained from the maize plant cell comprising the genomic modification, wherein the genome of the maize plant cell, propagule, or plant comprises the genomic modification.

14. A system for modification of a maize plant gene, comprising:
    (a) a maize plant cell in culture;
    (b) at least one HDR promoting agent selected from the group consisting of 5-substituted 2, 4-thiazolidinedione, CAS No. 102649-78-5, CAS No. 128-20-1, CAS No. 549505-65-9, CAS No. 1596-84-5, CAS No. 940929-33-9, CAS No. 336113-53-2, CAS No. 146-77-0, CAS No. 28822-58-4, CAS No. 477845-12-8, CAS No. 872573-93-8, CAS No. 724741-75-7, CAS No. 1357171-62-0, CAS No. 715934-43-2, a plant cell-compatible salt thereof, an ester thereof, and any combination thereof; and
    (c) genome editing molecule(s) comprising: an RNA-guided nuclease or a polynucleotide encoding an RNA-guided nuclease, a guide RNA or a polynucleotide encoding a guide RNA, and a donor template DNA molecule;
    (d) wherein the maize plant cell contacts about 0.5 μM to about 50 μM of the at least one HDR promoting agent and the genome editing molecule(s) in the culture.

15. A method for making a maize plant cell having a genomic modification, comprising:
    (a) providing genome editing molecules to a maize plant cell in culture,
        wherein the maize plant cell is exposed to about 0.5 μM to about 50 μM of at least one HDR promoting agent selected from the group consisting of a 5-substituted 2, 4-thiazolidinedione, CAS No. 102649-78-5, CAS No. 128-20-1, CAS No. 549505-65-9, CAS No. 1596-84-5, CAS No. 940929-33-9, CAS No. 336113-53-2, CAS No. 146-77-0, CAS No. 28822-58-4, CAS No. 477845-12-8, CAS No. 872573-93-8, CAS No. 724741-75-7, CAS No. 1357171-62-0, CAS No. 715934-43-2, a plant cell-compatible salt thereof, an ester thereof, and any combination thereof;
        wherein the genome editing molecules comprise an RNA-guided nuclease or a polynucleotide encoding an RNA-guided nuclease, a guide RNA or a polynucleotide encoding a guide RNA, and a donor template DNA molecule; and
    (b) whereby the genome editing molecules modify the maize plant cell genome by homology directed repair (HDR) at a frequency that is increased in comparison to a control; and isolating or propagating a plant cell comprising the genome modification, thereby making the plant cell having a genomic modification.

16. The method of claim 15, wherein the level of at least one oxygen species is lowered in the maize plant cell by exposure of the maize plant cell to a hypoxic condition, or by exposure of the maize plant cell to at least one reactive oxygen species (ROS) concentration lowering agent, or by exposure of the maize plant cell to both a hypoxic condition and to at least one ROS concentration lowering agent.

17. The method of claim 16, wherein the hypoxic condition comprises maintaining the maize plant cell in air comprising an oxygen concentration of about 12% to about 5% oxygen by volume, or wherein the maize plant cell is in a liquid culture medium and the hypoxic condition comprises maintaining the cell and the medium in air comprising an oxygen concentration of about 12% to about 5% oxygen by volume.

18. The method of claim 15, wherein the maize plant cell is exposed to from about 1 μM to about 25 μM of the at least one HDR promoting agent.

19. The method of claim 1, wherein the maize plant cell is exposed to from about 1 μM to about 25 μM of the at least one HDR promoting agent.

20. The system of claim 14, wherein the maize plant cell contacts from about 1 μM to about 25 μM of the at least one HDR promoting agent.

* * * * *